United States Patent [19]
Phillips et al.

[11] Patent Number: 5,977,429
[45] Date of Patent: Nov. 2, 1999

[54] SYNTHETIC POLYESTER ABSORBENT MATERIALS

[75] Inventors: Bobby Mal Phillips, Jonesborough; Shriram Bagrodia, Kingsport, both of Tenn.

[73] Assignee: Eastman Chemical Company, Kingsport, Tenn.

[21] Appl. No.: 08/916,071

[22] Filed: Aug. 21, 1997

Related U.S. Application Data

[60] Provisional application No. 60/024,302, Aug. 22, 1996.

[51] Int. Cl.$^6$ ...................................................... A61F 13/15
[52] U.S. Cl. ........................................... 604/370; 604/372
[58] Field of Search .................................... 604/367, 370, 604/372

[56] References Cited

U.S. PATENT DOCUMENTS

| | | |
|---|---|---|
| 3,219,739 | 11/1965 | Breen et al. . |
| 4,223,677 | 9/1980 | Anderson . |
| 4,888,093 | 12/1989 | Dean et al. . |
| 4,889,596 | 12/1989 | Schoggen et al. . |
| 4,898,642 | 2/1990 | Moore et al. . |
| 4,976,819 | 12/1990 | Minton . |
| 5,151,465 | 9/1992 | Le-Khac . |
| 5,200,248 | 4/1993 | Thompson et al. . |
| 5,268,229 | 12/1993 | Phillips et al. . |
| 5,611,981 | 3/1997 | Phillips et al. . |

FOREIGN PATENT DOCUMENTS

| | | |
|---|---|---|
| 0 450 923 | 10/1991 | European Pat. Off. . |

*Primary Examiner*—John G. Weiss
*Assistant Examiner*—Dennis Ruhl
*Attorney, Agent, or Firm*—Cheryl J. Tubach; Harry J. Gwinnell

[57] ABSTRACT

The invention provides synthetic polymeric fibers which have utility as temporary acquisition/distribution absorbent structures and permanent storage/distribution absorbent structures in a wide range of absorbent products such as diapers, feminine napkins, and adult incontinent pads. These fibers are short, highly distorted, and bulky characterized by lengths between 2 and 37 mm, short-range distortion factors between 5 and 70, long-range distortion factors between 0.05 and 0.9, and single fiber bulk factors between 0.5 and 10.0. They may or may not have capillary channels on the surface. The advantages of these materials are their increased absorbency, reduced wet collapse at low densities, reduced rewet, reduced loss of liquid under pressure, and their ability to be desorbed by distribution materials such as capillary channeled fibers or by conventional storage materials such as fluff pulp or superabsorbent polymer fiber or powder.

40 Claims, 32 Drawing Sheets

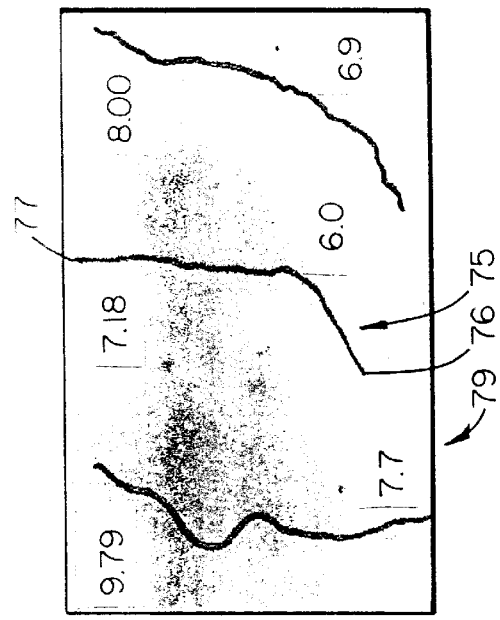
Fig. 7C
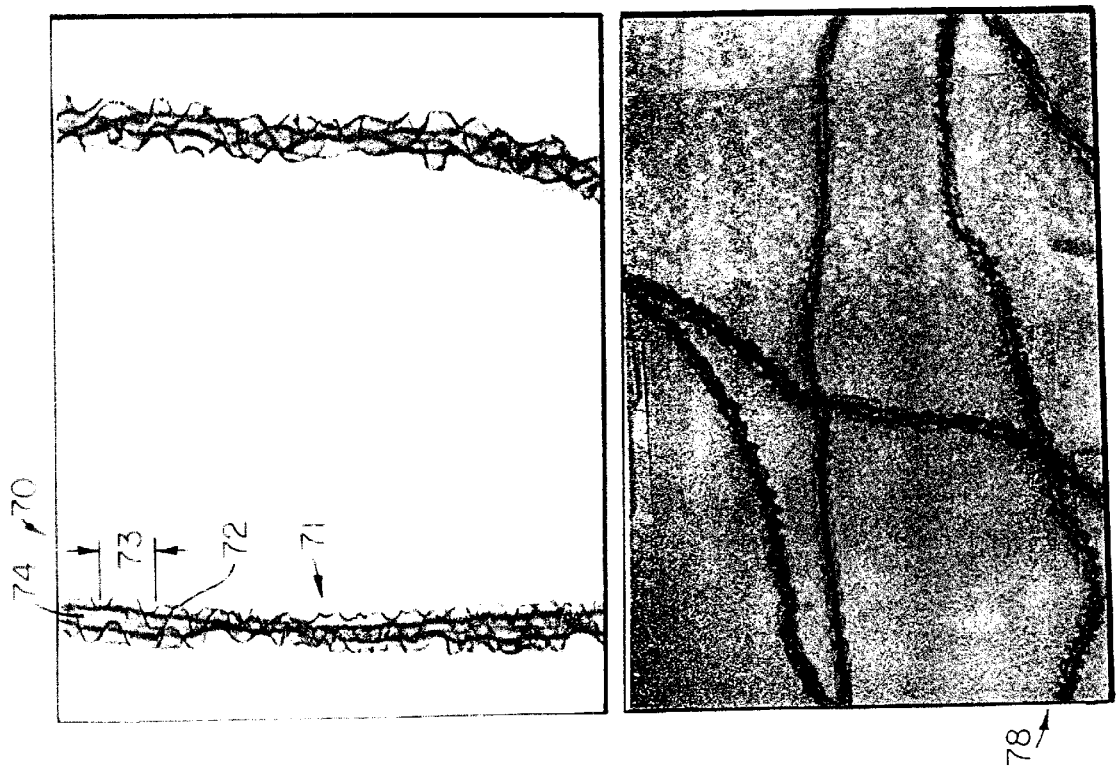
Fig. 7A
Fig. 7B

SYNTHETIC POLYESTER ABSORBENT MATERIALS

This application claims the benefit of U.S. Provisional application Ser. No. 60/024,302 filed Aug. 22, 1996.

FIELD OF THE INVENTION

This invention relates to components of absorbent products and absorbent products. More specifically, this invention relates to fibers and structures of the fibers that acquire, distribute and store fluids for use in absorbent products.

BACKGROUND OF THE INVENTION

Cellulose fluff pulp is a common component in the core of disposable absorbent products, such as diapers, catamenials, and incontinent pads. Cellulose fluff pulp is relatively inexpensive. Superabsorbent polymer (SAP) in fiber or powder form is another component that is often found in the core of disposable absorbent products. Core materials like cellulose fluff pulp, chemically modified fluff pulp, or SAP are not easily desorbed because the thermodynamic attraction of aqueous liquids for these materials is extremely high. Hence, liquid in a region containing these materials generally cannot be transported through or away from that region making fluid distribution difficult. Cellulose fluff pulp also collapses when saturated with liquid. This collapse has long been a problem in the absorbent products art limiting their utility.

U.S. Pat. Nos. 4,898,642 to Moore et al.; 4,888,093 to Dean et al.; 4,889,596 to Schoggen et al. and 4,976,819 to Minton describe various chemically modified fluff pulps directed to remedy the deficiencies of untreated fluff pulp.

U.S. Pat. No. 3,219,739 to Breen discloses poly(ethylene terephthalate) (PET) fibers and a process for making those fibers. The fibers disclosed in the '739 patent are characterized by having arms, a relatively high spatial frequency, and relatively short-range sinuous (ruffle) or spiral geometries in the arms. The relatively short range is on the order of ten microns. The fibers disclosed in the '739 patent will not spontaneously transport water. That is, a liquid in contact with the cross-section of a single one of the fibers disclosed in the '739 patent will not continuously spread from the place of contact along the length of the fiber.

U.S. Pat. No. 5,611,981 to Phillips et al. discloses spontaneously wettable fibers having a combination of X values and surface contact angles that satisfy conditions for spontaneous wetting. The X factor is defined therein as $X=P_W/(4r+(\pi-2)D)$ where $P_W$ is the wetted perimeter of the filament, r is the radius of the circumscribed circle circumscribing the fiber's cross-section, and D is the minor axis dimension across the fiber's cross-section. The teachings of the '981 patent are hereby incorporated herein by reference as if fully set forth herein.

U.S. Pat. No. 5,200,248 to Thompson et al. discloses capillary channel polymeric fibers, which store and transport liquid. The fibers have non-round cross-section shapes which include relatively long thin portions. The cross-section shapes are the same along the length of the fiber. The '248 patent discloses that these capillary channel fibers may be coated with materials that provide an adhesion tension with water of at least 25 dynes/cm. The teachings and especially the definitions in the '248 patent are hereby incorporated by reference as if fully set forth herein.

U.S. Pat. No. 5,268,229 to Phillips et al. discloses fibers having nonround cross-sectional shapes, specifically "U" and "E" shaped cross-sections with stabilizing legs. These fibers are also spontaneously wettable fibers and have cross-sections that are the same along the length of the fiber.

Co-pending U.S. application titled "Bundles of Fibers Useful for Moving Liquids at High Fluxes and Acquisition/Distribution Structures that Use the Bundles" filed Aug. 15, 1997, discloses bundles of fibers for use as distribution materials. The individual fibers themselves are poor distribution materials having no intra-fiber capillary channels. When combined with each other in bundles, the bundles become excellent distribution materials by utilizing inter-fiber capillary channels. The teachings of and especially the definitions are hereby incorporated herein by reference as if fully set forth herein.

SUMMARY OF THE INVENTION

A highly distorted, bulky synthetic polymeric fiber acquires, distributes and stores fluids when made into an absorbent structure having a large number of the fibers in close proximity to one another. The fibers have a length of between 2 and about 37 millimeters, cross-sections that vary in shape along the length of the fiber, a single fiber bulk factor between 0.5 and 10.0, a short range distortion factor greater than 5, and a long range distortion factor between 0.05 and 0.9. In several preferred embodiments the fiber has at least one cross-section along its length that is characterized as having a distorted "H" shape, a distorted "Y" shape, a distorted "+" shape, a distorted "U" shape, or a distorted shape of a fiber having a cross-section as shown in FIG. 17. The fibers are primarily for use in absorbent products such as diapers, catamenials, and incontinent devices, thus the fibers preferably have an adhesion tension on their surface of greater than 25 dynes/cm with distilled water for adequate movement of aqueous fluids. The fiber surface may be coated with a superabsorbent polymer or a blend of superabsorbent polymer and surfactant.

The absorbent structure comprising the novel fibers of the invention function to manage fluids by temporarily acquiring and distributing fluids. When the novel fibers are coated with a superabsorbent polymer or combined with other materials such as fluff pulp, chemically modified fluff pulp, superabsorbent polymer or combinations thereof, the absorbent structure created functions to permanently store fluids. These absorbent structures have improved water absorbency, decreased wet collapse and reduce water release over many conventional absorbent structures. The absorbent structures in combination with top sheets, distribution layers, shielding layers, storage cores, and back sheets make excellent absorbent products with reduced leakage, improved absorbency and complete utilization of the storage core.

Processes for making the novel fibers of the invention include the step sequences of (1) spinning, optionally drawing, cutting, and shrinking or (2) spinning, optionally drawing, shrinking, and cutting. These processes may be done continuously and at high speeds.

BRIEF DESCRIPTION OF THE DRAWINGS

FIG. 7A is a photocopy of a color photograph at 80X of the novel fibers of Example 2.

FIG. 7B is a photocopy of a color photograph at 36X of the novel fibers of Example 2.

FIG. 7C is a photocopy of a color photograph at 7X of the novel fibers of Example 2.

DETAILED DESCRIPTION OF THE INVENTION

Figure 1:
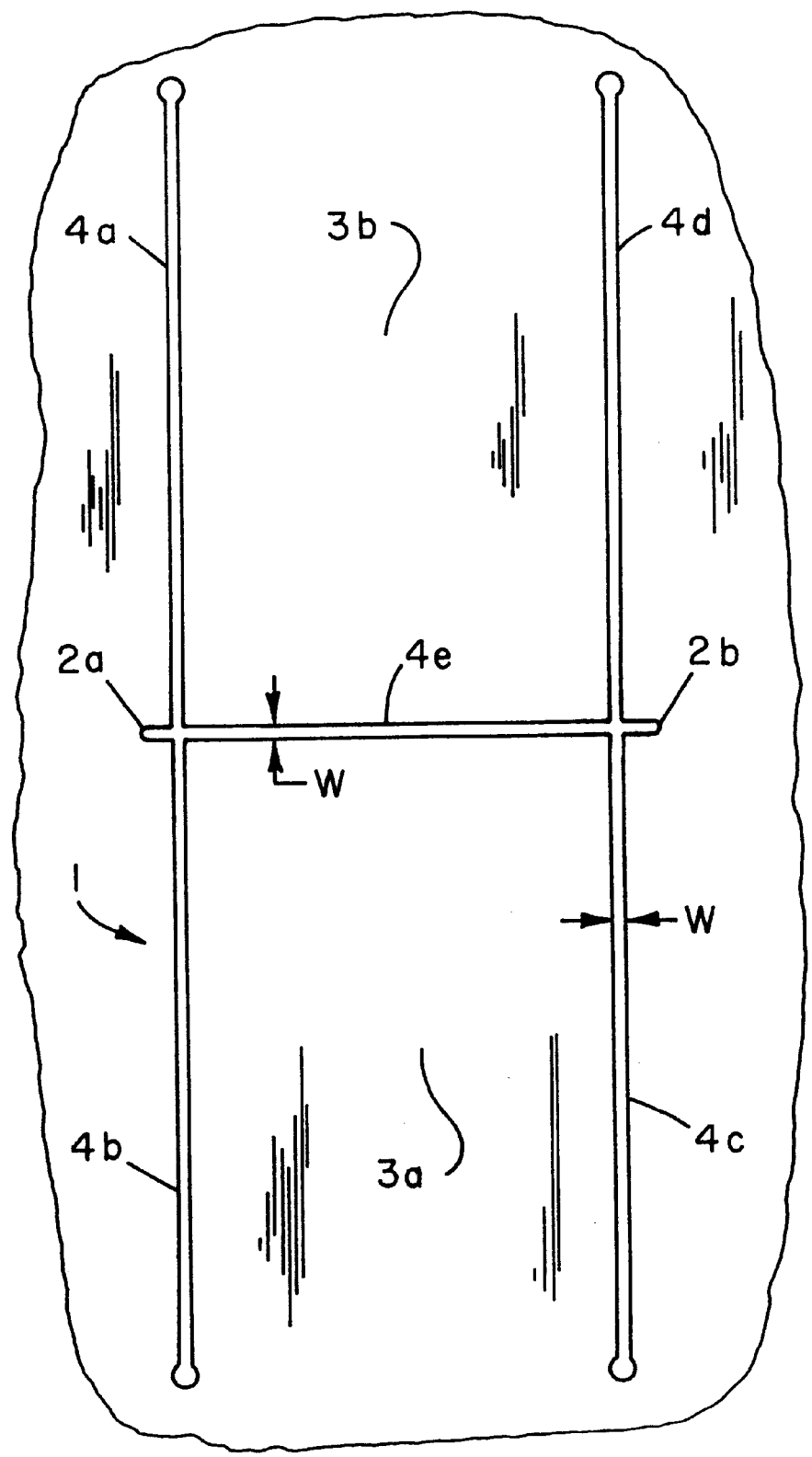
FIG. 1 is a schematic in plan view of an H-shaped aperture of a spinnerette identified as I-1083 used in Example 1.

Novel absorbent structures are made of a plurality of novel fibers in proximity to each other. The novel fibers are short, highly distorted having varying cross-section shapes along their lengths, and bulky. The absorbent structures provide fluid management properties functioning to either temporarily acquire and distribute fluids or permanently store fluids. The fluid management properties depend on the type of novel fibers utilized in the absorbent structures. The absorbent structures are used in absorbent products, such as diapers, catamenials, or incontinent devices.

The novel fibers are short meaning that each fiber has a length along its axis of between about 2 and about 37 millimeters, preferably between about 2 and 19 millimeters.

The novel fibers are bulky meaning that each fiber has a single fiber bulk factor (SFBF) of between 0.5 and 10.0, preferably between 1.5 and 7.5. The examples represent SFBF of between 0.5 and 4.0. SFBF is a measure of the ratio of void areas formed by the cross-section of the fiber to the polymer area of the cross-section of the fiber. The void areas are illustrated in the fiber cross-sections of FIGS. 28A–B along with exemplary calculations as discussed below. Since the novel fibers have varying crosssections along their length, the SFBF is an average of 50 cross-section measurements.

Bulkiness may also be expressed as a function of the as spun fiber. "As spun" means the state of the novel fibers prior to the step of shrinking or drawing. The as spun fibers have non-round cross-section shapes and include those fibers disclosed in U.S. Pat. Nos. 5,200,248; 5,268,229 and 5,611,981 and in co-pending U.S. application titled "Bundles of Fibers Useful for Moving Liquids at High Fluxes and Acquisition/Distribution Structures that Use the Bundles" filed Aug. 15, 1997. In combining the teachings of the above references, the as spun fibers may be characterized by the following two classifications:

1. The fibers are those classified as having "good" capillary channels on their surface such that the fibers have (a) a Specific Capillary Volume of at least 2.0 cc/g and a Specific Capillary Surface Area of at least 2000 cm$^2$/g, or (b) a Slenderness Ratio of at least 9 and at least 30 percent of intra-fiber channels with a capillary channel width of less than 300 microns.
2. The fibers are those classified as having "poor" or no capillary channels on their surface such that the fibers have (a) a Specific Capillary Volume of less than 2.0 cc/g or a Specific Capillary Surface Area of less than 2000 cm$^2$/g, and (b) a Slenderness Ratio of less than 9 or more than 70% of intra-fiber channels with a capillary channel width of greater than 300 microns. Preferably, these as spun fibers have a SFBF of greater than 4.0.

Details of measuring the parameters set forth above for the as spun fibers are discussed below.

The novel fibers are highly distorted having a highly variable cross-section shapes caused by a sinuous or ruffled character of arms of the fiber or walls of channels of the fiber relative to the backbone or spine of the fiber from which the arms or the walls project. That is, the arms or walls of the cross-section of the fibers are highly distorted. The distorted shape in this context is created from the shape of an as spun fiber that has undergone the step of shrinking. During shrinking, the cross-section shape of the as spun fiber distorts. Channels refers to the ruffled walls coupled with a base defining one or more channels.

Distortions of the novel fiber of the present invention are characterized by a short range distortion factor (SRDF) for the arms of the fiber or the walls of the channels and a long-range distortion factor (LRDF) for the length, i.e backbone, of the fiber. The SRDF is greater than 5.0, preferably between 5 and 70, and more preferably between 18 and 36. The LRDF is between 0.05 and 0.9, preferably between are 0.1 and 0.6. Examples herein represent SRDF of between 11 and 66 and LRDF of between 0.10 and 0.49.

The SRDF is defined as the percent of the coefficient variation of the ratio of the area of channels $C_{area}$ to the area of the cross-section of the fiber material $M_{area}$ for fifty measurements on randomly selected cross-sections of the fibers. Thus, $$SRDF = 100 \times (\sigma/X)$$

wherein X equals the average ($C_{area}/M_{area}$) for measurements on fifty cross-sections and $\sigma$ equals the standard deviation of the 50 values for ($C_{area}/M_{area}$).

Figure 29:
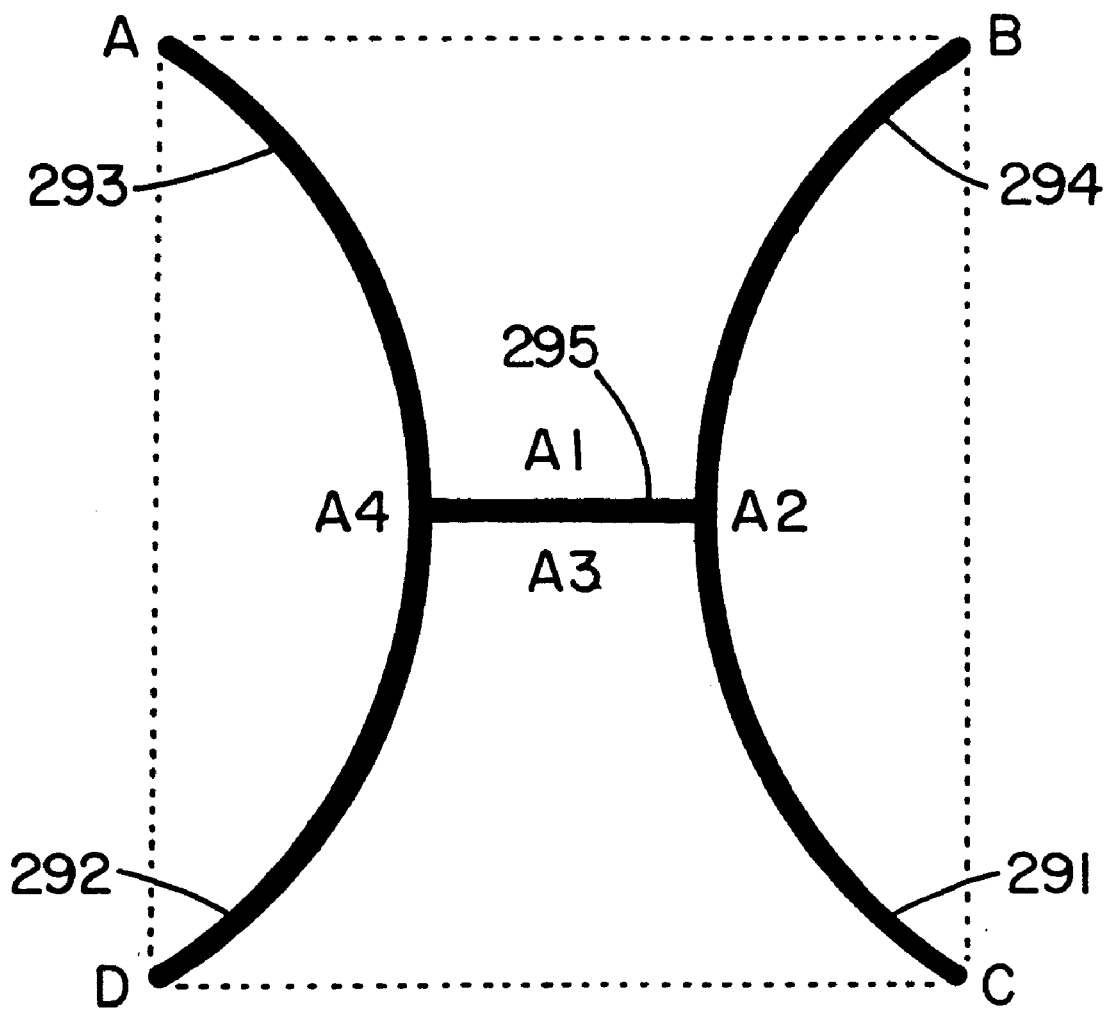
FIG. 29 is a schematic cross-section of a fiber useful in defining the short-range distortion factor (SRDF).

FIG. 29 illustrates a fiber cross-section and is useful in explaining how the channel area of a fiber is calculated. For any cross-section, the channel area $C_{area}$ is determined by first enclosing the cross-section in a polygon whose segments are tangent to two points on the cross-section and intersect at angles interior to the polygon of less than 180 degrees. The polygon is demonstrated in FIG. 29 as the dotted line segments. Each channel area is defined by the surfaces of the cross-section of the fiber and the line segments tangent to the two points on the cross-section. In FIG. 29 the line segment AB and surfaces of the two arms 293, 294, and the base 295 of the fiber delimit the channel area A1. Similarly, the line segment BC and surfaces of the two arms 291, 294 delimit the channel area A2. All channel areas are included in the value for $C_{area}$ for cross-section of a fiber. Thus, the value of $C_{area}$ is equal to the sum of the area of channels A1+A2+A3+A4. The fiber material area Marea is the area of the cross-section of the fiber, which includes the area of the arms 291–294 and the base 295. For each cross section, the ratio of $C_{area}$ to $M_{area}$ is determined. The average and the standard deviation of the ratio of the $C_{area}$ to $M_{area}$ is determined for fifty cross sections. Once the average and the standard deviation have been measured, the SRDF is calculated.

LRDF is a function of Lhd 1and $L_0$. $L_0$ is the average length along the backbone or spine of the novel fiber. $L_1$ is the diameter of the circle circumscribing the novel fiber. $L_0$ and $L_1$ are measured using photomicrographs. The fibers are placed on a microscope slide and a photomicrograph at a known magnification, such as a magnification of about 7, is taken. The lengths $L_1$ and $L_0$, while measured from the photomicrograph, are the actual lengths of the backbone and diameter, respectively. These lengths may be approximated using a ruler. Alternatively, a computer imaging and measurement system may be used to determine $L_0$, $L_1$, and LRDF.

In one embodiment as utilized by the examples below, the computer based imaging and measurement system to determine LRDF includes an optical system for obtaining images of the fiber, which is programmed with algorithms for measuring lengths of the fiber, and a printer for making copies of the fiber images. The optical system includes an illuminated base, a video camera equipped with a macro lens, and a conventional personal computer that includes an image grabber board. The width of the field of view for each image is preferably at least 15 millimeters at the desired magnification allowing for the entire length of the novel fibers to be in the field of view. Verification of the magnification in the image is done using a ruler in the field of view and an algorithm that sets the scale in the image field based upon the distance between points identified in the field of view.

Various algorithms can be used in the measuring system to determine $L_0$ and $L_1$. The determination of $L_0$ may be accomplished by tracing the insertion point along the length of the image of the fiber using an input/output mouse type of device. Alternatively, the ends of the image of the fiber can be identified using a mouse type device and the computer can be instructed to run an algorithm to determine the length of the fiber based upon the identification of the two end points and fiber image in the image field. $L_1$ can also be determined with the aid of the measuring system. The distal points of the fiber can be identified and the length between those points equated with the diameter of the circumscribing circle. Alternatively, the points in the image field corresponding to the fiber can be identified by the computer, and the computer can run an algorithm to fit a circle around the fiber that circumscribes the fiber.

To provide bulkiness and distortion, the shape of the cross-section of the novel fibers may be distorted "H", "Y", "+", or "U" shapes as shown in the Examples. The novel fiber cross-section shape may also be a distorted shape of the as spun fiber shown in FIG. 17. The shape of the as spun fiber in FIG. 17 has been commercially referred to as "4DG", available from Eastman Chemical Company of Kingsport, TN. Of course, the as spun fiber cross-section shapes are the non-distorted "H", "Y", "+", "U" or "4DG" shapes.

The fibers have a denier of between 3 and 100 dpf and more preferably between 3 and 30 dpf. Denier (dpf) is the average denier of the individual fiber measured in grams of fiber per 9000 meters of the individual fiber.

Preferably, the novel fibers of the invention are made from a polyester, such as poly(ethylene terephthalate). However, the novel fibers may also be formed from other polymers that shrink significantly when heated such as polystyrene or foamed polystyrene. The step of shrinking introduces the distortion in the fiber that increases the LRDF and SRDF. The relatively large values of LRDF and/or SRDF of the novel fibers provide their utility in absorbent products. Shrinking occurs for oriented amorphous polymeric fibers when the fibers are heated above their glass transition temperature. The shrinking occurs either prior to or in the absence of substantial crystallization.

The novel fibers of the invention, preferably, have a surface composition that is hydrophilic which may be inherent due the nature of the material used to make the fibers or may be fabricated by application of surface finishes. Hydrophilic surface finishes provide structures the surfaces of which have large adhesion tension (i.e., that strongly attract) with aqueous liquids and are therefore preferred for applications involving aqueous liquids such as those discussed below for temporary acquisition/distribution structures and permanent storage structures. Preferably, the hydrophilic surface has an adhesion tension with distilled water greater than 25 dynes/cm as measured on a flat surface having the same composition and finish as the surface of the fiber. Some of the finishes/lubricants useful to provide large adhesion tensions to aqueous liquids are described or referenced in U.S. Pat. No. 5,611,981. Surface finishes are well known in the art.

The surface finishes are typically coated on fibers during their manufacture. The coating, i.e. lubricating step, usually occurs just after the molten polymer is extruded through the aperture of a spinnerette and quenched, but it can be applied later as discussed below. The thickness of the coating is much thinner than the cross-section of the fiber and is measured in terms of its percent of the total weight of the fiber. The weight percent of the coating is typically between 0.005 and 2.0 percent of the total weight of the fiber.

Preferably, the fibers have a specific surface force, which is mathematically determined by the following equation:

$$(P y \cos(\theta a))/d \geq 0.03 \text{ dynes/den}$$

wherein P is the perimeter of the cross-section of the fiber in centimeters (cm); y is the surface tension of the liquid on the surface in dynes/cm; $\theta a$ is the advancing contact angle of the liquid on a flat surface having the same composition and finish as the surface of the fiber (as specified in U.S. Pat. No. 5,611,981); $y \cos(\theta a)$ is the adhesion tension of the liquid on the surface of the fiber; and d is the denier of the fiber on which the P was measured. Novel fibers which satisfy this inequality have excellent flow of fluid along their length.

The novel fibers have channels on their surface which may be useful in distributing or storing liquids when the proper surface energetics exist on the surface of the fibers, such as when the fibers satisfy the above equation relating to specific surface forces. The surface energetics determine the adhesion tension between the surface and whatever liquid is in contact with the surface. The larger the adhesion tension, the stronger the force of attraction between the liquid and the surface. The adhesion tension is one factor in the capillary forces acting on the liquid in a channel. Another factor affecting the capillary forces acting on a liquid in a channel is the length of the perimeter of the channel. When the widths of the channels are small, the capillary forces are relatively strong compared to the force of gravity on the liquid, since the force of gravity on the liquid in a channel is proportional to the area of the channel. Therefore, preferably, the width of the channels is less than 400 microns.

The important advantages of the novel fibers of the present invention are provided (1) by the capillaries defined in the final fiber being less than 400 microns, (2) by the relatively large ratio of the void volume (for storing liquid) to the volume of the material forming the fibers, and (3) by the bulk and rigidity provided by the large LRDF of the fibers. Novel fibers of the present invention may also contain channels which are larger than 400 microns. These features provide the novel fibers with the ability to acquire, transport, and store a relatively large capacity of liquid, and to prevent that liquid from being expelled when the structure is squeezed with moderate pressure. "V"-shaped grooves and/ or grooves with wide bases may also be used for these purposes.

The novel fiber of the present invention may also be coated with a superabsorbent polymer (SAP) to increases the ability of the fiber to absorb liquid. Preferably, the novel fibers are coated with up to 35 weight percent of SAP. An additive, such as a surfactant, is preferably mixed with the SAP thereby increasing the hydrophilicity of the mixture relative to the pure SAP. Preferably, the SAP is a copolymer of maleic anhydride and isobutylene. Preferably, the surfactant is a nonionic ethoxylated fatty acid ester. These SAP coated novel fibers are useful in novel absorbent structures which permanently store, whereas the novel fibers without the SAP coating are useful to temporarily store and distribute liquids.

Surprisingly, the initial contact angle of water on a SAP is high. For example, the contact angle of water on the surface of the SAP of Example 6 was visually estimated at about 60 degrees. The contact angle of aqueous liquids on SAP must be reduced in order to have sufficient adhesion tension between the aqueous liquid and the SAP to draw the liquid into and along the channels of the novel fibers. The additive to the SAP lowers the initial contact angle of an aqueous liquid on the SAP surface and enhances transportability of the aqueous liquid in the partially filled grooves.

The novel fibers may be used to address a significant problem with the prior art absorbent products known as gel blocking. For example, gel blocking of SAP occurs when high blend levels of SAP with fluff pulp of greater than 30 percent SAP are used at high densities of greater than 0.10 g/cc to make the currently popular thin diapers. Selected novel fibers of this invention when blended with SAP and fluff pulp will reduce gel blocking.

Novel absorbent structures of the present invention, which function to temporarily acquire and distribute fluids, are made of an assembly of the novel fibers described above. The bulk density of these temporary acquisition/distribution (TA) structures is similar to the bulk density of cellulose fluff pulp, which is preferably less than 0.15 grams per cubic centimeter. The function of temporarily acquiring fluids means that the TA structures may be desorbed by materials which have a greater thermodynamic attraction to the fluids than the TA structures themselves. Examples of desorbing materials in order of increasing thermodynamic attraction include distribution materials, such as those disclosed in U.S. Pat. Nos. 5,200,248; 5,268,229 and 5,611,981 and in co-pending U.S. application titled "Bundles of Fibers Useful for Moving Liquids at High Fluxes and Acquisition/ Distribution Structures that Use the Bundles" filed Aug. 15, 1997; fluff pulp; chemically modified fluff pulp; SAP containing materials.

The TA structures preferably have an absorbency of at least 6 grams of water absorbed per gram of material in the structure. The TA structures are resistive to the release of absorbed liquid under pressure. Preferably, the TA structures have less than 50 percent, more preferably less than 30 percent, water released at one pound per square inch (psi) of pressure. The TA structures have a significant reduction in liquid given up under pressure when compared to fluff pulp.

Wet collapse is typically a problem with cellulose fluff pulp, which has a wet collapse of about 25 percent at a bulk density of 0.0393 g/cc. The TA structures, however, have a wet collapse at a bulk density of 0.0393 g/cc of less than 12 percent, more preferably less than 5 percent and still more preferably essentially zero.

In another embodiment of the present invention the novel fibers are utilized in absorbent structures to permanently store fluids along the length of the fibers. The permanent storage (PS) structures comprise the novel fibers coated with SAP and, preferably, with a blend of SAP and surfactant, as described above. The SAP or blend is coated on or partially fills the channels. By using the blend of SAP and surfactant the length of the novel fibers is utilized in the storage of fluids within the channels of the fibers. The PS structures preferably have an absorbency of at least 20 grams of water absorbed per grams of material in the structure, water release at 1 psi of less than 30 percent and a $R_{avg}$ of greater than 2.5 g/sec.

The novel fibers of the present invention and those coated with SAP may be mixed or blended with fluff pulp, chemically treated fluff pulp, SAP or combinations thereof to provide additional structures for permanently storing fluids. In particular blends of the novel fibers of the present invention with fluff pulp provide a permanent storage structure having a wet collapse of less than 5 percent at a density of 0.393 g/cc.

Figure 30:
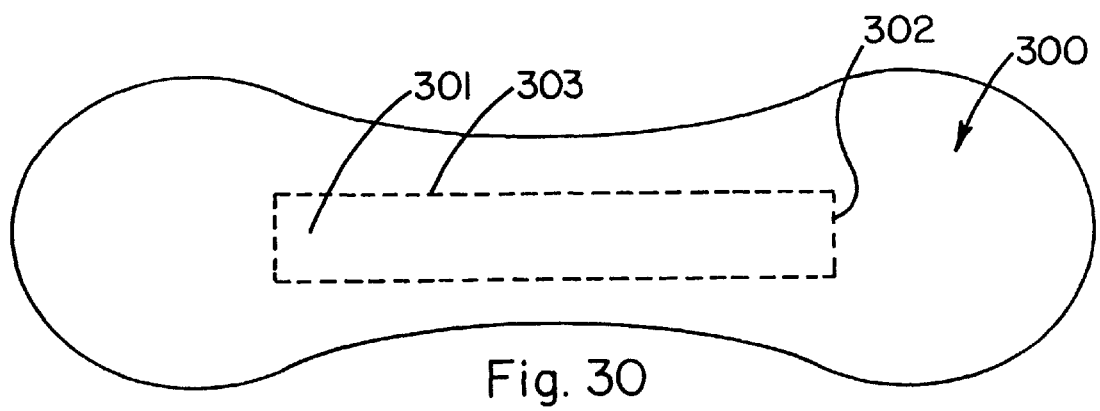
FIG. 30 is a schematic top plan view of an absorbent article.

Consumer disposable absorbent products such as diapers, catamenials, adult incontinent devices are improved using the novel fibers and TA and PS structures of the present invention. For example, FIG. 30 shows a plan view of a design for a feminine napkin 300 having a center area 301 designated by a width 302 and a length 303. Several embodiments of the feminine napkin 300 are shown in FIGS. 31–33 utilizing the novel structures of the present invention.

Figure 31:
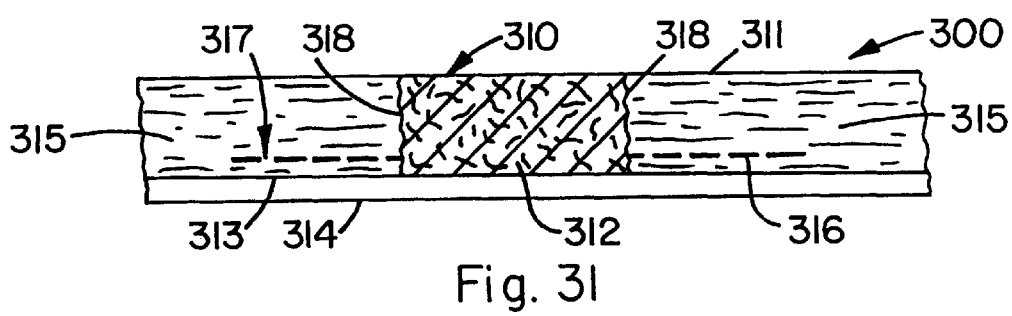
FIG. 31 is a partial side sectional view of a preferred embodiment of an absorbent article utilizing the absorbent structures of the present invention.

As shown in FIG. 31 the feminine napkin 300 is designed so that a primary impingement zone 310 comprises a portion of a top sheet 311, a TA structure 312 under the top sheet, and a portion of a distribution layer 313 which is just above a portion of back sheet 314. On either side of the impingement zone 310 is a storage core 315. A shielding strip 316 having openings 317 is underneath the storage core and above the distribution layer 313. The distribution layer is above the back sheet 314 and has a length 303, as shown in FIG. 30. The TA structure 312 is protected from communicating with the storage core 315 by shielding strips 318. Optionally, the TA structure may communicate with the core material 315 by adding openings to the shielding strip 318 or by not having any shielding strip. The distribution layer 313 links the impingement zone 310 to the outer areas of the core material 315 through the opening 317 of the shielding strip 316.

The feminine napkin design of FIG. 31 demonstrates the unique features of the novel fibers and in particular the TA structures of the present invention. The top sheet 311 of the feminine napkin 300 is insulted by an aqueous fluid at the impingement zone 310. The TA structure 312 temporarily acquires the aqueous fluid from the top sheet 311. The aqueous fluid in the TA structure 312 is desorbed by the distribution layer 313 and transferred to the storage core 315. At various points along the length of the storage core 315 designated by the openings 317 of the shielding strip 316, the aqueous fluid is desorbed from the distribution layer to a storage core. This process of fluid management allows for numerous insults to the impingement zone because the TA structures are drained by the storage core, thereby preparing the TA structures for another insult. The process may be repeated until the storage core is saturated. This feminine napkin design allows for complete utilization of the storage core and reduces leakage providing a product that overcomes the problems associated with prior art designs. This same basic design may be applied to diapers and adult incontinent devices. Obviously, the size (volume) of the TA structure will depend on the type of absorbent product that the TA structure is a component of.

Figure 32:
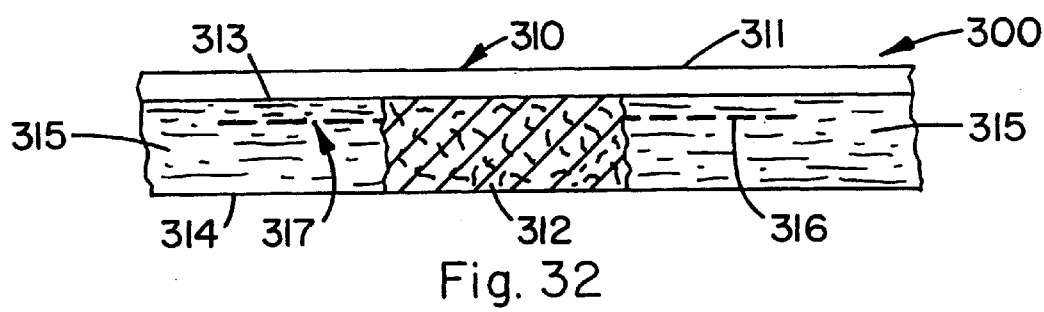
FIG. 32 is a partial side sectional view of another preferred embodiment of an absorbent article utilizing the absorbent structures of the present invention.
Figure 33:
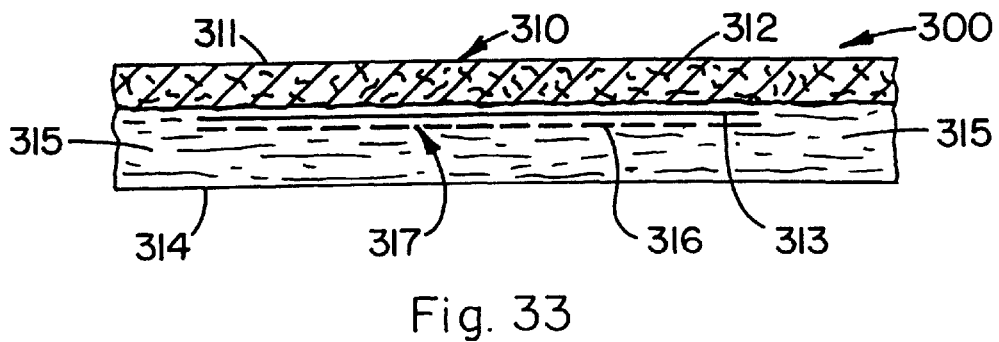
FIG. 33 is a partial side sectional view of still another preferred embodiment of an absorbent article utilizing the absorbent structures of the present invention.

In another embodiment, as shown in FIG. 32, the distribution layer 313 is directly underneath the top sheet 311 and has a length 303. The primary impingement zone 310 comprises a portion of the top sheet 311, a portion of the distribution layer 313 underneath the top sheet, and the TA structure 312 under the distribution layer 313 and just above a back sheet 314. On either side of the impingement zone 310 is the storage core 315. The shielding strip 316 is below the distribution layer 313.

In still another embodiment, as shown in FIG. 33, a TA structure 312 is directly underneath a top sheet 311 along the entire length of the top sheet. A distribution layer 313 is underneath the TA structure 312 and above a shielding strip 316. In this embodiment, there is no specified impingement zone. A storage core 315 is below the shielding strip 316 and above a back sheet 314. The top sheet is insulted with an aqueous fluid, which is subsequently acquired by the TA structure. The aqueous fluid is then desorbed from the TA structure and the distribution layer to the storage core.

The top sheet and the shielding strip may be made of any conventional top sheet material such as perforated polyethylene film or a calendar bonded or a spun bonded top sheet made from polypropylene fiber. The top sheet and shielding strip may also be made from other perforated polymer films and fibers. Preferably, the underside of the top sheet has a lower contact angle with aqueous liquids than the top side of the top sheet. In another preferred embodiment the top sheet is made from an apertured film with cut out portions in the aperture walls to provide spontaneous liquid inversion from the frontside of the top sheet to the backside, as disclosed in U.S. application Ser. No. 545,450 filed Oct. 19, 1995.

The distribution layer is preferably fibers like those disclosed in U.S. Pat. Nos. 5,200,248; 5,268,229 and 5,611,981 and in co-pending U.S. application titled "Bundles of Fibers Useful for Moving Liquids at High Fluxes and Acquisition/Distribution Structures that Use the Bundles" filed Aug. 15, 1997. These fibers may be described as having either (a) a Specific Capillary Volume of at least 2.0 cc/g and a Specific Capillary Surface Area of at least 2000 $cm^2$/g or a Slenderness Ratio of at least 9 and at least 30 percent of intra-fiber channels with a capillary channel width of less than 300 microns or (b) a Specific Capillary Volume of less than 2.0 cctg or a Specific Capillary Surface Area of less than 2000 $cm^2$/g and a Slenderness Ratio of less than 9 or more than 70% of intra-fiber channels with a capillary channel width of greater than 300 microns. Preferably, the fibers described in (b) have a single fiber bulk factor of greater than 4.0. Preferably, the fibers of the distribution layer have a specific surface force, which is mathematically determined by the following equation:

$(P y \cos(\theta a))/d \geq 0.03$ dynes/den, wherein P is the perimeter of the cross-section of the fiber (cm); y is the surface tension of the liquid on the surface (dynes/cm); θa is the advancing contact angle of the liquid on a flat surface having the same composition and finish as the surface of the fiber (as specified in U.S. Pat. No. 5,611,981); yCos(θa) is the adhesion tension of the liquid on the surface of the fiber; and d is the denier of the fiber on which the P was measured. Novel fibers which satisfy this inequality provide large driving forces to move fluids.

The storage core may be fluff pulp, chemically modified fluff pulp, superabsorbent polymer, the PS structures of the present invention, or combinations thereof. The back sheet is typically made of polyethylene film.

The fibers of the present invention can be made by several different processes. However, the following four sequences of steps are preferable for making the novel fibers.
Process Sequence of steps
1. Spin, cut, shrink, lube, package
2. Spin, shrink, lube, cut, package
3. Spin, draw, cut, shrink, lube, package
4. Spin, draw, shrink, lube, cut, package The spin step means conventionally extruding molten polymer through apertures in a spinnerette forming shaped fibers. When the molten polymer is poly(ethylene terephthalate) the extrusion is at a temperature of about 270 to 300° C. The viscosity of the molten polymer exiting the aperture is preferably between 400 to 1000 poise. The spin step also includes cooling the extruded polymer to form a fiber having an as spun shape, lubricating the fiber, and then transporting the fiber. The preferred transporting (spinning) speeds are between 500 and 3500 meters per minute (m/min). Higher spinning speeds may result in the onset of crystallization in the extruding fiber. Crystallization reduces the ability of the fiber to shrink in the subsequent shrink step and thereby inhibits the formation of the structural distortions. Preferably, the spinning speeds are from 1000 to 1500 m/min and 2500 to 3200 m/min depending on the polymeric material used. Obviously cross-section preservation and amorphous orientation differences within a cross-section are important during the spinning of these fibers. Typically, relatively low melt temperatures, relatively high molecular weight polymers, relatively high quench rates and possible melt surface tension reduction are used to produce the desired shapes and the amorphous orientation differences.

The cut step means conventionally cutting the fibers. The cut lengths of the novel fibers of the present invention are short as compared to the conventional cut lengths of staple PET fibers, typically one and one half inches. The lengths of the cut novel fibers are from 2 to 37 millimeters (mm).

The final lengths of the novel fibers are not necessarily the lengths of the fibers during intermediate steps in the manufacturing process. For example, in the shrink-cut processes (i.e., in the process involving sequential steps of first shrinking the fibers and then cutting the fibers), the fibers are cut to the desired lengths of between 2 and 37 mm. However, in the cut-shrink processes (i.e., in the process involving sequential steps of first cutting the fibers and then shrinking the fibers), the fibers are cut to a longer length than the desired length and then shrunk to the desired length.

The shrink step occurs by subjecting the as spun fiber or a drawn fiber to an environment having a sufficient temperature to effect shrinking of the fiber to a denier of at least 5 percent, preferably 25 percent, greater than the denier prior to shrinking. The shrinking may be done as a modification of a conventional fiber staple process. The shrink step differs depending on whether the process is either shrink-cut or cut-shrink.

In the shrink-cut process, the novel fibers are preferably formed into a tow. The fibers in the tow are then shrunk. The tow is delivered to the shrinking environment at a first speed and removed from the environment at a second speed, which is slower than the first speed. For example, a heated water bath at a temperature of between 70 and 100° C. may be used to shrink the fiber. The fiber is constrained at both ends of the bath by rolls or drums so that the fiber cannot freely rotate. This shrink process is called rotationally constrained shrink. Shrinking the tow in steam or in a hot oven is also possible. The take-up roll that pulls the fiber out of the shrinking region has a lower surface speed than the feed roll delivering the fiber to the heated shrinking region. This difference in delivery and take-up speeds allows the fiber to shrink in the heated shrinking region.

In the cut-shrink process, the cutting of the novel fibers is performed before the shrinking of the fibers. In this process, which is typically called three-dimensional free shrink, the fibers are not constrained during the shrink process. The shrinking may be performed by immersing the cut fibers in an environment suitable to effect shrinking, such as water, hot air, or steam. The cut-shrink process is particularly suitable for high-speed operations on the order of between 2000 and 3500 meters per minute. The spinning, cutting, and shrinking are consecutively and continuously done. For example, a cut shrink process could be designed to provide spinning speeds of about 3000 meters per minute with correspondingly high rates of cutting and with the shrinking done in a high velocity turbulent hot air chamber with a residence time of 1 to about 30 seconds. As the shrunk fiber passes out of the turbulent hot air chamber, the shrunk fiber falls into a bale for packaging and shipment.

In an alternative cut-shrink process, the shrinking step does not occur immediately following the cutting step. For example, the product from the continuous spinning-cutting process can be used to feed a paper making machine. The step of shrinking can take place at the location of the paper making machine. For this alternative example, it is preferred that the packaged material is in the form of rolled sheets.

The lube step means applying a surface finish to the shrunk fiber. Often the surface finish applied in the spinning step is removed during the shrinking step and another application is necessary. Any conventional finish application process may be used. Examples include applying the surface finish using spray booths, lube rolls, metered tips, or even a hot water bath as used for shrinking the fibers. The surface finish is preferably a hydrophilic surface lubricant, which reduces the contact angle and/or increases the adhesion tension of an aqueous liquid with a fiber surface.

The drawing step is optional and may be either a conventional tow or filament drawing step of the type used to form staple fibers, but which does not use heat setting. The main purposes of the drawing step are to reduce the denier per filament of the product, to increase the amorphous orientation differences within a given filament cross-section, and to increase the amorphous orientation of the polymer chains along the fiber axis. Thus, by drawing the fiber before shrinking, the shrinking step will tend to maximize SRDF and/or LRDF. The drawing is performed under substantially amorphous retaining conditions so that the necessary distortions occur when the drawn structure is shrunk. Because of the rotational constrained free shrink, the shrink-cut processes tend to give relatively high values of SRDF and relatively low values of LRDF compared to the cut-shrink processes.

Referring now to the drawing, in particular FIGS. 1–29, wherein like reference numerals designate identical or corresponding parts throughout the several views, FIG. 1 shows a generally H-shaped orifice or aperture of a spinnerette at a scale of 20 times the actual size of the orifice. The width W of the aperture is approximately 84 microns. The aperture extends along 4c+4d of the "H" for 179 times the width W of the aperture. The distance between the arms 4b and 4c is 60W. In addition, the base 4e extends from 2a to 2b, which is beyond between the two longest portions of the "H-shape". The length of the cross-bar 4e of the aperture is 71W. Apertures of the shape shown in FIG. 1 are part of the spinnerette I-1083 that was used to form the novel fibers of Example 1.

Figure 2:
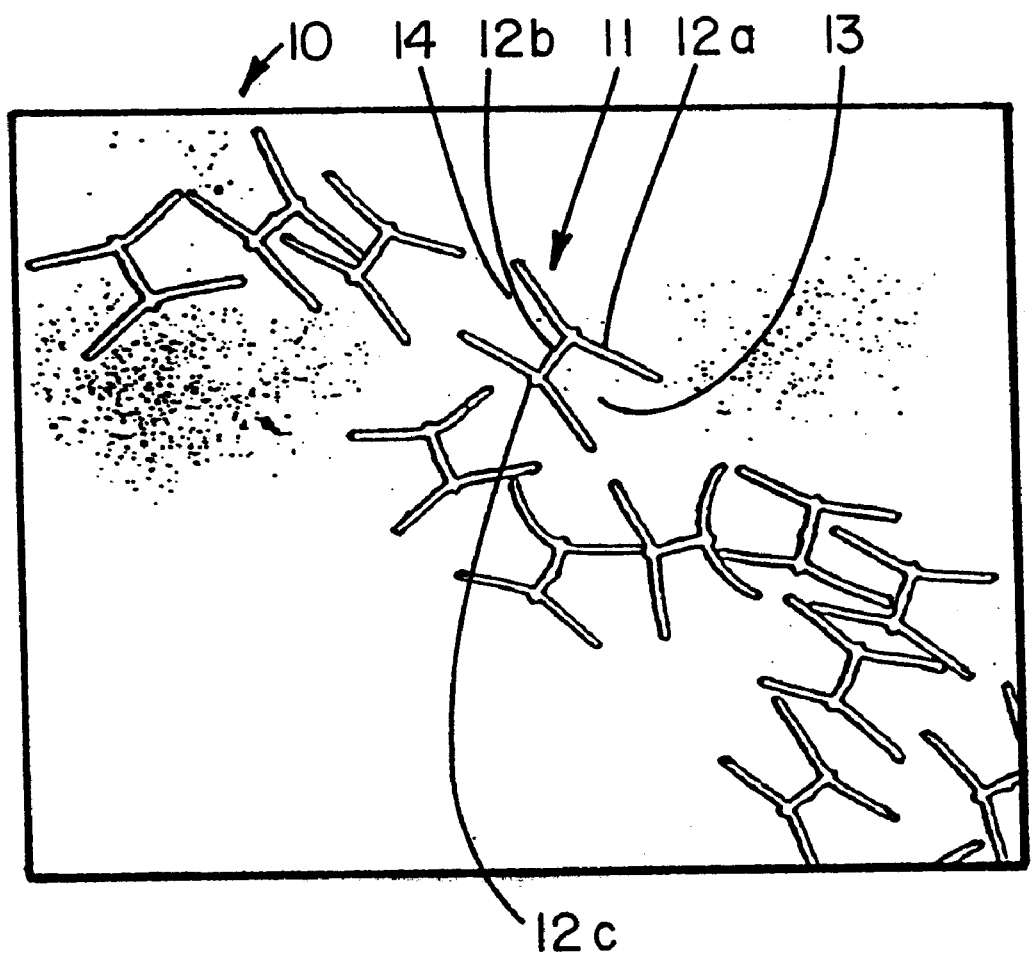
FIG. 2 is a photocopy of a photograph at a magnification of 115 (115X) of an as-spun fiber cross-section of Example 1.

FIG. 2 shows photograph 10 including the cross-sections of generally "H-shaped" as-spun fibers formed from the spinnerette I-1083. Photograph 10 at a magnification of 115 (115X) shows the general H-shaped fiber cross-section 11 which includes four arms such as the arms 12a, a cross-bar 12b connecting to proximal ends of each of the arms, and two projections 12c. The arms 12a of the cross-section 11 are approximately twice as long as the cross-bar 12b and have a length to width ratio of between about 8 and about 12. The channels 13 and 14 are approximately equivalent in width, depth, and area.

Figure 3:
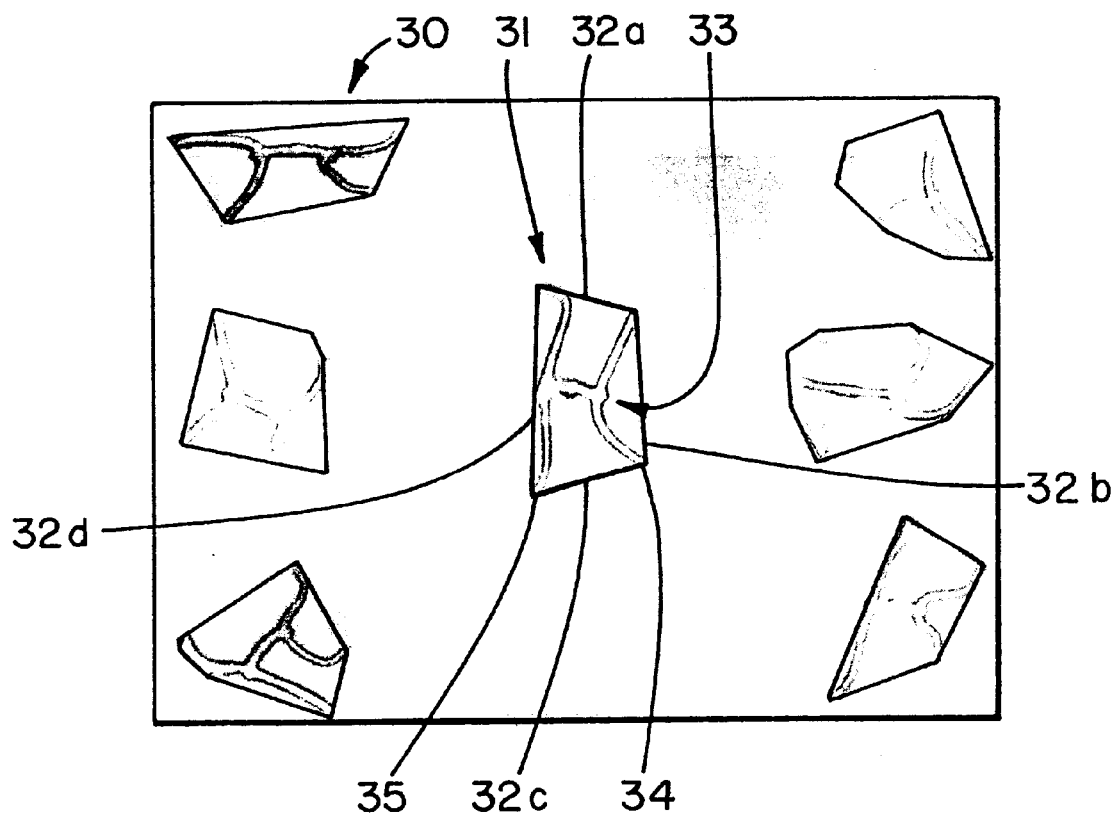
FIG. 3 is a photocopy of portions of seven photographs at 111X, each of which shows a cross-section of the novel fibers of the present invention of Example 1.

FIG. 3 shows seven cross-sections of the novel fibers, each having a distorted "H" shape. Frame 30 delimits the seven cross-sections, which were each taken from photographs at 111X. Cross-section 33 is delimited by a polyhedron 31. The polyhedron 31 includes the segments 32a, 32b, 33c, and 32d, which define the polyhedron 31. Each of the segments 32a–32d is tangent to two points on the surface of the cross-section 33. Adjacent segments form an interior angle interior to the delimited area of the polyhedron 31, that is less than 180°. The segments 32b and 32c meet at the point 34. The segments 32c and 32d meet at the point of 35. FIG. 3 shows that the cross-sections of the novel fibers vary significantly due to the shrinking process leading to the short range distortion factor.

Figure 4A:
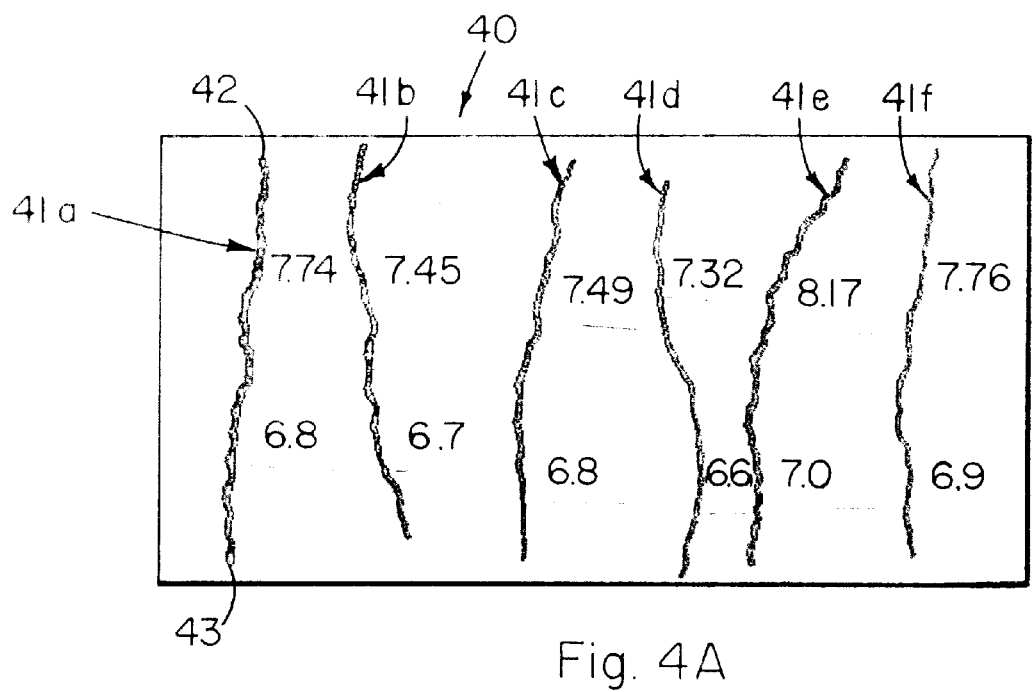
FIG. 4A is a photocopy of a color photograph at 7X of the novel fibers of Example 1.

FIG. 4A shows a photograph 40 at 7X of the novel fibers of 41a–41f of Example 1. There are two rows of numbers in FIG. 4A. The upper row of numbers, including 7.74, 7.45, 7.49, 7.32, 8.17, and 7.76, are the measured values of the length along the backbone of the fibers 41a–41f. The lower row of numbers, including 6.8, 6.7, 6.8, 6.6, 7.0, and 6.9, are the measured values for the diameter of a circle circumscribing each of the fiber 41a–41f. All of the lengths and diameters are in millimeters and are the actual values from the unmagnified novel fibers.

Figure 4B:
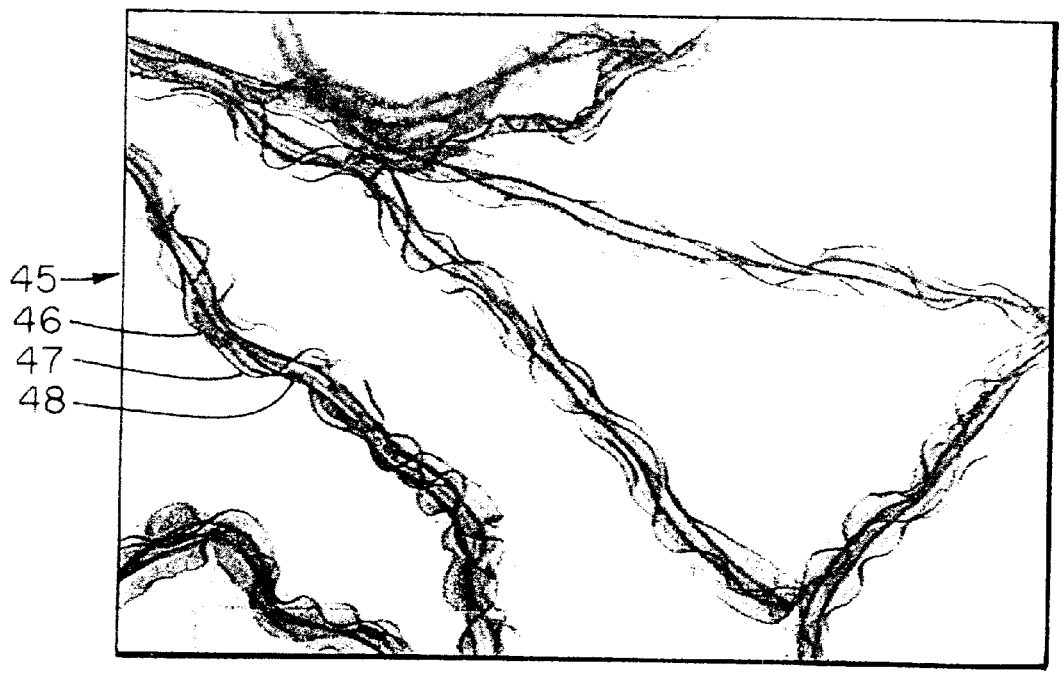
FIG. 4B is a photocopy of a color photograph at 40X of the novel fibers of Example 1.

FIG. 4B shows the photograph 45 at 40X of the novel fibers of Example 1. Polymeric structure 46 includes the arm or wall 47 and the base 48. The azimuthal location of the arm 47 varies along the length of the backbone. The azimuthal angle of the arm 47 changes by 360 degrees along the length of the backbone 48 over a length of the backbone of about 750 microns.

Figure 5:
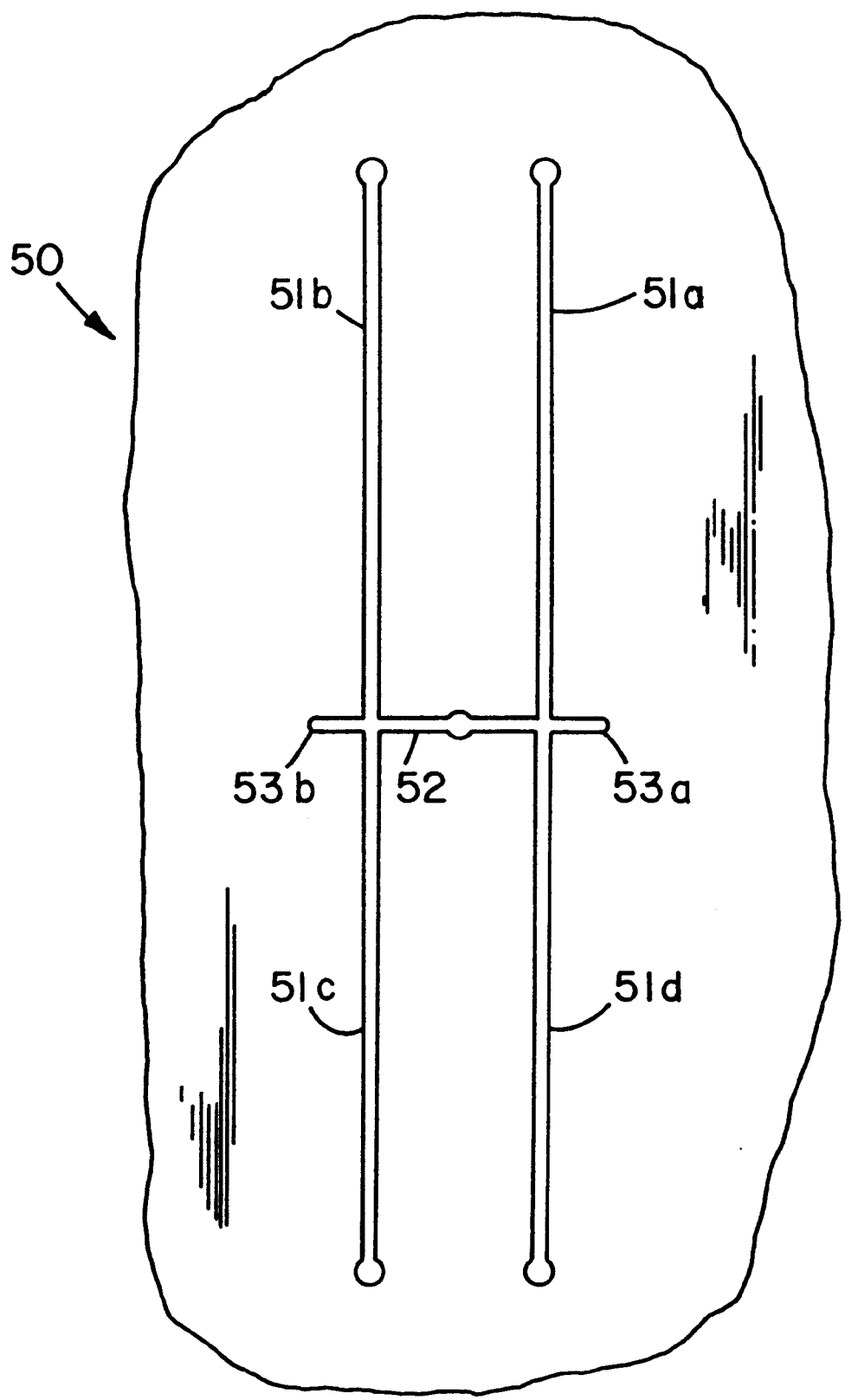
FIG. 5 is schematic in plan view of an H-shaped aperture of a spinnerette identified as I-1042 used in Examples 2 and 19.

FIG. 5 shows a design drawing of an aperture 50 of the spinnerette I-1042 used in Examples 2 and 19. Aperture 50 includes arms 51a, 51b, 51c, and 51d, a cross-bar 52, and projections 53a, 53b. The width W of the aperture 50 is 0.100 mm. Each of the arms 51a–51d has a length of 50W. At the free end of 51a–51d, there is a circular diameter of 1.3W. Each of the projections 53a, 53b has a length of 5W. The cross-bar 52 (including the projections 53a and 53b) is 60W long.

Figure 6:
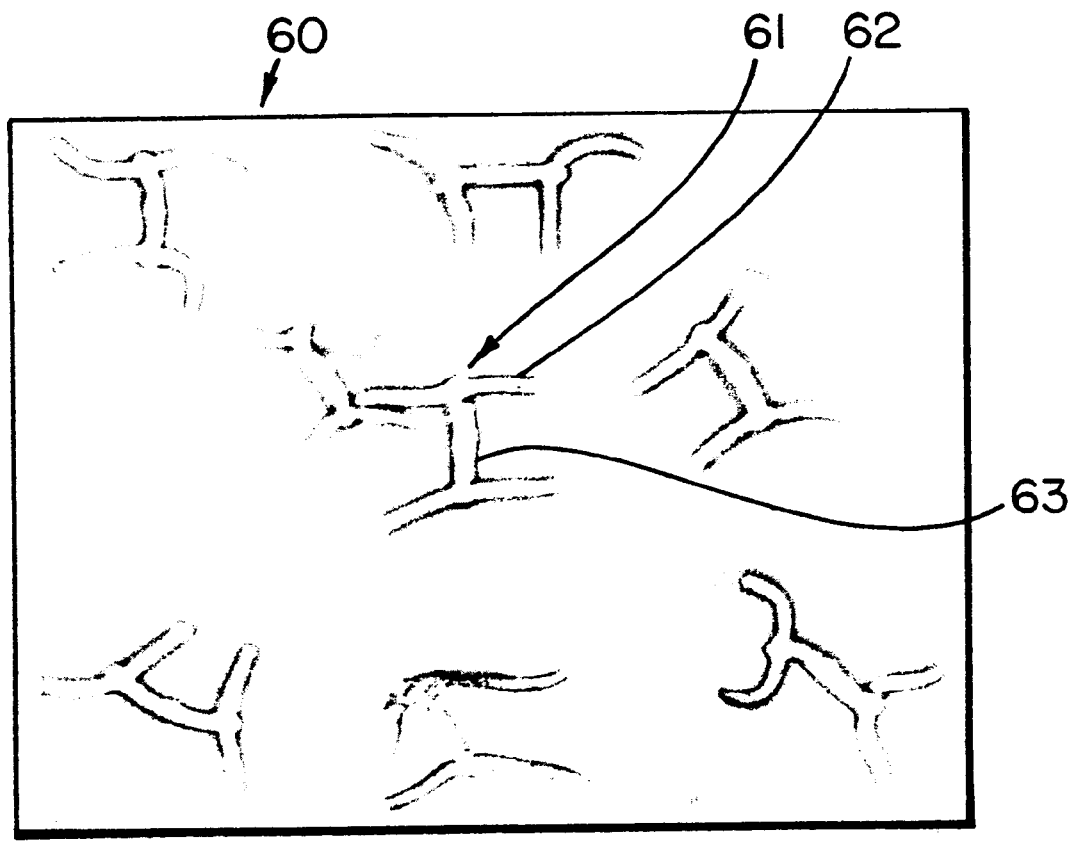
FIG. 6 is a photocopy of portions of seven photographs at 285X, each of which shows a cross-section of the novel fibers of the present invention of Example 2.

FIG. 6 shows a frame 60 delimiting portions of seven photographs at 285X each showing a cross-section of a novel fiber for Example 2. FIG. 6 also shows the cross-section 61 having an arm 62 and a cross-bar 63. The length of the arm 62 is between 30 and 40 microns. The width of the arm 62 is between 5 and 10 microns. The length of the cross-bar 63 is between 25 and 35 microns. The length to width ratio of the arm 62 is approximately 5.

FIG. 7A is a photograph 70 at 80X showing the novel fiber 71 of Example 2. The fiber 71 shows oscillations in the azimuthal location of the walls or arms 72 have a periodicity length 73 which is about 112 microns. The backbone 74 of the fiber 71 is relatively straight over the 112 micron length scale of the oscillations in the azimuthal location of the wall or arm 72.

FIG. 7B is a photograph 78 showing novel fibers of Example 2 at 36X.

FIG. 7C is a photograph 79 at 7X showing three novel fibers of Example 2. The numbers 9.79, 7.18, and 8.0 in FIG. 7C corresponds to the length along the backbone of the fibers shown in the left, center, and right sides of FIG. 7C, respectively. The number 7.7, 6.0, and 6.0 shown in the lower half of FIG. 7C correspond to the diameters of a circle circumscribing the fibers shown in the left, center, and right sides of FIG. 7C, respectively. The fiber 75 has the ends 76 and 77. All of the lengths and diameters are in millimeters and are the actual values from the unmagnified novel fibers.

Figure 8:
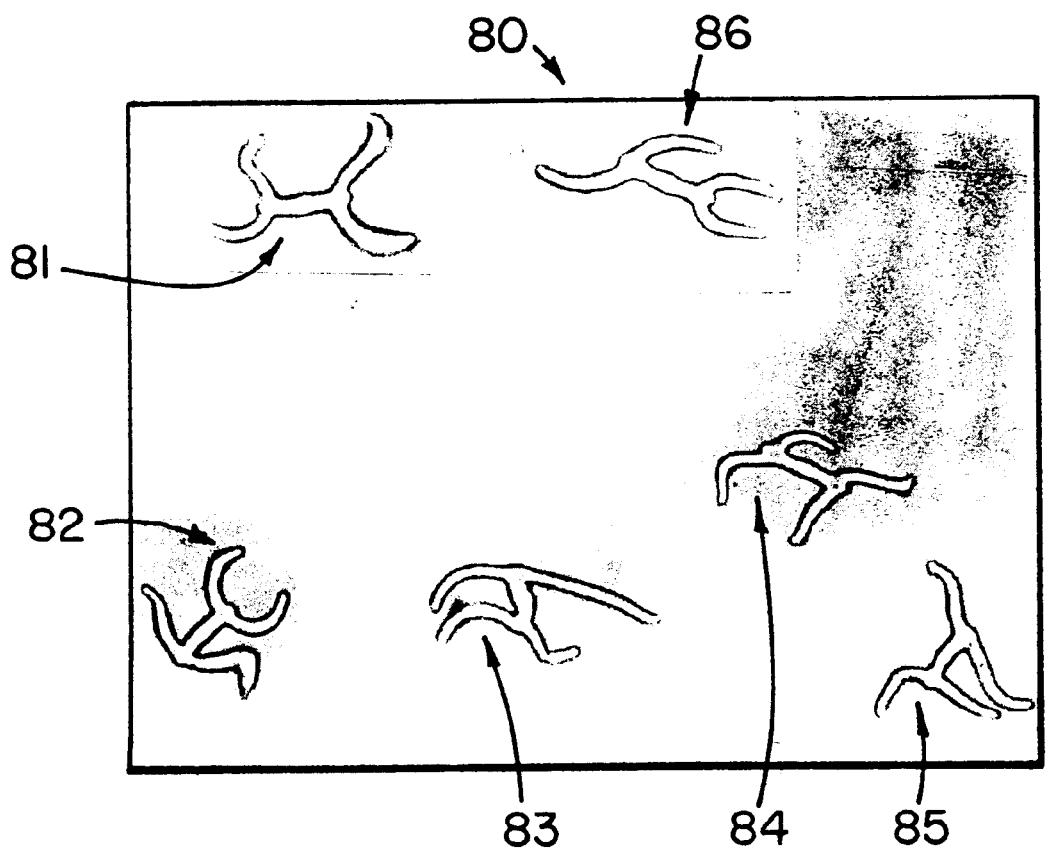
FIG. 8 is a photocopy of portions of six photographs at 285X, each of which shows a cross-section of the novel fibers of the present invention of Example 3.

FIG. 8 is a photocopy of portions of six photographs at 285X, each showing cross-sections of the novel fibers of Example 3. FIG. 8 includes the border 80 delimiting the views of the six cross-sections 81, 82, 83, 84, 85, and 86. The lengths of the arms shown in FIG. 8 vary from about 24 microns to about 50 microns. The widths of the arms shown in FIG. 8 vary from about 7 to about 12 microns. The lengths of the cross-bars connecting arms on opposite sides of the distorted H-shaped cross-sections are between about 14 and about 25 microns.

Figure 9A:
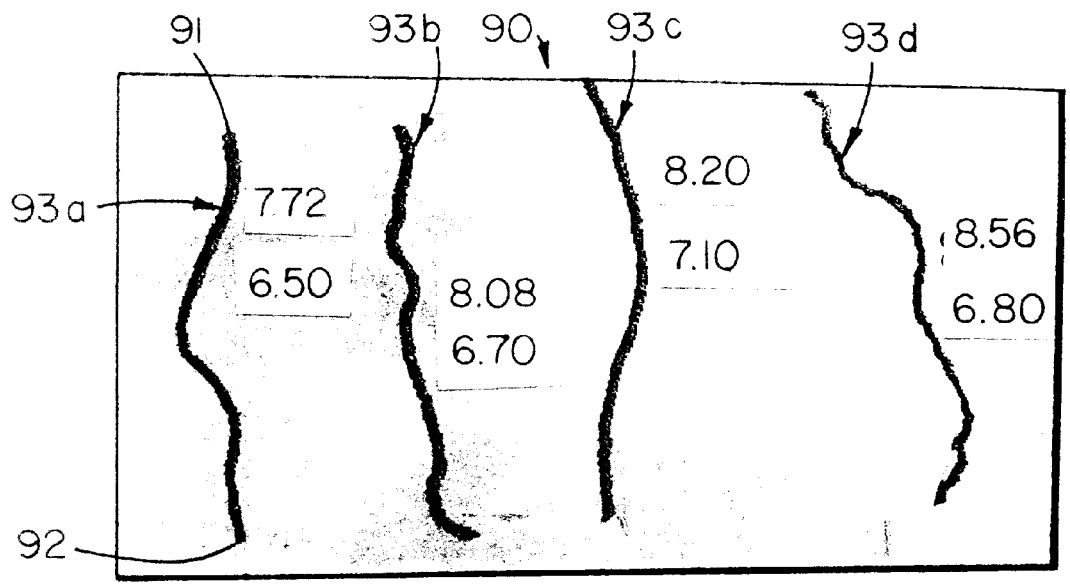
FIG. 9A is a photocopy of a color photograph at 7X of the novel fibers of Example 3.

FIG. 9A is a photograph 90 at 7X showing the novel fibers 93a–93d of Example 3. FIG. 9A shows the numbers 7.72 and 6.50 corresponding to structure 93a, the numbers 8.08 and 6.70 corresponding to structure 93b, the numbers 8.20 and 7.10 corresponding to structure 93c, and numbers 8.56 and 6.80 corresponding to the structure 93d. The upper and lower numbers in FIG. 9A that correspond to each structure are the length along the backbone and the diameter of the circle circumscribing the structure, respectively. All of the lengths and diameters are in millimeters and are the actual values from the unmagnified novel fibers.

Figure 9B:
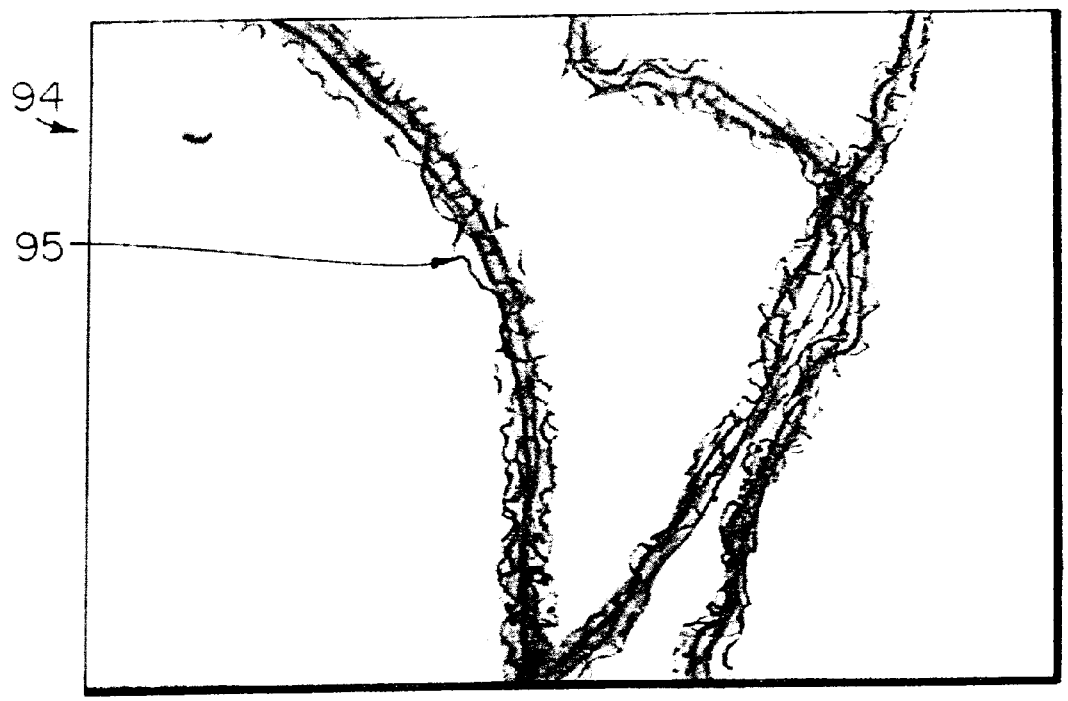
FIG. 9B is a photocopy of a color photograph at 40X of the novel fibers of Example 3.

FIG. 9B is a photograph 94 at 40X showing the novel fibers 95 of Example 3.

Figure 10:
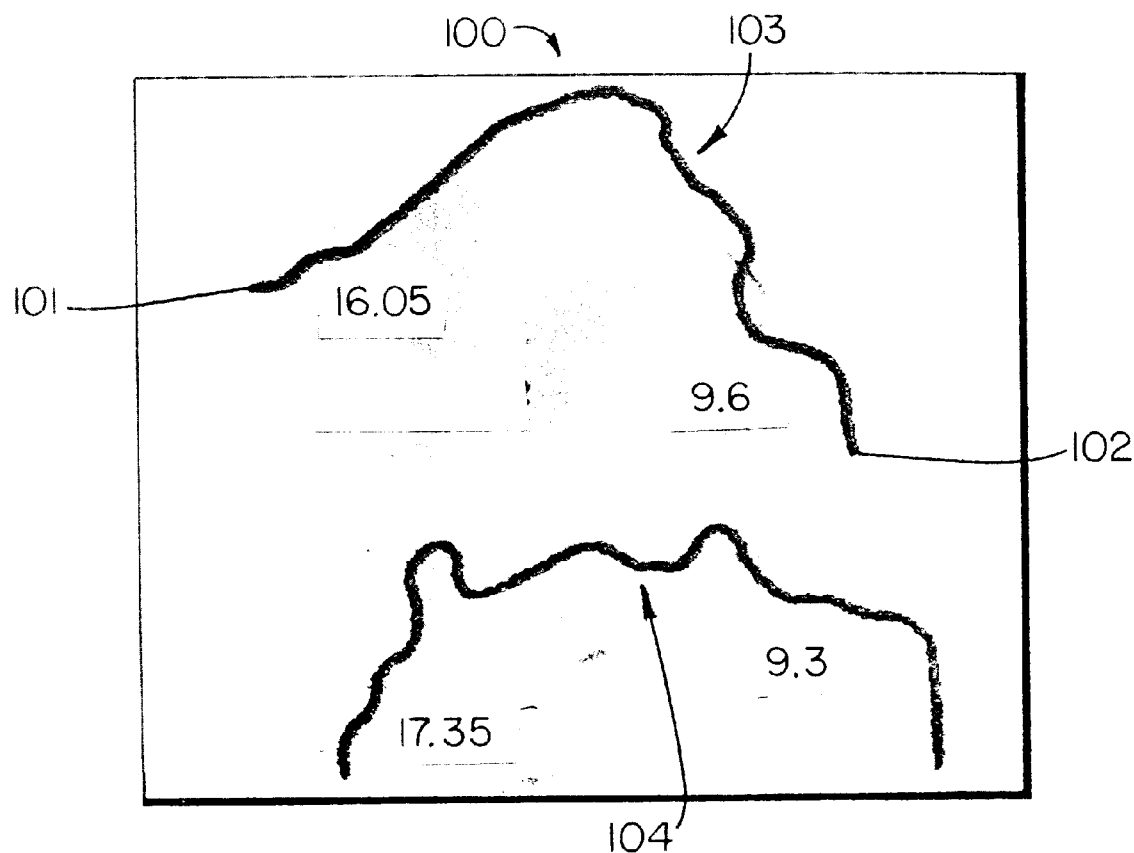
FIG. 10 is a photocopy of a color photograph at 7X of novel fibers of the present invention of Example 4.

FIG. 10 is a photograph 100 at 7X of novel fibers of Example 4. FIG. 10 shows the novel fibers 103 having the ends 101 and 102. FIG. 10 also shows the novel fibers 104. The novel fibers 103 and 104 have the length along their backbones of 16.05 and 17.35 respectively, and diameters of circumscribing circles of 9.6 and 9.3 respectively. All of the lengths and diameters are in millimeters and are the actual values from the unmagnified novel fibers.

Figure 11:
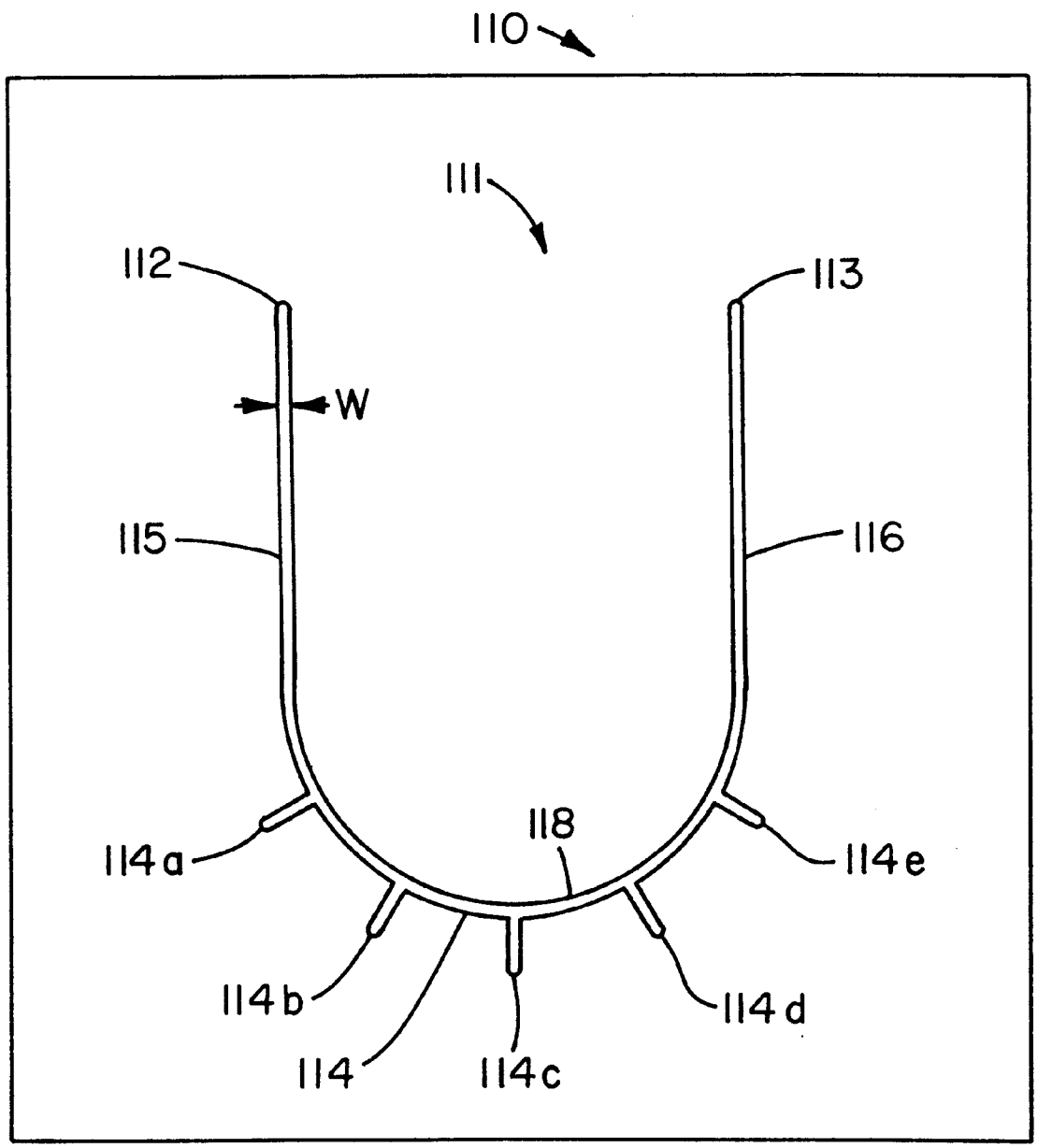
FIG. 11 is a schematic in plan view of a U-shaped aperture of a spinnerette identified as I-1127 used in Examples 12 and 13.

FIG. 11 shows a frame 110 framing a design drawing of an aperture 111 of a spinnerette. The aperture 111 includes the ends 112, 113, the straight extending portions 115,116, and the projecting portions 114a–114e of the circular section 114. The ends 112,113 are circular in shape with a diameter of 1.3W. The aperture 111 includes the inner surface 118 of the extending portions 115,116 and the circular section 114, which defines the channel 117. The width W of the aperture is 0.100 mm. The length of the extending portions 115,116 is each 28.75W. The angles between a normal to the extending portion 116 and the projection 114e is 30°. The angles between each adjacent ones of the projecting 114a–114e is 30°. A radius of curvature of the circular section 114 is 18.4W.

Figure 12:
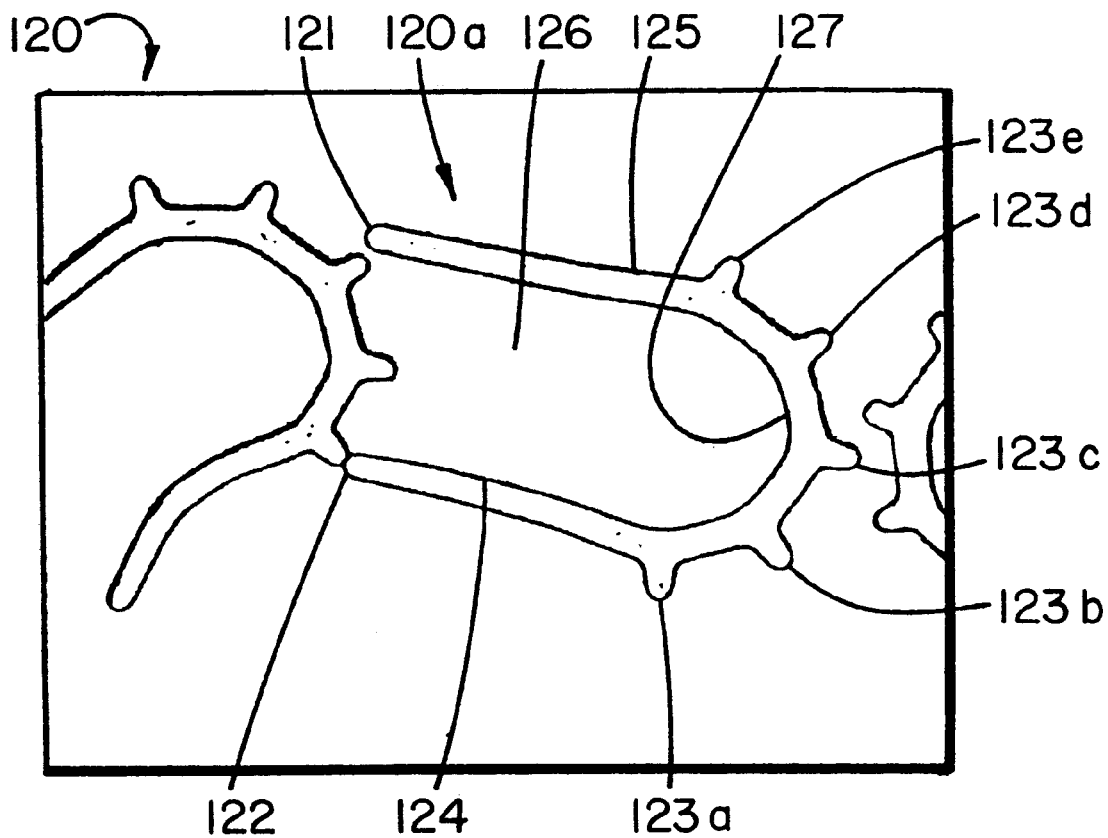
FIG. 12 is a photocopy of a photograph at 464X of an as spun fiber cross-section of Example 12.

FIG. 12 shows a photograph 120 at 464X of fibers in an as spun state, which were spun from a spinnerette having the aperture shown in FIG. 11. The cross-section 120a shown in FIG. 12 has the ends 121,122 from which extend the extending portions 124,125. The cross-section 120a also includes the projections 123a–123e and has the inner surface 127 defining the channel 126. The extending portions 124, 125, are approximately 75 microns longs. The width W of the channel 126 at its mouth is approximately 55 microns. The projecting portions 123a–123e project between 5 and 10 microns. A width of the extending portions 124, 125 at their mid-sections is between 5 and 10 microns.

Figure 13:
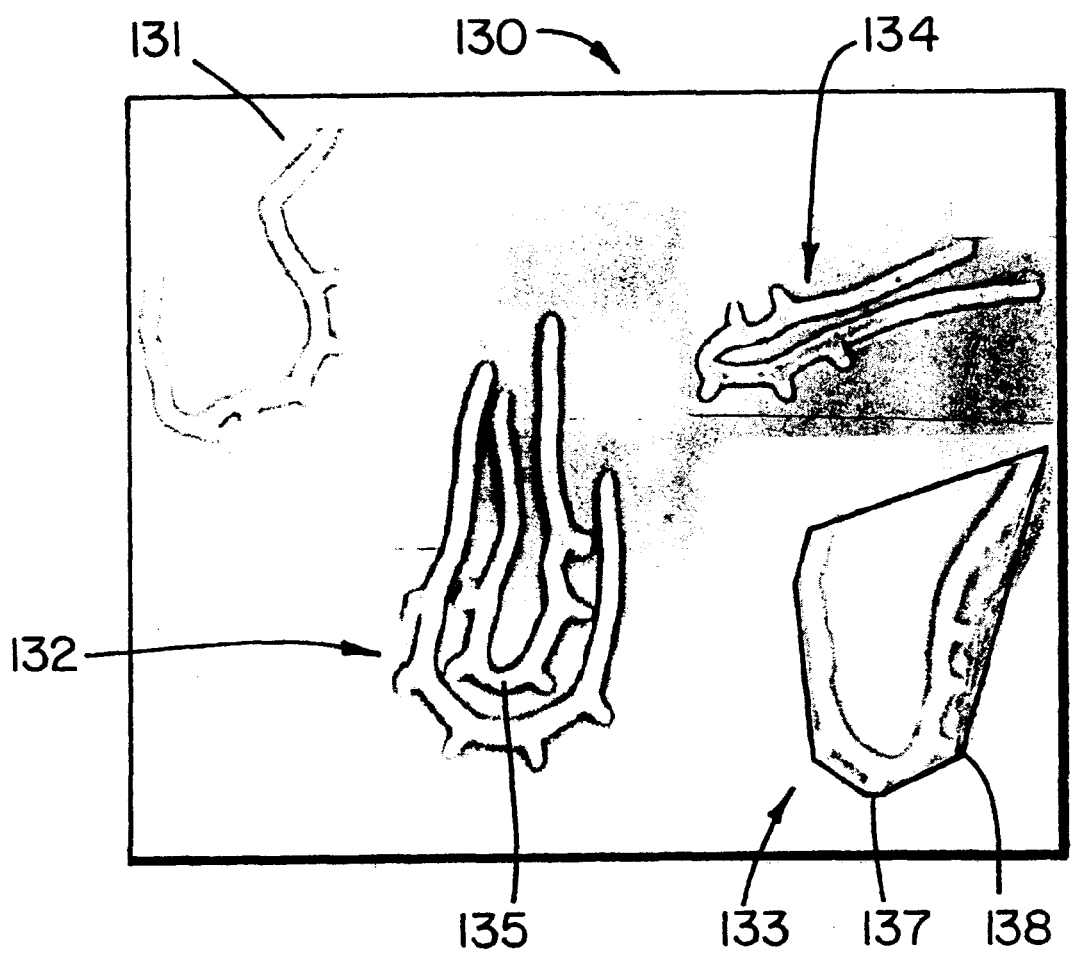
FIG. 13 is a photocopy of portions of four photographs at 285X, each of which shows a cross-section of the novel fibers of the present invention of Example 12.

FIG. 13 shows border 130 delimiting portions of four optical photographs at 285X, each show a cross-section of a novel fiber of Example 12. FIG. 13 shows the cross-sections 131,132,133, and 134. The cross-section 132 actually contains cross-section 135, which is in registration with cross-section 132. Cross-section 131 shows a channel that is wider than the channel of the pre-shrunk fiber shown in FIG. 12. Cross-section 134 shows a channel that is much narrow than the channel of the pre-shrunk fiber in FIG. 12. The cross-section 133 is shown delimited by a polyhedron including segments joining at points 137 and 138. FIG. 13 shows that the morphology of the channel shown in FIG. 12 is highly distorted after the shrink process.

Figure 14:
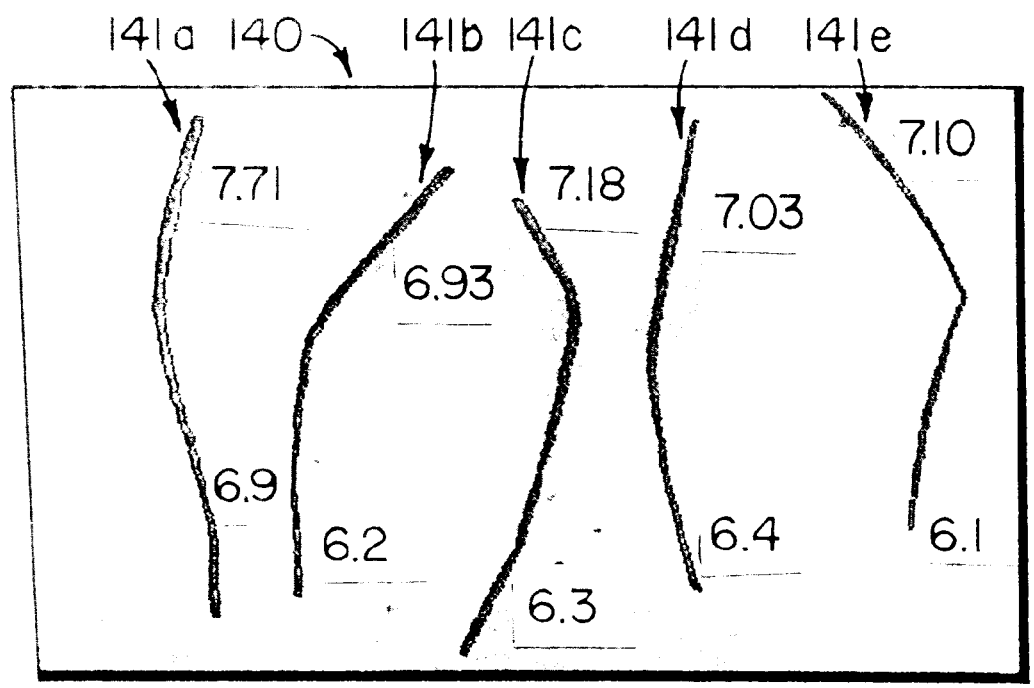
FIG. 14 is a photocopy of a color photograph at 7X of the novel fibers of Example 12.

FIG. 14 is a photograph 140 at 7X of five novel fibers of Example 12. The novel fibers are 141a–141e. The lengths along the backbone of the five fibers are 7.71, 6.93, 7.18, 7.03, and 7.10 millimeters, respectively. The lengths of the circumscribing circles of fibers 141a–141e are 6.9, 6.2, 6.3, 6.4, and 6.1 millimeters, respectively, all as shown in FIG. 14. All of the lengths and diameters are in millimeters and are the actual values from the unmagnified novel fibers.

Figure 15:
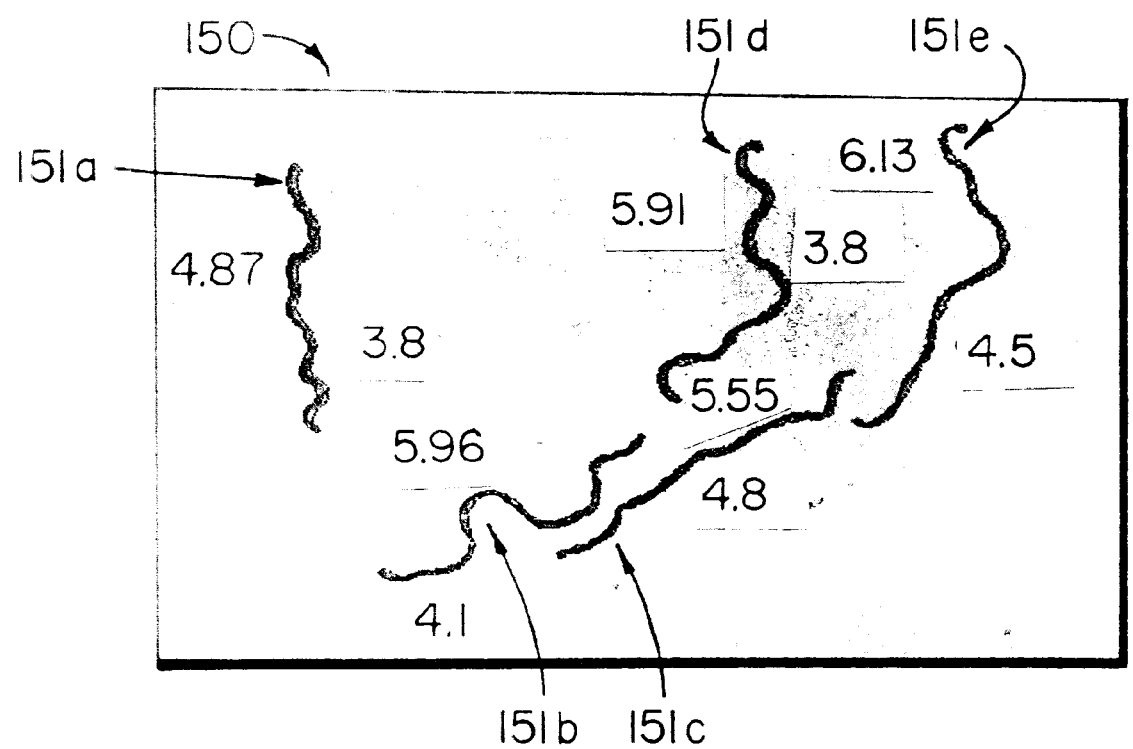
FIG. 15 is a photocopy of a photograph at 7X of the novel fibers of the present invention of Example 13.

FIG. 15 shows a photograph 150 at 7X of novel fibers of Example 13. The novel fibers 151a–151e have lengths along their backbones of 4.87, 5.96, 5.55, 5.91, and 6.13 millimeters, respectively, and diameters of circumscribing circles of 3.8, 4.1, 4.8, 3.8, and 4.5, respectively, all as shown in FIG. 15. All of the lengths and diameters are in millimeters and are the actual values from the unmagnified novel fibers.

Figure 16:
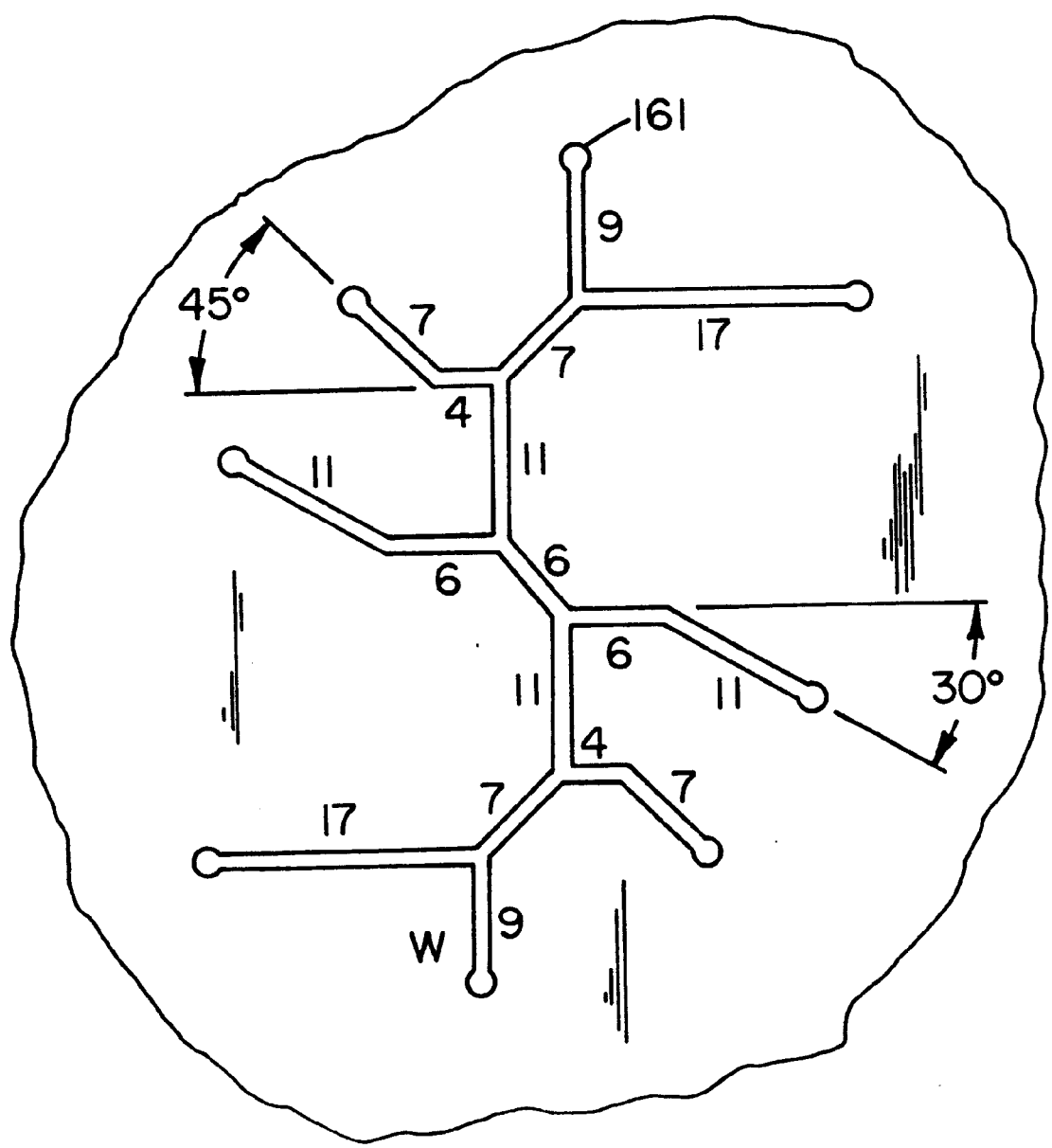
FIG. 16 is a schematic in plan view of an aperture of a spinnerette identified as I-1004 used in Example 14, the shape of the aperture hereinafter called "4DG".

FIG. 16 is a design drawing schematic of an aperture 160 of the spinnerette I-1004. The shape of the aperture 160 is called a "4DG" aperture shape. The numbers along the segments in FIG. 16 indicate the relative length of each segment relative to the width W of the aperture. The width W of the aperture is 0.100 mm. The angles between segments in FIG. 16 are actually angles, not merely illustrative. The free end 161 of each segment is a circular hole with a diameter of 1.5W.

Figure 17:
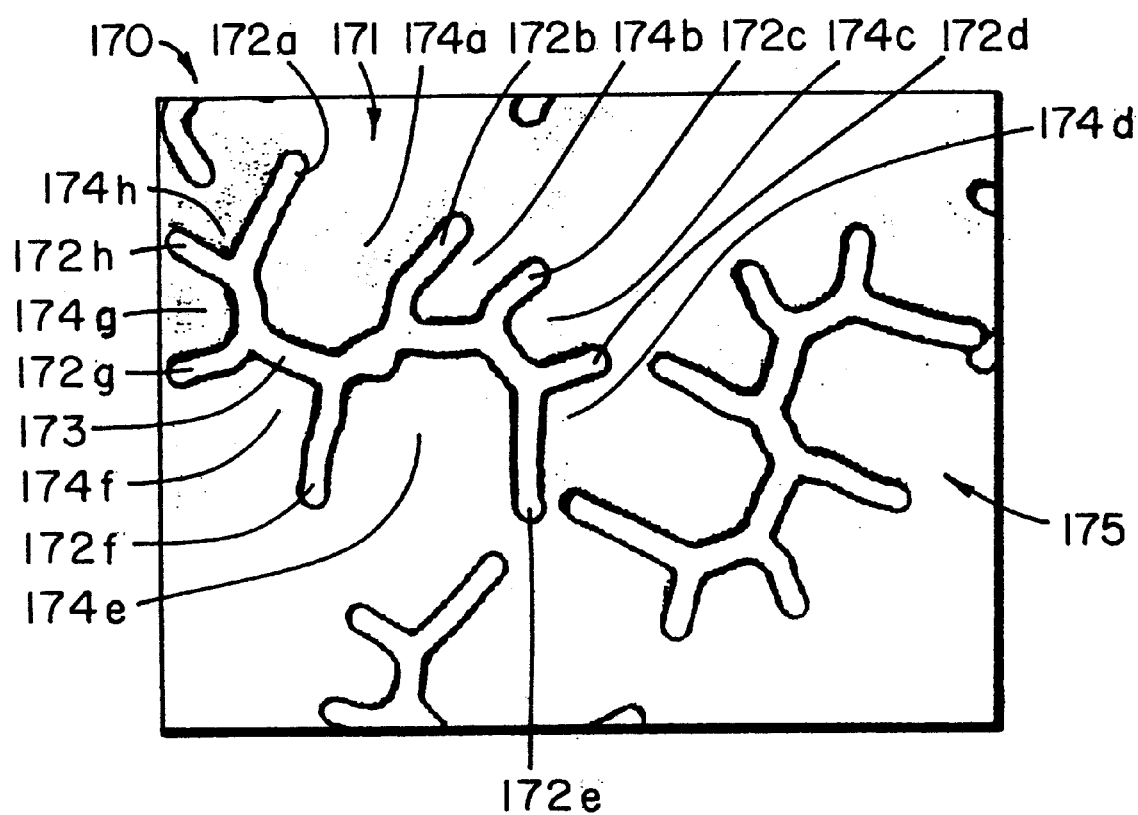
FIG. 17 is a photocopy of a photograph at 464X of an as-spun fiber cross-section of Example 14.

FIG. 17 shows a photograph 170 at 464X of cross-sections of as spun fibers of Example 14 having a cross-sectional shape derived from extrusion from the spinnerette I-1004, the apertures of which have the 4DG shape. The shape of the cross-section shown in FIG. 17 is called the 4DG cross-section shape. The photograph 170 shows the fiber cross-section 171. The cross-section 171 includes walls or arms 172a–172h and a backbone or spine 173 that defines channels 174a–174h. The length of the backbone or spine 173 is about 110 microns. The lengths of the walls or arms forming the channels range from about 15 to about 45 microns. The widths of the channels at their mouth range from between about 20 and about 55 microns. The two channels at the end of the backbone or spine 173 are "V" shaped. The remaining channels are defined by at least two walls and a base. The thickness of each of the arms or walls and the spine are between about 6 and about 10 microns. The two widest channels, channels 174a and 174e are defined by, in addition to the two walls and base, segments at an angle of about 45 degrees relative to the base and that the walls that connect the base to the walls. A better view of the segments connecting the base to the walls of the widest channels appears in the cross-section 175.

Figure 18:
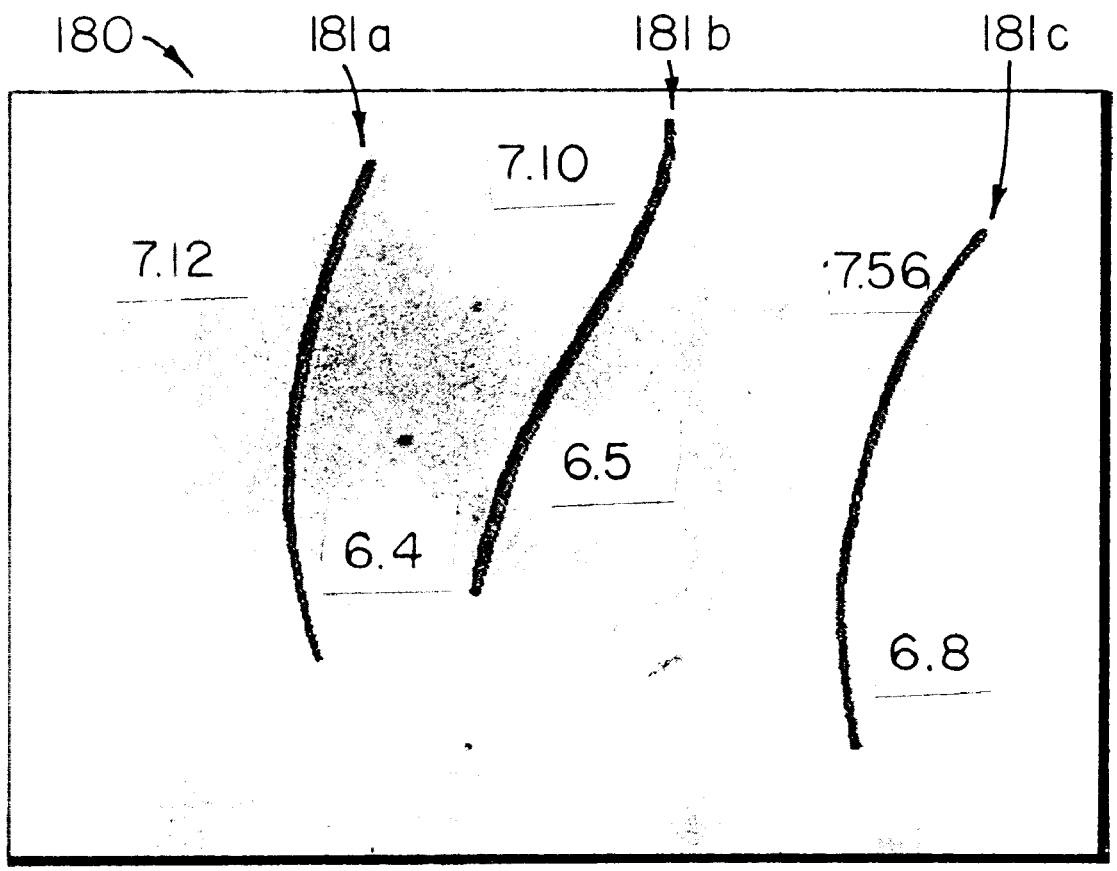
FIG. 18 is a photocopy of a color photograph at 7X of the novel fibers of the present invention of Example 14.

FIG. 18 is a photograph 180 at 7X of the novel fibers 181a, 181b, and 181c of Example 14. The length along the backbone or spine for structures 181a–181c is 7.12, 7.10, and 7.56 respectively, and the diameter of the circumscribing circle for structures 181a–181c is 6.4, 6.5, and 6.8, respectively, all as shown in photograph 180. All of the lengths and diameters are in millimeters and are the actual values from the unmagnified novel fibers.

Figure 19A:
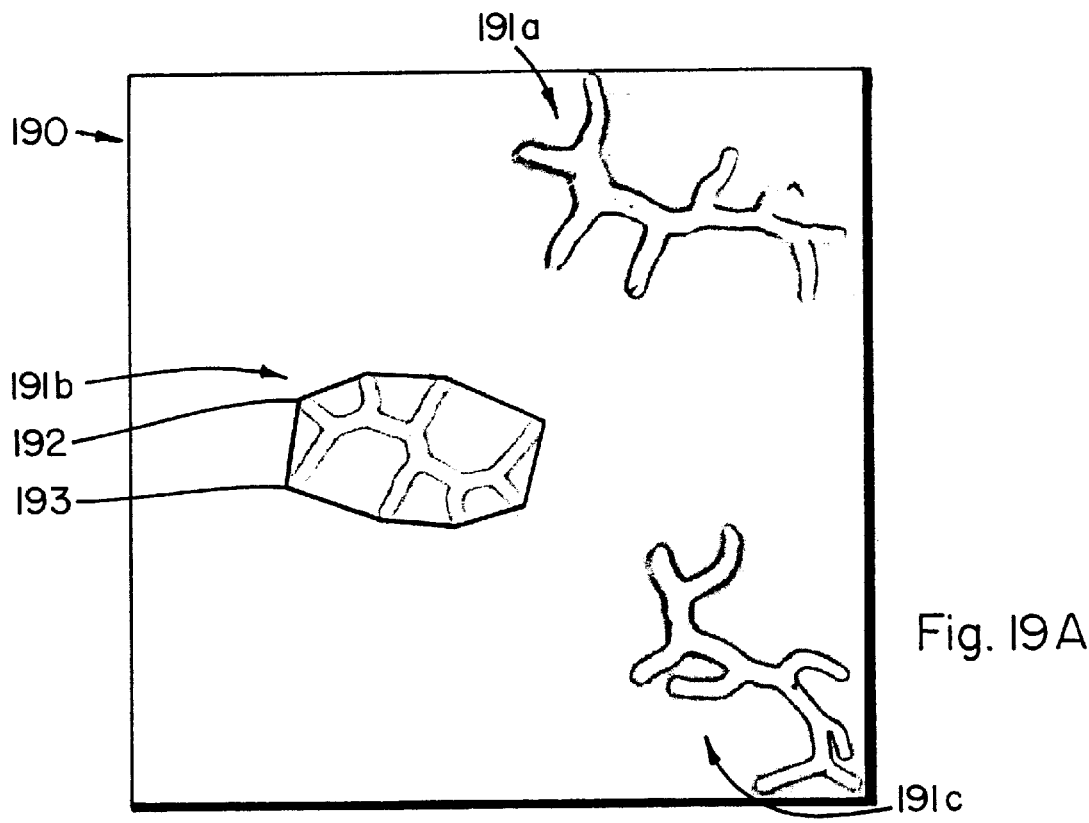
FIG. 19A is a photocopy of portions of three photographs at 285X, each of which shows a cross-section of the novel fibers of the present invention of Example 15.

FIG. 19A includes a border 190 delimiting portions of three photographs at 285X, each showing a cross-section of a novel fiber of 191a, 191b, and 191c of Example 15. Cross-section 191b is enclosed by line segments forming a polyhedron. Two of the lines segments of the polyhedron meet at the point 192 and two of the line segments of the polyhedron meet at the point 193. Each line segment is tangent to two points on the surface of the cross-section. Adjacent line segments form an angle interior to the polyhedron of less than 180 degrees. The crosssection 191a is identified by the number 36. The cross-section 191b is identified by the number 46. The cross-section 191c is identified by the number 2.

Figure 19B:
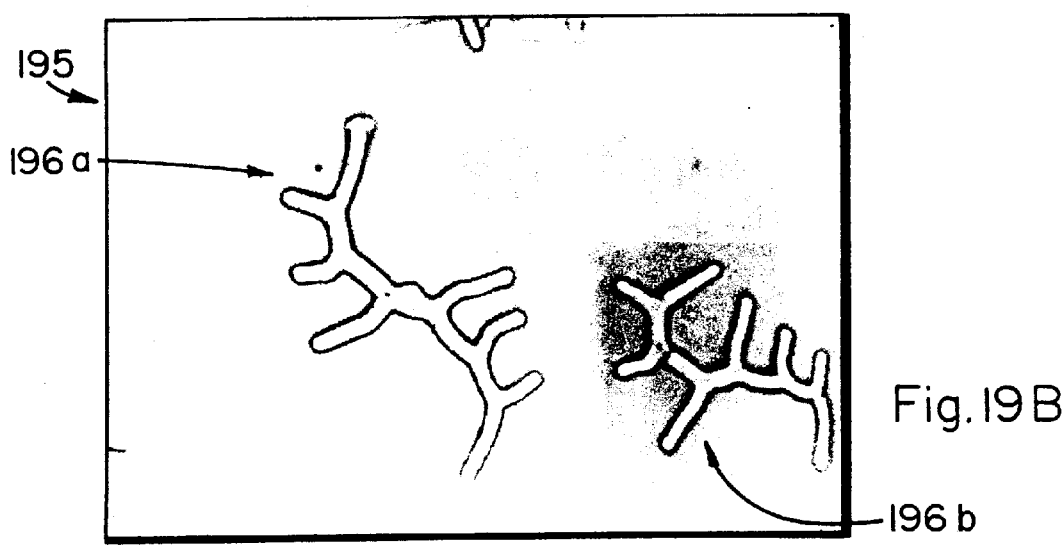
FIG. 19B is a photocopy of portions of two photographs at 285X, each of which shows a cross-section of the novel fibers of Example 15.

FIG. 19B includes a boarder 195 containing portions of two photographs at 285X, each showing one of the cross-sections 196a and 196b of the novel fibers of Example 15. The cross-section 196a is identified by the number 35. The cross-section 196b is identified by the number 12.

Figure 20:
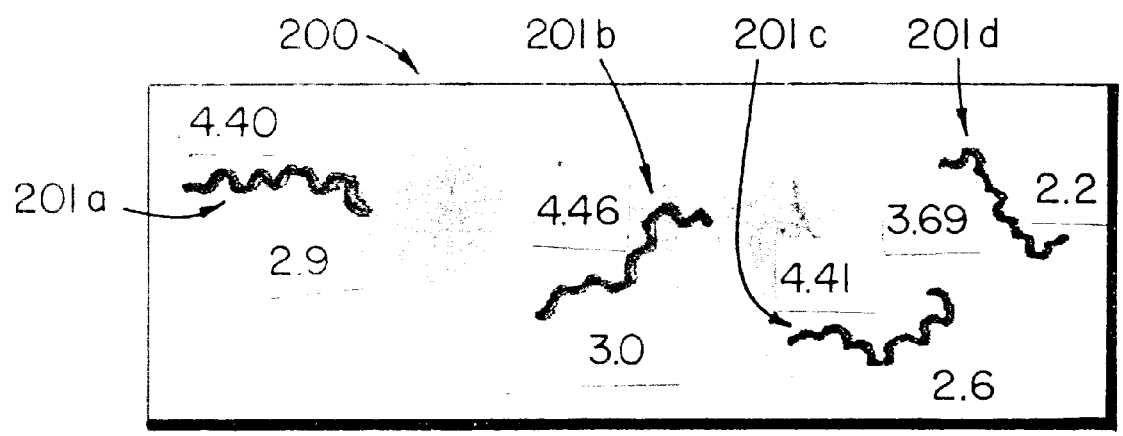
FIG. 20 is a photocopy of a color photograph at 7X of the novel fibers of Example 15.

FIG. 20 shows a photograph 200 at 7X of the novel fibers 201a–201d of Example 15. The length along the backbone or spine of structures 201a–201d is 4.40, 4.46, 4.41, and 3.69 mm respectively. The diameter of the circle circumscribing the structures 201a–201d is 2.9, 3.0, 2.6, and 2.2, respectively, all as shown in photograph 200. All of the lengths and diameters are in millimeters and are the actual values from the unmagnified novel fibers.

Figure 21A:
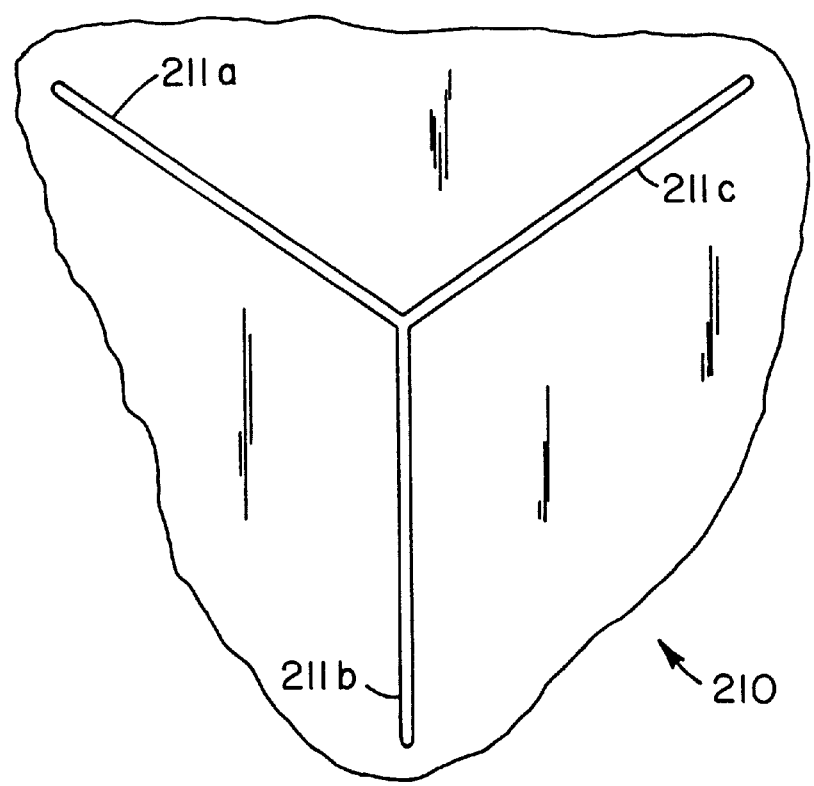
FIG. 21A is a schematic in plan view a Y-shaped aperture of a spinnerette identified as I-1195 used in Example 20.

FIG. 21A shows a schematic in plan view of an Y shaped aperture design 210 for the apertures of the spinnerette 215 (see FIG. 21B) identified as I-1195. The aperture 210 includes arms 211a, 211b, and 211c. The arms 211a and 211c define an angle of 110 degrees between them. The arms 211a and 211b define an angle of 125 degrees between them. The arms 211b and 211c define an angle of 125 degrees between them. The width W of the aperture is 0.067 mm. The lengths of each of the arms of the aperture 210 are 150W.

Figure 21B:
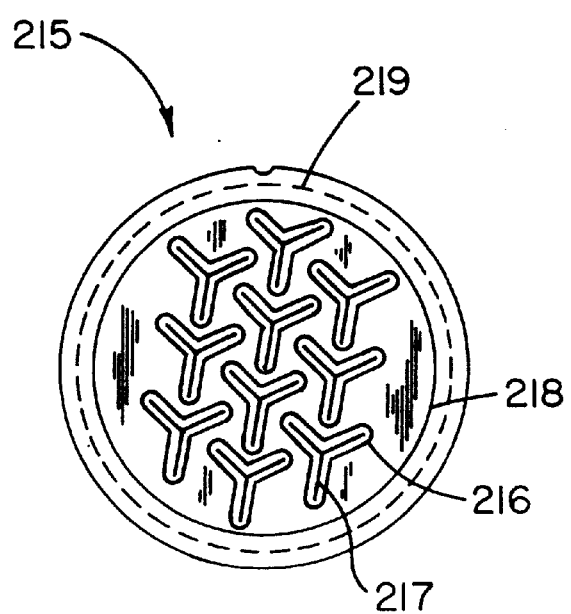
FIG. 21B is a schematic plan view of a face of the spinnerette I-1195 showing a plurality of the Y-shaped apertures.

FIG. 21 B is a schematic plan view of the spinnerette 215 identified as I-1195 showing the ten Y shaped apertures 210. The face 218 of the spinnerette includes the Y shaped aperture 217 and the bores 216 in spinnerette 215. Delimiting the face of the spinnerette in the plan view in FIG. 21b is the flange surface 219 of the spinnerette 215.

Figure 22:
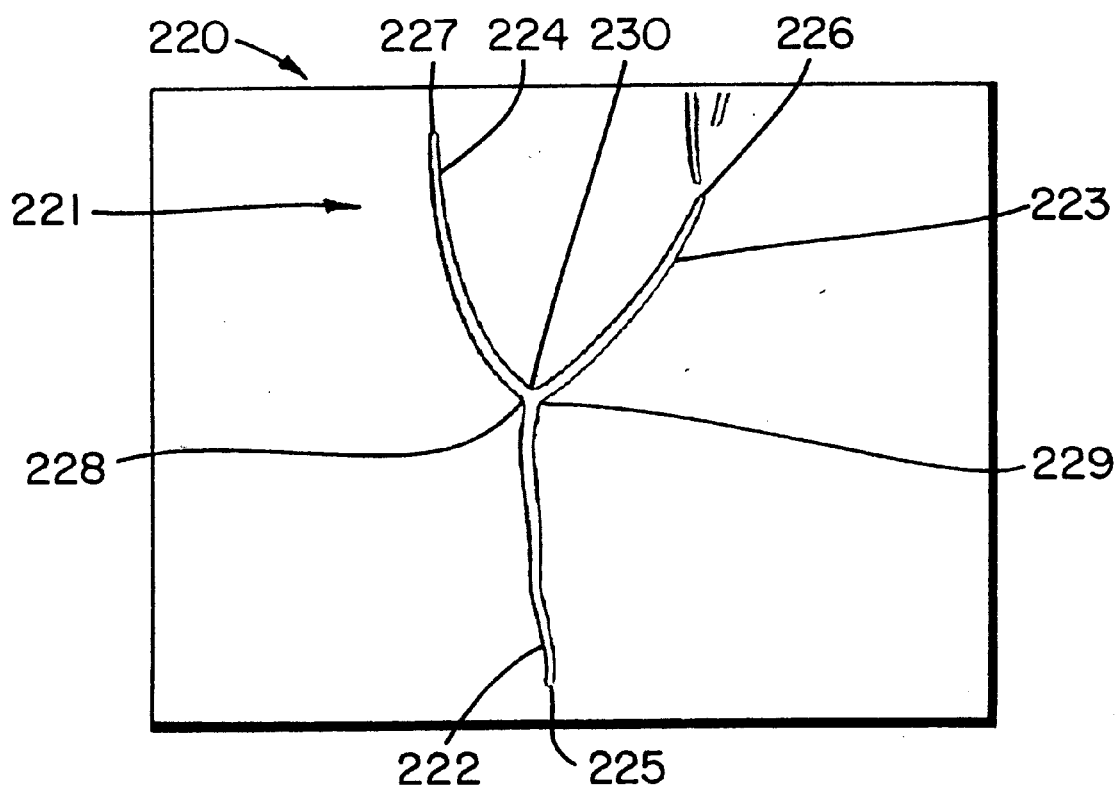
FIG. 22 is a photocopy of a photograph at 115X of an as-spun fiber cross-section of Example 20.

FIG. 22 shows the photograph 220 at 115X showing the cross-section 221 of an as spun fiber of Example 20. The cross-section 221 includes the arms 222, 223, and 224, which have distal tips 225, 226, and 227. The arms 224 and 222 meet at the vertex 228 and define an angle of greater than 120 degrees. The arms 222 and 223 meet at the vertex 229 and define an angle of greater than 120 degrees. The arms 223 and 224 meet at the vertex 230 and define an angle of less than 120 degrees. The length of the arms range between about 216 and about 310 microns. The width of the arms at the mid section range between about 15 and about 20 microns. The arms 223 and 224 have a slight curvature concave towards one another. However, the alignment of each arm does not vary by more than 60 degrees. That is, a line that is best aligned along any 100 micron long section of either of the arms 223, 224 defines an angle of less than 60 degrees with any other line aligned along another 100 micron long section of the same arm.

Figure 23:
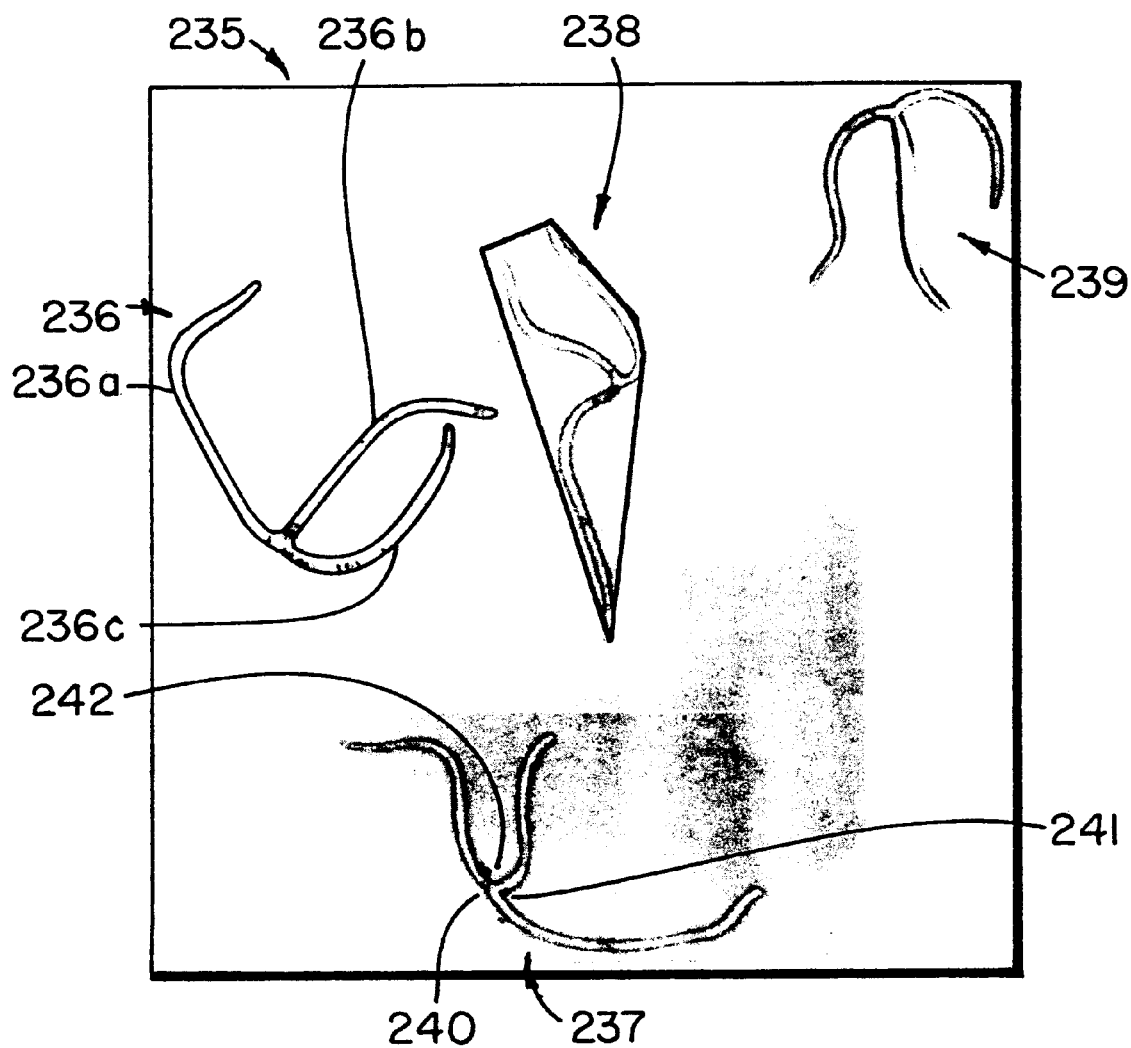
FIG. 23 is a photocopy of portions of four photographs at 115X, each of which shows a cross-section of the novel fibers of the present invention of Example 20.

FIG. 23 shows a border 235 delimiting portions of a four photographs at 111X, each showing one of the novel fibers 236, 237, 238, and 239 of Example 20. Cross-section 236 shows three arms 236a, 236b, and 236c. The angle defined by the portions of the arm 236a and 236c where those arms join another is approximately 180 degrees. The remaining two angles defined by the portions of the arms 236a, 236b, and 236c where those arms join are each less than about 90 degrees. The lines aligned with the arm 236a and 236c along 100 micron sections thereof vary by more than 60 degrees. Cross-section 237 includes arms that define the vertices 240, 241, 242. The arms of the vertex 238 define an angle of about 180 degrees. The arms of the vertices 239, 240 define angles less than about 120 degrees. Cross-section 238 is shown enclosed in a polyhedron. The lengths of the arms of the cross-sections shown in border 235 are between about 210 and 350 microns. The widths of the arms of the cross-section shown in border 235 at the mid sections of the arms vary between about 8 and about 16 microns.

Figure 24:
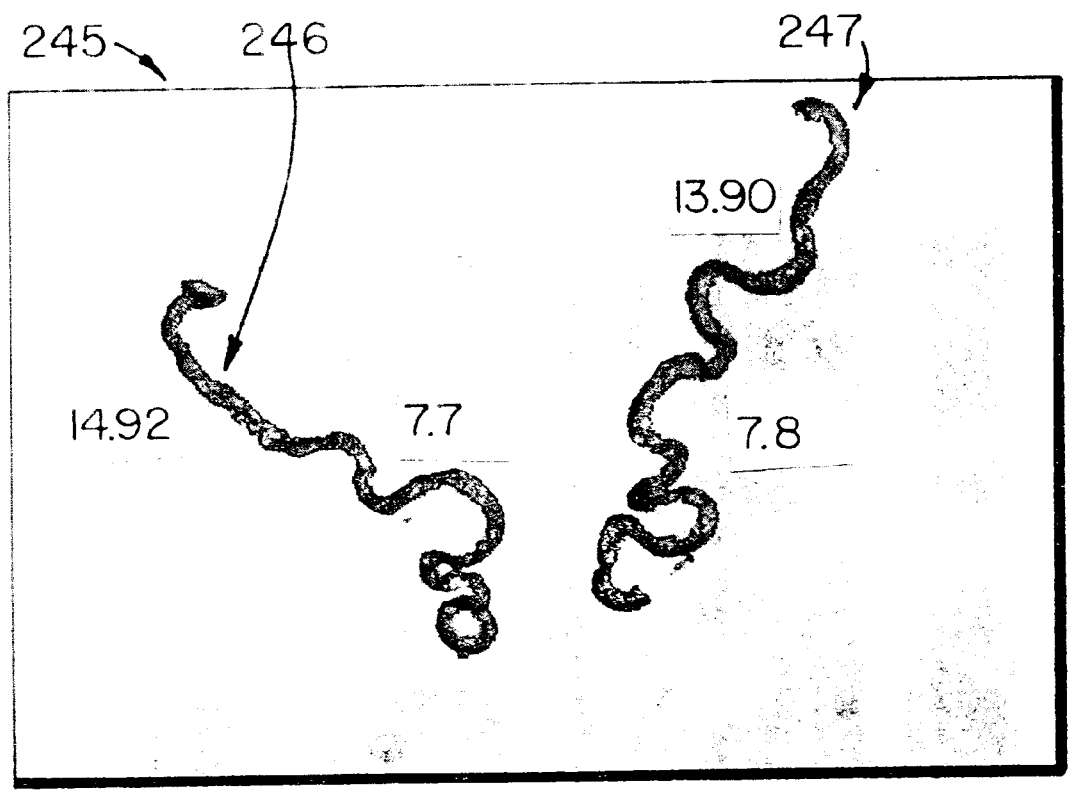
FIG. 24 is a photocopy of a color photograph at 7X of novel fibers of Example 20.

FIG. 24 shows a photograph 245 at 7X of the novel fibers 246 and 247 of Example 20. The length along the backbone or spine of structures 246, 247, are 14.92 and 13.90, respectively. The diameters of the circumscribing circles of structures 246 and 247 are 7.7 and 7.8 respectively. All of the lengths and diameters are in millimeters and are the actual values from the unmagnified novel fibers.

Figure 25:
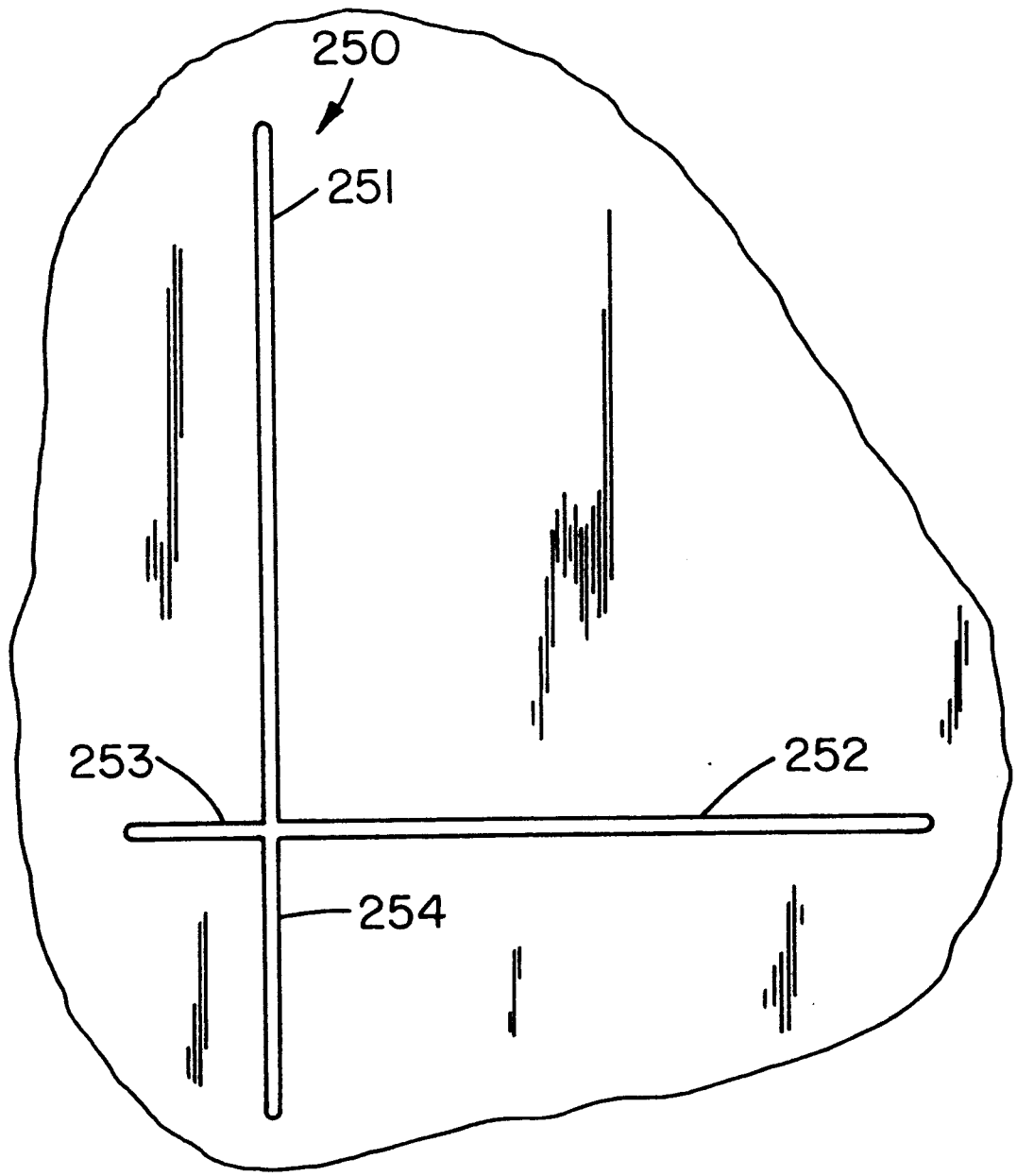
FIG. 25 is a schematic in plan view of an aperture of a spinnerette identified as I-1198 used in Example 21.

FIG. 25 is a schematic 250 of a design drawing of an aperture in the spinnerette identified as I-1198 used to make the novel fibers of Example 21. The aperture 250 includes the two short arms 253 and 254 and the two long arms 251 and 252. The width W of the aperture is 0.067 mm. The length of arm 253 is 40W. The length of arm 254 is 80W. The length of the arm 251 is 196W. The length of the arm 252 is 183W. The arms radiate from a common point at 90 degrees relative to one another. The two short arms form an angle of 90 degrees and the two long arms form an angle of 90 degrees.

Figure 26:
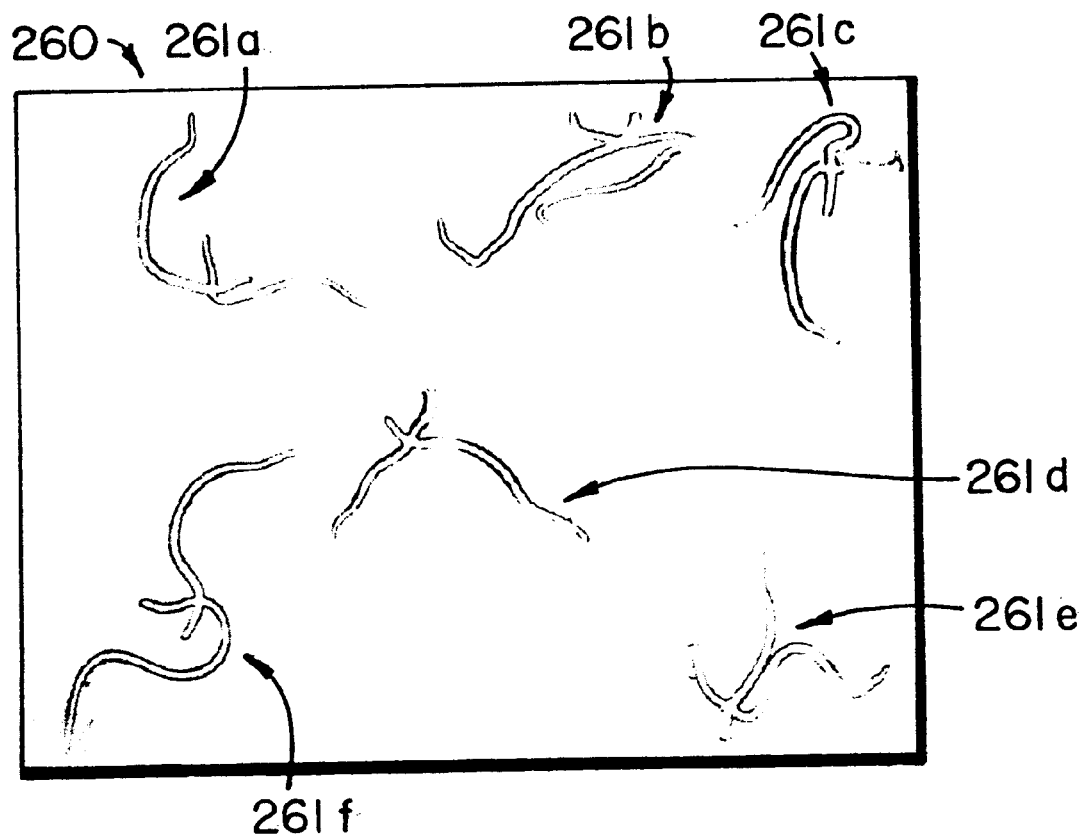
FIG. 26 is a photocopy of portions of six photographs at 115X, each of which shows a cross-section of the novel fibers of the present invention of Example 21.

FIG. 26 is a photocopy of portions of six photographs at 115X, each showing one of the cross-sections 261a–261f of a novel fibers of Example 21. Each cross-section contains two long arms and two short arms. The lengths of the short arms vary from between about 35 and about 70 microns. The lengths of the long arms vary from between about 130 and 340 microns. The width of the long arms at their mid sections vary between about 8 and about 16 microns. The two short arms are adjacent to one another with no long arm intervening between them. All four arms extend from a common point in the cross-sections, which means that all four arms extend from a common backbone or axis along the length of the structure.

Figure 27A:
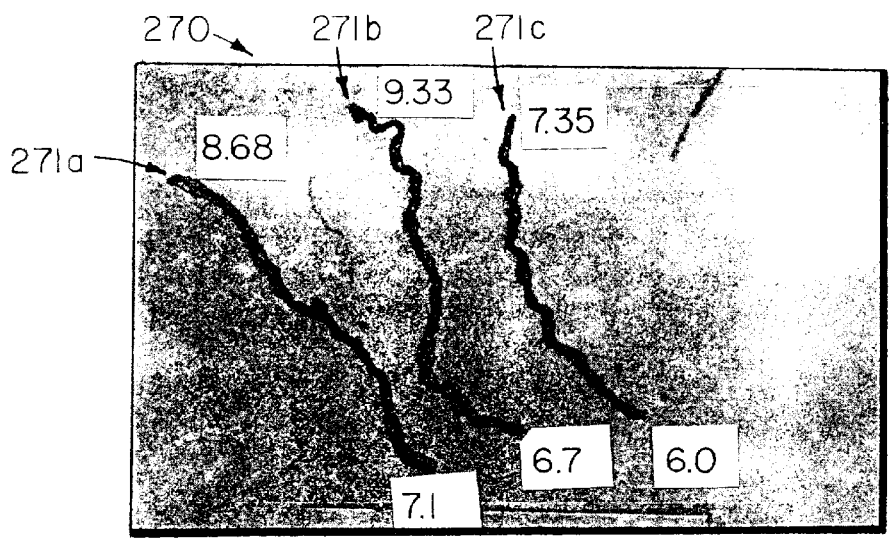
FIG. 27A is a photocopy of a color photograph at 7X of the novel fibers of Example 21.

FIG. 27 shows a photograph 270 at 7X of novel fibers 270a, 270b, and 271c of Example 21. The lengths along the backbone or spine of the structures 271a–271c are 8.68, 9.33, and 7.35 mm, respectively. The diameter of the circumscribing circle for structures 271a–271c are 7.1, 6.7, and 6.0 mm, respectively. All of the lengths and diameters are in millimeters and are the actual values from the unmagnified novel fibers.

Figure 27B:
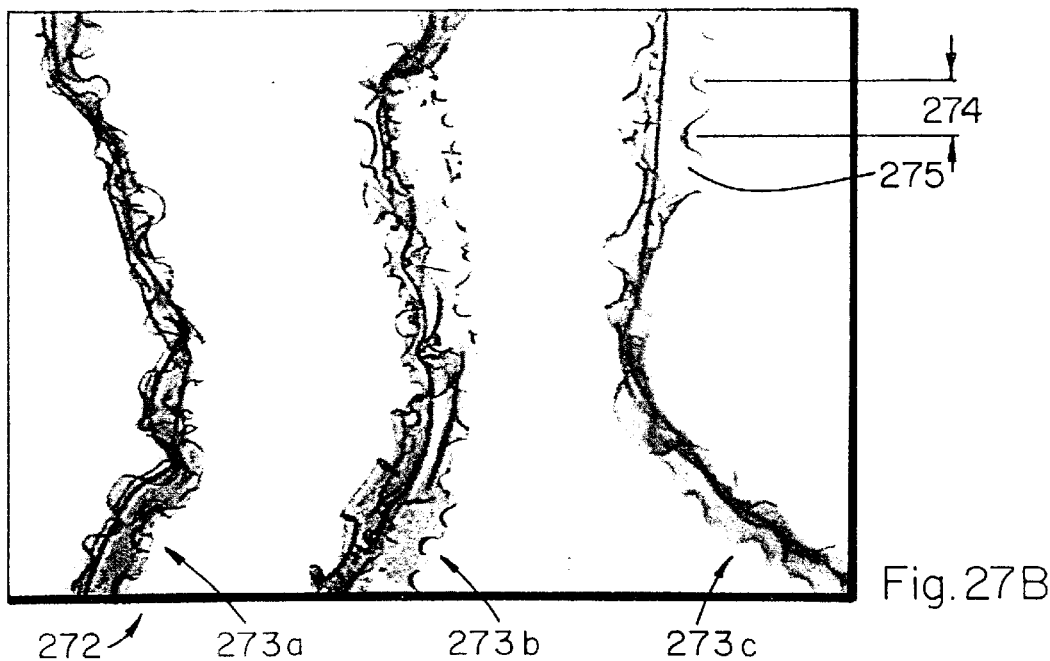
FIG. 27B is a photocopy of a color photograph at 40X of the novel fibers of Example 21.

FIG. 27B shows a photograph at 272 at 40X of the novel fibers 273a, 273b, and 273c of Example 21. FIG. 27B shows the length 274 of 200 microns over which the azimuthal orientation of the wall 275 appears to undergo one complete sinusoidal oscillation in azimuthal position.

Figure 28A:
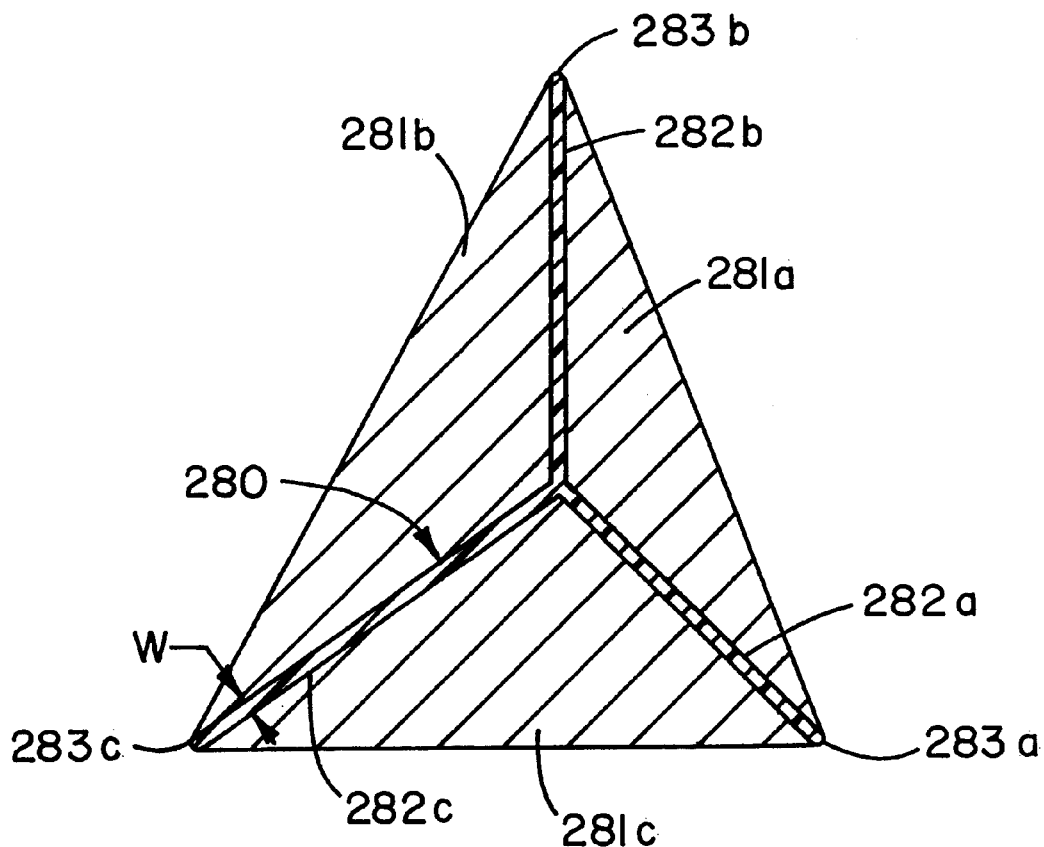
FIG. 28A is a schematic of a cross-section of a fiber for use in illustrating the definition of the single fiber bulk factor.
Figure 28B:
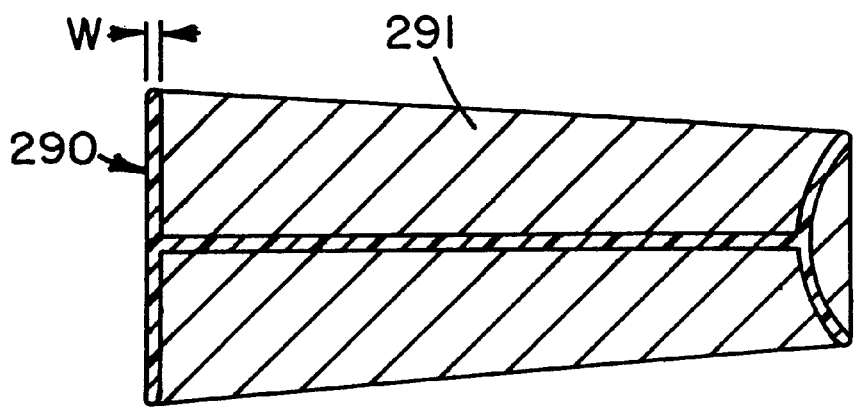
FIG. 28B is a schematic of a cross-section of a fiber for use in illustrating the definition of the single fiber bulk factor.

FIG. 28A–B illustrate the definition of the single fiber bulk factor which is the cross-sectional area of the channels divided by the cross-sectional area of the fiber. FIG. 28A shows a fiber cross-section 280 having a width W and arms 282A, 282B, and 282C having distal tips 283A, 283B, and 283C. The arms 282A, 282B, and 282C define the cross-section channel areas 281A, 281B, and 281C. The cross-sectional channel areas 281A, 281B, and 281C are defined by the straight lines segments tangent to the distal tips of the arms and the surfaces of the arms. A determination, in arbitrary units, of the cross-section area of the channels provides an area of 225. A determination of the cross-sectional area of the fiber in the cross-section 280 provides an area of 60. Therefore, the single fiber bulk factor for the cross-section 280 is 225/60=3.8. FIG. 28B shows the fiber cross-section 290 and the cross-sectional area of the channel 291 in hashing. Determination, in arbitrary units, of the area of the cross-section of the channels 291 and the area of the cross-section 290 of the fiber provides 225 and 44, respectively, in arbitrary units. Therefore, the single fiber bulk factor for FIG. 28B is 5.1.

FIG. 29 is a schematic cross-section of a fiber (solid line) enclosed by line segments AB, BC, CD, and DA (dashed lines) between the points A, B, C, and D. The line segments between the points a, b, c, and d enclose the channel regions A1, A2, A3, and A4. The arms 291 and 294 meet at an end of base 295. The arms 292 and 293 meet at another end of base 295.

EXAMPLES

Example 1

Example 1 discloses the preparation of novel fibers that in the as spun state have H-shaped fiber cross-sections. The novel fibers were made using the "spin-shrink-lube-cut" process.

Poly(ethylene terephthalate) (PET) polymer having an inherent viscosity (IV) of 0.70 with 0.2% $TiO_2$ was used. IV was measured at 25° C. at a polymer concentration of 0.50 g/100 milliliters (mL) in a mixture of 60 weight percent (wt%) phenol and 40 wt % tetrachloroethane. The polymer was dried to a moisture level of less than or equal to 0.003 wt % in a Patterson Conaform dryer at 120° C. for a period of 8 hours. The polymer was extruded at 282° C. through an Egan extruder 1.5" (38.1 mm) diameter, with a length to diameter ratio of 28:1. The fiber was extruded through the 38 orifice spinnerette I-1083, wherein each aperture had the generally "H" shape shown in FIG. 1. The quench air system had a crossflow configuration. The quench air velocity was about 103 ft/minute. A spinning lubricant was applied via ceramic kiss roll. The lubricant level on the fiber was about 0.50% by weight. Fibers of 23.9 dpf (26.6 dtex) as spun were wound at 2200 meters per minute (m/min) on a Barmag SW4SL winder. FIG. 2 shows cross-sections of the as-spun fibers of Example 1. The as-spun fiber had a shape factor of 4.02.

Thirty packages of fibers were made on the Barmag winder. Doff time for each package was 5 minutes. The undrawn fibers were creeled (all 30 packages) and dried on a hot-air dryer oven at 200° C. for 5 minutes. The fibers were shrunk in the dryer. A spinning lubricant was sprayed in an amount of 0.8 wt % on the tow after the tow had been dried. Then, the fibers were cut to ¼ inch staple lengths. The resulting fibers were very distorted and were representative of novel fibers of the present invention.

The composition of spinning lubricant was a 10 wt % solids water dispersion of the following composition: 98 wt % solids polyethylene glycol (20) sorbitan monolaurate and 2 wt % solids 4-cetyl, 4-ethyl morpholinium ethosulfate.

FIG. 3 shows seven cross section of the novel fibers at different positions along the length of the fibers. As apparent from FIG. 3, the cross-sections are highly variable. The shrinking step distorted the cross-section. The distortion is characterized by (1) a short-range distortion factor (SRDF) and (2) a long-range distortion factor (LRDF). These distortion factors are measured as per procedure described hereinbelow.

FIGS. 4A and 4B show photographs of the shrunk and cut fibers at 7X and 40X magnification. The structural properties for the novel fibers of FIGS. 4A and 4B were a dpf of 33 (36.7 dtex); staple cut length=¼" (6.4 mm); average length along the backbone contour $L_0$=8.2 mm; average diameter of circumscribing circle $L_1$=6.9 mm; SFBF=2.7; SRDF=26; and LRDF=0.15.

The absorbency characteristics for the novel fibers of Example 1 at a fiber bulk density of 0.0393 g/cc were as follows: absorbency of 10.9 g water/g fiber; wet collapse of 0%; water release at a pressure of 1 psi of 26.8%; $R_1$ (defined as the initial rate of water absorption upon the first insult by the liquid in grams per second) of 21.7 g/sec; and $R_{avg}$ (defined as the average rate of initial water absorption during 2nd, 3rd, 4th, and 5th liquid insults, $(R_2+R_3+R_4+R_5)/4$) of 1.7 g/sec. Details of measuring these absorbency characteristics are discussed below.

FIG. 4A shows six individual fibers. The numbers in the upper row were the measured values for the lengths $L_0$ along the backbone of the fibers to which they are adjacent. The numbers in the lower portion of the figure were the diameter $L_1$ of circle circumscribing the respective fiber. For example, the filament on the extreme left hand side of FIG. 4A had $L_0$=7.74; $L_1$=6.8; and therefore the LRDF)=$(L_0-L_1)/L_0$= (7.74−6.8)/7.74=0.12. Likewise, the LRDF, for 50 fibers were measured and averaged to obtain the average LRDF for cut fibers of Example 1 of 0.15.

FIG. 3 shows cross-sections of the materials of Example 1 at 111X. Each cross-section photograph was circumscribed by a polygon as per procedure described for SRDF. Material Area, $M_{area}$, is the cross-sectional area of the polymer structure. For the cross-section identified by number 2 in FIG. 3, $M_{area}$=4346$\mu^2$. Channel area ($C_{area}$) is the area enclosed between the sides of the polygon and the polymer structure. For cross-section number 2, $C_{area}$= 8450$\mu^2$. The ratio $C_{area}/M_{area}$ for cross-section number 2 is 1.94. The $C_{area}/M_{area}$ ratio was calculated for 50 cross-sections, and their average ($X_{av}$) and standard deviation $\sigma$ determined for the 50 measurements. The SRDF is defined to be the percent of the coefficient of variations of the channels' cross-sectional area to the material's cross-sectional area, or SRDF=$(\sigma/X_{av})*100$. For the material of Example 1, SRDF is 26.

Example 2

Example 2 discloses the preparation of novel fibers having H-shaped fiber cross-section in the as spun state. These novel fibers were made via the "spin-draw-shrink-lube-cut" process.

The extrusion system was the same as in Example 1. The spinnerette identified as I-1042 having 46 apertures with the shape and dimensions as shown for FIG. 5 was used. PET having an IV of 0.76 was used. The extrusion temperature was 286° C. Quench air flow velocity was 68 ft/min which corresponded to a ΔP of 0.30 inches of water. The spinning lubricant was the same as in Example 1. The take-up speed was 1800 m/min. The as-spun fiber had a "H" cross-section shape and the dpf was 11.2. Forty packages of 7-minute doff time were made. The shape factor of the as-spun fiber was 2.96. The rest of the fiber extrusion process was the same as described for Example 1.

As-spun fibers were further processed on a tow line. Forty ends were in a creel. The tow was drawn in a water bath at 70° C. at a draw ratio of 1.84X. The tow was fed to the water bath at 24.5 m/min and the exit draw roll speed was 45 m/min. A de-watering air jet at 20 psi was used to remove excess water from the tow bundle. The tow was further processed to provide rotationally constrained shrink through a hot-air oven at a temperature of 196° C. for 3 minutes. The lubricant of Example 1 containing 80 wt % solids and 20 wt % water was sprayed after the dryer. The fibers were cut to ¼" staple length via a model 66 cutter. FIG. 6 shows the cross-sections of these fibers. Note the variations in the cross-sections shown in FIG. 6.

FIGS. 7a, b, and c show optical photographs at 80X, 36X, and 7X magnification for the shrunk cut fibers for Example 2. The characterization of these material was as follows: dpf=9.8 (10.9 dtex); Cut Staple Length=¼" (6.4 mm); Avg. Length along the backbone, $L_0$=8.3 mm; Avg. diameter of circumscribing circle, $L_1$=6.7 mm; SFBF=2.0; SRDF=27; and LRDF=0.18.

Absorbency characteristics for Example 2 at 0.0393 g/cc density were as follows: Absorbency=15.2 g $H_2O/g$; Wet Collapse (%)=1.7%; Water release at 1 psi=30.4%; $R_1$=25.1 g/sec; and $R_{avg}$=0.7 g/sec.

Example 3

Example 3 discloses the preparation of novel fibers having H-shaped fiber cross-section in the as spun state. These materials were made via the "spin-shrink-lube-cut" process as in Example 1.

The extrusion system was the same as used in Example 1. The polymer used in this Example was PET of 0.76 IV, spinnerette used was H-shaped I-1083 with 38 orifices. Extrusion temperature was 282° C. Quench air flow corresponded to 0.70 inch water pressure drop (air velocity of 103 ft/minute). Spinning lubricant was the same as Example 1. Take-up speed was 2200 m/min. As-spun dpf=24.8. Total package denier=944. Shape factor of as-spun fiber=3.28. The rest of the fiber extrusion process was same as described in Example 1. Thirty-nine packages were spun with a doff time of 7 minutes.

As-spun fibers were further processed on a tow line. The fibers were shrunk at 195° C. for 5 minutes in the dryer-oven and cut to ¼" length. These novel fibers had a dpf of 55. FIG. 8 shows the cross-section of the novel fibers. FIG. 9 shows the optical photograph of the novel fibers at 7X and 40X magnification.

The characteristics of novel fibers were as follows: dpf= 55 (61.1 dtex); Cut Staple Length=¼" (6.4 mm); Avg. length along the backbone, $L_0$=8.7 mm; Avg. diameter of circumscribing circle, $L_1$=6.8 mm; SFBF=1.6; SRDF=32; and LRDF=0.20.

Absorbency characteristics at 0.0393 g/cc density were as follows: Absorbency=7.1 g $H_2O$/fiber; Wet Collapse= 11.1%; Water release at 1 psi=26.4%; $R_1$=15.5 g/sec; and $R_{avg}$=1.1 g/sec.

Example 4

Example 4 shows the novel fibers of present invention cut to ½" staple length. These novel fibers are made as in Example 3, and were cut to ½" staple length instead of ¼" staple length of Example 3. FIG. 10 shows these novel fibers at 7X. Physical characteristics of novel fibers were as follows: dpf=55 (61.1 dtex); Cut Staple Length=½ inch; Avg. length along the backbone, $L_0$=16.3 mm; Avg. diameter of circumscribing circle, $L_1$=11.9 mm; SFBF=1.9; SRDF= 29; and LRDF=0.26.

Absorbency characteristics of the novel fibers at 0.0393 g/cc density were as follows: Absorbency=6.6 g $H_2O$/g material; Wet collapse=0%; Water release at 1 psi=26.9%; $R_1$=12.9; and Ravg=0.9.

Example 5 (comparative)

Example 5 shows the absorbency characteristics of fluff pulp. Fluff pulp suffers from high wet collapse (25%) and high water release under pressure (58.3% at 1 psi). Absorbency characteristics of fluff pulp at 0.0393 g/cc density were as follows: Absorbency=19.6 g water/g fiber; Wet Collapse (%)=25%; Water release at 1 psi=58.3%; $R_1$ initial rate, 1st insult=25.2 g/sec; and $R_{avg}$=2.5 g/sec.

Example 6

Example 6 fibers were made using the novel fibers of Example 1 and a superabsorbent polymer (SAP) precursor solution available from Camelot Superabsorbents, Ltd., of Calgary, Alberta, Canada. U.S. Pat. No. 5,151,465 discloses uncured polymer compositions that can be made into fibers using conventional fiber-forming processes and cured to produce fibers capable of absorbing at least 60 times their weight of 0.9% sodium chloride solution. The SAP precursor was identified as Fibersorb SA 7200, CTS-HMW. Based on Camelot's MSDS and patents assigned to Camelot, the composition of SAP precursor solution was approximately as follows 74.5 wt % water, 19.5 wt % Trade Secret 4802-01, 5.0 wt % Sodium Hydroxide, 0.6 wt % Glycerol, and 0.4 wt % Trade Secret 4803-02.

The composition of Trade Secret 4803-01 is believed to be a copolymer of maleic anhydride and isobutylene of equal mole ratios of the two noted monomers. Typical molecular weight of the copolymer is in the range of 200,000 to 300,000. The composition of Trade Secret 4803-02 is not known, but likely includes a second cross-linking agent which is the function of glycerol.

Fifty grams of starting material shrunk to 33 dpf was sprayed with 105 g of 5% SAP precursor solution obtained from Camelot. The starting material was sprayed with the SAP solution and was dried in an oven at 120° C. for 60 minutes. The dried sample was further cured at 195° C. for 16 minutes. The cured sample was fluffed in a blender and stored for absorbency testing. This process of making novel fibers enables coating the grooves of the fiber with a superabsorbent polymer.

Coating the grooves with SAP helps in permanent storage and distribution of bodily liquids in absorbent products utilizing these novel fibers. The novel fibers had theoretically 5.25 g of SAP coated per 50 grams of the starting fiber or 9.5% of SAP coated on final fiber. The results of the absorbency testing at 0.0393 g/cc density for the final fiber were as follows: Absorbency=20.9 g $H_2O$/g; Wet Collapse (%) 0%; Water release at 1 psi=29.1%; $R_1$=5.2 g/sec; and $R_{avg}$=5.9 g/sec.

Example 7

The starting material for Example 7 was the novel fibers of Example 1. 210 grams of 5% SAP precursor solution from Camelot was sprayed onto 50 grams of starting material. The sprayed sample was dried in an oven at 120° C. for 80 minutes and further cured at 195° C. for 16 minutes. The resulting novel fibers theoretically were 16.67% SAP coated on 83.33% base material. The novel fibers were fluffed in a blender and stored in zip-lock plastic bags for subsequent absorbency testing.

The results of the absorbency testing at 0.0393 g/cc density were as follows: Absorbency=26.1 g $H_2O$/g; Wet Collapse (%)=0%; Water release at 1 psi=20.7%; $R_1$=4.2 g/sec; and $R_{avg}$=4.5 g/sec.

Example 8

The novel fibers of Example 1 were used as the starting material. 535 grams of 5% SAP precursor solution was sprayed onto 50 grams starting material. The sprayed sample was dried at 120° C. for 165 minutes and cured at 195° C. for 16 minutes. The resulting novel fibers theoretically had 33.3% SAP and 66.7% by weight starting material. The novel fibers were fluffed in a blender and stored in plastic zip-lock bags.

Water absorbency was significantly enhanced as one increases the amount of SAP. The results of the absorbency testing at 0.0393 g/cc density were as follows: Absorbency= 41.1 g $H_2O$/g; Wet Collapse (%)=0%; Water release at 1 psi=8.1%; $R_1$=5.2 g/sec; and $R_{avg}$=3.0 g/sec.

Example 9

Blends of fluff pulp and the novel fibers of Example 1 (33 dpf, H-cross-section, ¼" cut) were made in a blender and the resulting materials were tested for absorbency behavior at a density of 0.0393 g/cc. Following blends were tested:

| Blend Composition | | | Absorbency (g $H_2O$/g Blend) | R1 Initial Rate Upon $1_{st}$ Insult g/sec. | Water Released at 1 psi Load (%) |
| --- | --- | --- | --- | --- | --- |
| Fluff Pulp (%) | Materials of Example 1 (%) | Wet Collapse (%) | | | |
| 100 | 0 | 25.0 | 19.6 | 25.2 | 58.3 |
| 80 | 20 | 20.1 | 20.6 | 27.5 | 52.0 |
| 60 | 40 | 14:9 | 19.6 | 26.3 | 48.4 |
| 40 | 60 | 10.7 | 18.8 | 26.3 | 39.0 |
| 20 | 80 | 5.9 | 15.6 | 25.5 | 28.6 |
| 0 | 100 | 0.0 | 10.9 | 21.7 | 26.8 |

The wet collapse of blended materials reduces significantly when compared with the wet collapse of fluff pulp. Also, percent water release at 1 psi decreases significantly with increasing levels of starting materials.

Example 10

The fibers of Example 10 were prepared using a spin-cut-shrink-lube process instead of the shrink-cut process of Example 1. Using as-spun fibers of Example 1 for the starting material, an as-spun sample of 23.3 dpf, H-shaped cross-section was made at 3000 m/min spin speed. Quench air flow of 112 ft/min air velocity corresponded to a ΔP of 0.80 inches water was made from the I-1083 spinnerets. The rest of the parameters were the same as that for Example 1. The as-spun fiber was cut into ½", 1", 1½"and 2" staple fiber lengths (about 10 g at each length). These cut samples were shrunk in an oven at 170° C. for 5 minutes and sprayed with about 1% of a spinning lubricant. The lubricant was a 10 wt % solids water dispersion of the following components: 10 wt % solution of poly[polyethylene glycol (1400)

terephthalate], 44.1 wt % solids polyethylene glycol (400) monolaurate (oxyethylene fatty acid ester), 44.1 wt % solids polyethylene glycol (600) monolaurate (oxyethylene fatty acid ester), and 1.8 wt % solids 4-cetyl, 4-ethyl morpholinium ethosulfate (alkyl quatemary ammonium salt of inorganic ester).

The shrinkage was about 50%. The results of the absorbency test for spin-cut-shrink-lube process fibers of Example 10 are shown below:

| As-Spun Fiber Cut Length | % Wet Collapse | Absorbency g/H$_2$O/g Fiber |
|---|---|---|
| ½" | 2.4 | 13.2 |
| 1" | 0 | 11.2 |
| 1 ½" | 0 | 12.2 |
| 2" | 0 | 13.1 |

Example 11

The fibers of Example 11 were prepared using a spin-draw-cutshrink-lube process. 7 dpf fibers having 4DG-shape cross-section were spun and drafted on a tow line. The as-spun fibers had a shape factor of 2.9. The fibers were subjected to a two-stage draw with the first stage being in a water bath at 70° C. having a draw ratio of 1.75X and the second stage being in a steam chest at 146° C. having a draw ration of 1.3X. The overall draw ratio was about 2.25X. The drawn fiber was then cut to ¼" staple length and subsequently heat-shrunk in an oven at 200° C. for 5 minutes.

The physical characteristics of the novel fibers were as follows: dpf=6.5; SFBF=0.5; SRDF=26; LRDF=0.32; $L_0$=11 mm; and $L_1$=7.4 mm. The results of the absorbency testing at 0.0536 g/cc density were as follows: Absorbency= 16.8 g H$_2$O/g; Wet Collapse (%)=0%; Water release at 1 psi=44%; $R_1$=9.2 g/sec;

Example 12

U-shaped fibers were extruded through the Egan extruder of Example 1. The following spinning parameters were used. The spinnerette used in Example 12 was I-1127 having 16 orifices, each having the dimension shown in FIG. 11. PET having a 0.70 IV and 0.2 wt % TiO$_2$ was extruded. Quench air velocity was 114 ft/min. Extrusion temperature was 282° C. The lubricant used was the same as Example 1. Take-up speed was 3000 m/min. The as-spun fiber had a dpf of 19.9 and a shape factor of 3.58. The as-spun fiber was heat shrunk in a dryer oven at 180° C. for 5 minutes and then cut to ¼" staple length. FIG. 12 shows the fiber cross-section of the as-spun fiber. FIG. 13 shows the cross-section of the resulting novel fibers of the present invention. FIG. 14 shows a photocopy of a photomicrograph of these novel fibers. The ¼"-cut fibers were tested for absorbency behavior at 0.0393 g/cc density with the following results: Absorbency=12.8 g H$_2$O/g; Water release at 1 psi=60.5%; $R_1$=20.7 g/sec; and $R_{avg}$=1.3 g/sec. The structural properties of these fibers are as follows: dpf=28; SFBF=0.8; SRDF=66; LRDF=0.11; $L_0$=7.3 mm; and $L_1$=6.5 mm.

Example 13

In Example 13, the novel fibers obtained from Example 12 cut to the ¼" staple size were further shrunk in hot water at 90° C. for 1 minute and dried in an oven at 120° C. The resulting novel fibers were fluffed in a blender and characterized for their SRDF, LRDF, and other parameters. These materials have higher LRDF than the materials of Example 12. FIG. 15 shows the photographs of the materials of Example 13 at 7X. The results are as follows: dpf=33.3; SFBF=1.7; SRDF=46; LRDF=0.29; and $L_0$=5.4 mm; and $L_1$=3.8 mm.

Example 14

Example 14 discloses novel fibers having 4DG-shape fiber crosssection.

The 4DG-shaped fibers were extruded through the Egan extruder used in Example 1 using the spinnerette I-1004 whose apertures are illustrated in FIG. 16. The I-1004 spinnerettee had 16 apertures. Following spinning parameters were used in this Example 14. PET having 0.70 IV and 0.2% TiO$_2$ was extruded. The extrusion temperature was 282° C. The quench air flow was 180 ft/min. The as-spun dpf was 19.9. The shape factor was equal to 3.9. The fibers were processed as in Example 1, heat shrunk in a dryer oven at 200° C. for 5 minutes, and cut into ¼" long materials. FIG. 17 shows the fiber cross-section of the as-spun fiber of Example 14. FIG. 18 shows the resulting novel fibers of Example 14. The structural properties of the Example 14 fibers are as follows: dpf=26; SFBF=1.7; SRDF=18; LRDF= 0.10; $L_0$=7.3 mm; and $L_1$=6.6 mm.

Example 15

In Example 15, the ¼" cut fibers obtained from Example 14 were further shrunk in hot water at 90° C. for 1 minute and dried in an oven at 120° C. The resulting novel fibers were fluffed in a blender and characterized for their physical parameters. FIG. 19 shows the fiber cross-sections and FIG. 20 shows photographs of these novel fibers. The structural properties of the novel fibers of Example 15 are as follows: dpf=36; SFBF=1.9; SRDF=11; LRDF=0.35; $L_0$=4.4 mm; and $L_1$=2.9 mm.

Example 16

Example 16 discloses that addition of a surfactant to the SAP precursor solution enhances the initial rate of water absorption, $R_1$, in these novel fibers. Example 6 shows that $R_1$ for the novel fibers is 5.2 g/sec, significantly lower than that for the novel fibers of Example 1. Coating Camelot's precursor SAP solution on to the novel fibers of Example 1 reduces $R_1$. In this Example 16, LUROL 1852 was added to the SAP precursor solution prior to coating the base material of Example 1 with the SAP. LUROL 1852 is a nonionic, ethoxylated fatty acid ester obtained from Goulston Technology, Monroe, N.C. The LUROL 1852 composition is a trade secret. Ten grams of the novel fibers of Example 1 were coated with a 5% solution in water containing 1 gram of precursor solution SAP and 1 gram of LUROL 1852. The coated material was dried in an oven at 120° C. for 50 minutes and subsequently cured at 195° C. for 15 minutes. The resulting novel fibers were tested for absorbency behavior. The initial rate of water absorption, $R_1$, upon first insult was 15.2 g/sec. Thus, addition of appropriate surfactants to the SAP solution is one method of enhancing $R_1$ in the novel materials.

Example 17

Example 17 illustrates the utility of adding high levels of SAP powder to the novel fibers of the invention. This is particulaly desirable for thin diapers having high absorbent core density. Blends of the novel fibers of Example 1 (having 33 dpf and the H-cross-section) with superabsorbent polymer, Favor®, SXM70 from Stockhausen, which is a salt of crosslinked polyacrylic acid, were made in a laboratory blender at various blend levels as shown in Table 1. The above blended materials were tested for the absorbency behavior at 0.1118 g/cc density and the results are shown in Table 1.

TABLE 1

Absorbency Behavior of Blends Of TA and SAP at 0.118 g/cc density

| S. No. | % SAP (by wt.) | Absorbency g. water/ g. blend | Wet Collapse (%) | % Water Release at 1 psi Load | R1 g/sec. | $R_{avg}$ g/sec |
|---|---|---|---|---|---|---|
| 1 | 20 | 10.3 | −50 | 0.3 | 20.4 | 2.6 |
| 2 | 30 | 13.1 | −70 | 0.6 | 20.6 | 2.8 |
| 3 | 40 | 13.1 | −70 | 0.04 | 20.5 | 3.0 |
| 4 | 50 | 12.9 | −64 | 1.3 | 21.6 | 2.5 |
| 5 | 60 | 15.3 | −80 | 0.96 | 18.5 | 2.7 |
| 6 | 70 | 16.7 | −94 | 0.83 | 18.5 | 2.6 |
| 7 | 0 | 8.6 | −10 | 4.5 | 33.2 | 5.2 |

A negative number for wet collapse implies the structure actually "expanded" upon "wetting". Note the relatively low percentage of water release at 1 psi load.

Example 18

Example 18 discloses a process for making novel fibers by a spin-cut-shrink-lube process. In Example 18, fiber is spun at relatively high speeds of greater than 1500 m/min. High quench air velocity is used. This is a continuous process in which the fiber is cut to small staple lengths and in a continuous manner shrunk in hot (>80° C.) air and sprayed with hydrophilic lubricants. The resulting materials are highly convoluted, shrunk, short-cut materials.

Example 19

Example 19 illustrates novel fibers of the present invention made by the "spin-cut-shrink-lube" process. The extrusion system of Example 1 was used. The PET polymer was dried to a moisture level of less than or equal to 0.003 wt % in a Patterson Conaform dryer at 120° C. for a period of 8 hours. PET polymer having an IV 0.76 was extruded. The polymer was extruded at 283° C. through an Egan extruder using the spinnerette I-1042. The aperture design of the I-1042 spinnerette is shown in FIG. 5. The fibers were quenched with air at 120 ft/min. The take-up speed was 2500 m/min, as-spun dpf was 8.8. The shape factor of the fiber was 3.0. The as-spun fibers were cut into ½" long fibers and shrunk in hot water at 90° C. for 2 minutes. The resulting fibers were dried in an oven at 120° C. and fluffed in a laboratory blender. They were then sprayed with the lubricant of Example 10. The final lubricant on the fiber was about 0.8 wt % of the fibers. These fibers were allowed to air dry at room temperature (about 23° C.) for 16 hours. The physical characteristics of the resulting novel fibers were as follows: dpf=20.5; SFBF=1.5; SRDF=25; LRDF=0.20; $L_0$=6.4 mm; and $L_1$=5.1 mm.

The absorbency characteristics of the novel fibers at 0.0393 g/cc were as follows: Absorbency=14.2 g $H_2O$/g; Water release at 1 psi=32.5%; $R_1$ (g/sec)=20.8; and $R_{avg}$=1.9 g/sec.

Example 20

Example 20 discloses novel fibers having an Y-shaped cross-section. The Y-shaped product was made via a "spin-cut-shrink-lube" process using the following parameters.

PET having an IV 0.76 was extruded through the Egan extruder system described in Example 1, but using the spinnerettee I-1195 having the Y shaped apertures shown in FIG. 21A. The polymer was extruded at 282° C. through the Egan extruder. The PET polymer was dried to a moisture level of less than or equal to 0.003 wt % in a Patterson Conaform dryer at 120° C. for a period of 8 hours. The quench air velocity was 185 ft/min. The take-up speed was 2200 m/min. The as-spun fiber was 65 dpf and a shape factor of 5.0. The as-spun fiber was cut ½" long and shrunk in hot water at 95° C. The cut, shrunk materials were dried in an oven at 120° C. The fiber was then lubricated with the lubricant of Example 10, at a level of 0.8–1.0% by weight. The novel fibers thus obtained were highly distorted and convoluted.

FIG. 22 shows a fiber cross-section of as-spun fibers of Example 20. FIG. 23 shows cross-sections of the novel fibers of Example 20. FIG. 24 is a photograph of novel fibers of Example 20 at 7X.

The measured physical properties of the novel fibers of Example 20 are as follows: dpf=132; SFBF=4.0; SRDF=36; LRDF=0.49; $L_0$=14.4 mm; and $L_1$=7.2 mm.

The absorbency characteristics of the novel fibers at 0.0393 g/cc were as follows: Absorbency=8.9 g $H_2O$/g; Wet Collapse (%)=8.3; Water released at 1 psi=22.8; $R_1$ (g/sec)= 16.7; and $R_{avg}$=1.2 g/sec.

Example 21

Example 21 discloses the preparation of novel fibers having cross-sections as shown in FIG. 25. Example 12 used PET polymer of 0.76 I.V. with 0.2% $TiO_2$. The Egan extrusion system of Example 1 was used to extrude at 280° C. the polymer dried as in Example 1 through the spinnerettee I-1198 having 11 orifices the design of which is shown in FIG. 26. The quench air velocity was 68 ft/min. The spinning lubricant was the same as in Example 19. The lubricant level of the fiber was about 0.8% by weight. The 25 dpf as-spun fibers were wound at 2500 m/min spinning speed on a Barmag SQ4SL winder. The as-spun fiber shape factor was 4.6. The as-spun fibers were cut into about ½" long fibers, shrunk in hot water at 90° C. for 1 minute and dried in oven at 120° C. The resulting materials were sprayed with the lubricant of Example 10 (0.8% by wt.) and dried overnight. FIG. 27 shows optical photographs of resulting materials at 7X and 40X magnification.

The physical characteristics of the novel fibers were characterized as follows: dpf=50.3; SFBF=3.1; SRDF=32; LRDF=0.23; $L_0$=8.7 mm; $L_1$=6.7 mm.

The absorbency characteristics of the novel fibers at 0.0393 g/cc were as follows: Absorbency=10.9 g $H_2O$/g material; Wet collapse=3.3%; Water released at 1 psi= 28.2%; $R_1$=21.7 g/sec; and $R_{avg}$=1.9 g/sec

TEST PROCEDURES

Absorbent Property Parameters utilized in the present invention include the following:

a. Absorbency, which is measured in grams of distilled water absorbed per gram of absorbent material.

b. Wet collapse, which is the percentage decrease in the height of the absorbent material upon wetting.

c. Water released, which is the percent of water that has been absorbed by the absorbent material that is released when the absorbent material is placed under a pressure of 1 pound per square inch (psi).

d. $R_1$, which is the initial rate of water absorption upon a first wetting or insult of the absorbent material, and which is measured in grams of distilled water absorbed per second.

e. $R_{avg}$, which is the average initial rate upon the second through fifth contacts or insults of the absorbent material (i.e., $(R_2+R_3+R_4+R_5/4)$, and which has units of grams of distilled water absorbed per second.

The absorbent parameters were measured using a porous wire basket in which the absorbent materials are placed. The wire basket is made from a 0.008 inch diameter wire having a mesh size of 20. The wire basket has a cylindrical wall having a diameter of 6 centimeters. The height of the wall is 10 centimeters. The bottom of the basket is flat. The wire basket can be used to measure absorbent properties of any of the absorbent materials such as fluff pulp, synthetic absorbent materials, such as those disclosed hereinabove, SAP, and blends of the foregoing. The absorbent materials are prepared for deposition into the wire basket by first fluffing them in a laboratory blender. This step bulks up and uniformly mixes the absorbent material.

Next, a predetermined weight, WI grams of the fluffed absorbent material is deposited in the wire basket. The fluff absorbent material may then be pressed down so that it fills a specified volume of the wire basket in order to provide a specified and uniform density. Typically, 10 grams of the fluff absorbent material is deposited to the basket.

Next, the initial height of $h_1$ in centimeters of the absorbent material in the basket is measured, and the dry weight of the absorbent material and the basket is measured.

Next, 355 milliliters of distilled water is poured into a rectangular container having bottom dimensions of 20.6 centimeters by 23 centimeters. That base dimension and that volume of distilled water fills the container up 0.75 centimeters above the base. The height of the liquid above the base is the important factor in this step, because the height of the liquid above the base indicates how much of the basket will be submerged into distilled water in the following step.

Next, the basket is placed into the distilled water container for two seconds and then removed from the distilled water container. The basket is suspended for 10 seconds in order to allow the distilled water that this not retained by the absorbent material to drain out of the basket. Ten seconds after the basket has been removed from the liquid, the basket is weighed. The differences between the weight of the basket with the dry absorbent material and the weight of basket with the wet absorbent material $W_2$ is determined. $R_1$ is then determined. $R_1$ equals $W_2$ (in grams) divided by 2 (in seconds).

Ten minutes after the first insult, the process of placing the basket in the distilled water container for two seconds, suspending the basket for ten seconds, and then weighing the basket is repeated. The weight of the water picked up during the second insult (above the weight of water picked up during the first insult) $W_3$ is then recorded. The rate of water picked up during the second insult $R_2$ is then calculated. $R_2$ equals $W_3$ (in grams) divided 2 (in seconds).

The third insult occurs ten minutes after the second insult. The same procedures are followed to determine $R_3$. Similarly, $R_4$ and $R_5$ are determined by repeating the steps for determining the weight of water pick up for a 2 second insult with the water at ten minute intervals.

The total water absorbency is determined by the following procedures.

Distilled water is placed into a distilled water container up to a height of about 15 centimeters. The basket containing the absorbent material is immersed in this distilled water container for ten seconds. The basket is slowly removed from the distilled water container in order to avoid any accelerative forces. Thus, the basket is removed from the liquid over the period of between about 0.5 and 5 seconds. The basket is suspended so that it can drain for 30 seconds. After 30 seconds, the basket is weighed and the weight of the total water picked up is determined. The total water absorbency is then calculated as the grams of the water absorbed divided by the grams of the dry absorbent material.

Next, the (average) height of the absorbent material in the basket $h_2$ is measured. That is, if the absorbent material no longer has a uniform upper surface, an estimate is made of the average height of the upper surface. The wet collapse is then calculated based upon the initial height $h_1$ of the upper surface prior to wetting and the average height of the upper surface $h_2$ after wetting. The wet collapse is defined as a percentage change in the height as $[(h_1-h_2)/h_1]$ times 100.

The weight of water released (at 1 psi) is determined by the following procedure.

The basket with the absorbent material is submerged for ten seconds in distilled water using the same procedure for the determination of the total water absorbency discussed above. After suspending the basket out of the water for 30 seconds, a weight of 1991.5 grams is placed on top of the absorbent material in the basket for ten seconds. The 1991.5 grams load is a pressure of one pound per square inch. The 1991.5 gram weight is removed from the basket and the basket is weighed in order to determine the weight of the water absorbed after the one pound per square inch load had been applied. The percent water released due to the 1 psi pressure, is then calculated as 100 times the weight of the water released after the load had been applied divided by the weight of the absorbed water prior to when the load had been applied.

AS SPUN FIBER PARAMETERS

Shape Factor

The shape factor is the average of measurements on 20 cross-sections from a fiber. The shape factor is a measure of the deviation of the cross-section of the fiber from round. A round cross-section fiber has a shape factor of one. Irregularly shaped cross-sections have shape factors of greater than one. The mathematical upper limit of shape factors (which is not physically possible) is infinity. The shape factor is defined as the ratio of the perimeter, $P_1$, of the fiber cross-section of the polymeric material to the hypothetical perimeter of, $P_2$, of a round cross-section fiber having the same cross-sectional area, A, as the polymeric material. Therefore, the shape factor is defined as $P_1$ divided by the square root of $(4\pi A)$.

Specific Capillary Volume (SCV), Specific Capillary Surface Area (SCSA), Slenderness Ratio (SR), Capillary Channel Width The following procedures are useful for determination of parameters used to define the as spun fibers and are taken verbatim from U.S. Pat. No. 5,200,248 at column 27 line 45 to column 30 line 12 and column 35 line 63 to column 35 line 59.

The procedures may require preparation of structures of varying lengths, some of which may exceed the length of the structure actually intended for use. It is to be understood that any structures shorter than lengths required by the procedures are evaluated on the basis of equivalent structures having the requisite lengths set forth in such procedures, except as may be otherwise specifically provided. Specific units may be suggested in connection with measurement and/or calculation of parameters described in the procedures. These units are provided for exemplary purposes only. Other units consistent with the intent and purpose of the procedures can be used.

The procedure used to determine Specific Capillary Surface Area (SCSA) and Specific Capillary Volume (SCV) of a capillary channel structure is applied to a photomicrograph which shows a representative cross-section of the capillary channel structure. The cross-section of the structure is prepared for photomicrographing by embedding and microtoming techniques known to those skilled in the art. The following equations are used:

$$SCSA = \text{sum over } x=1 \text{ to } i, \text{ of } P_x/pA_s, \quad (1)$$

$$SCV = \text{sum over } x=1 \text{ to } i, \text{ of } Av_x/pA_s, \quad (2)$$

wherein:

ρ=density of the solid (i.e., polymer);

$A_s$=area of the cross-section of capillary channel solid perpendicular to the capillary channel axis which bounds those capillary channels within the scope of criterial (a) and (b), the sum over x=1 to i of $P_x$=the sum of the perimeters of the cross section of the solid forming each of the capillary channels, x, wherein each perimeter $P_x$ bounds the capillary channel and is within the theoretical closure provided by $C_x$;

the sum over x=1 to i of $Av_x$=the sum of the void areas of the capillary channel structure wherein each $Av_x$ is calculated as the area bounded by the perimeter of the solid forming the channel and by $C_x$; and wherein i is the number of capillary channels in the structure, x refers to specific capillary channels of a capillary channel structure, and $C_x$ corresponds to that part of a circle which is convex toward the interior of the channel and which is of a selected diameter that closes each capillary channel, x, wherein the circle, $C_x$ is sized and positioned according to the following criteria:

(a) the circle, $C_x$, is tangent to both walls of the capillary channel, x, at the points where it meets the walls; and (b) for each capillary channel, x, the circle $C_x$ meeting (a) maximizes $Av_x$ for each such channel, x, subject to the limitations that:

(i) the lines tangential to the intersection of $C_x$ and the capillary channel walls intersect to form an angle of 120 degrees or less; and (ii) $C_x$ can have a radius of no greater than about 0.025 cm with respect to the actual scale of the capillary channel structure (circle radius will be enlarged by the same magnification factor applied to the actual structure in the photomicrograph).

For capillary channel structures having capillary channel wall fluid exchange orifices, the effect on SCV and SCSA will generally not be of numerical significance due to the thin walls of the capillary channel structures hereof, and can generally be disregarded in the calculations.

For capillary channels having multiple points of tangency with a circle of maximum radius, as provided above, the circle is positioned so as to maximize cross-sectional area (Av) of the channel. For capillary channel structures having variation in cross-sectional size or shape, sufficient cross-sections can be evaluated to provide a representative weighted average SCV and/or SCSA. If, however, any portion of the structure of linear length (in the axial direction of the capillary channels) of at least about 0.2 cm, preferably at least about 1.0 cm, has a SCV and SCSA within the claimed ranges hereof, that such structure is said to comprise a capillary channel structure of the present invention.

For capillary channel sheets, particularly those with capillary channel bases of relatively large width, a representative sample of the product having a fraction of the total width of the base can be substituted in place of the entire cross-section of the sheet. Such fractional sample of the sheet preferably has a width of at least about 0.5 cm. The purpose of SCV and SCSA, as defined above, is to provide quantitative analysis of structures characterized by open capillary channels. It is conceivable that such structures can have solid portions, appendages, and the like, which do not otherwise contribute to the definition of the capillary channels in this procedure. The above criteria will exclude perimeter and void areas corresponding to such nonfunctional portions of the structure from the calculations. Also, the cross-sectional area of nonfunctional solid elements is not to be included in the calculation of $A_s$. Exclusion of such perimeters and cross-sectional area is exemplified in more detail below.

Figure 34:
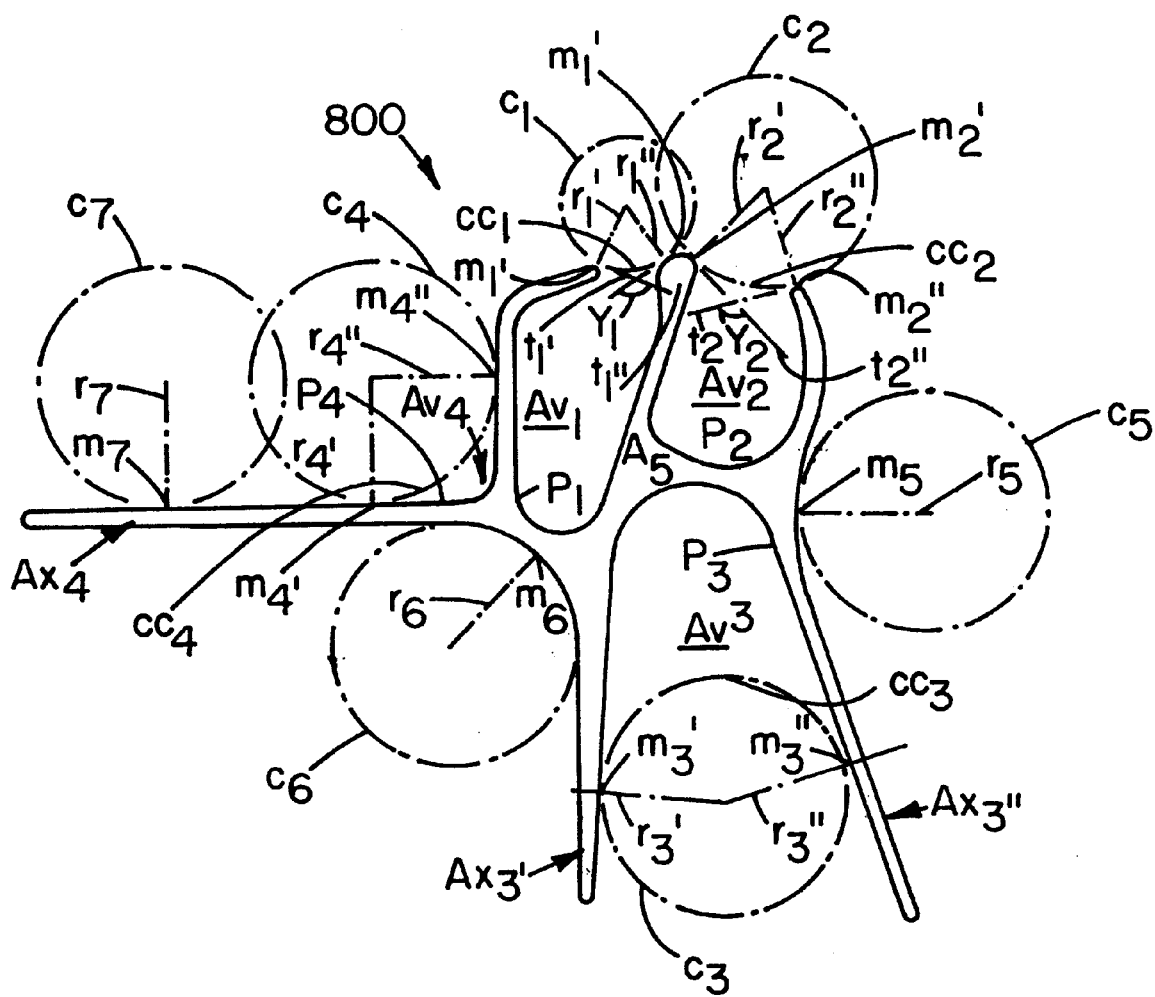
FIG. 34 is a schematic cross-section of a fiber used in defining SCV and SCSA.

FIG. 34 exemplifies a capillary channel structure fragment 800 and application of the SCV and SCSA procedure thereto. Shown is the fragment 800 of solid (i.e., polymer) having area $A_s$, capillary channel void areas $Av_1$, $Av_2$, $Av_3$, $Av_4$, with corresponding capillary channel perimeters $P_1$, $P_2$, $P_3$, $P_4$ and theoretical closure circles $C_1$, $C_2$, $C_3$, and $C_4$. Also shown are circles $C_5$, $C_6$, $C_7$. Radii $r_{1'}$, $r_{1''}$, $r_{2'}$, $r_{2''}$, $r_{3'}$, $r_{3''}$, $r_{4'}$, $r_{4''}$, $r_5$, $r_6$, $r_7$ are each perpendicular to the line tangent to the points of intersection $m_{1'}$, $m_{1''}$, $m_{2'}$, $m_{2''}$, $m_{3'}$, $m_{3''}$, $m_{4'}$, $m_{4''}$, $m_5$, $m_6$, $m_7$, respectively, between the corresponding circles, $C_1$, $C_2$, $C_3$, $C_4$, $C_5$, $C_6$, $C_{67}$ and the solid material of fragment 800.

The circles $C_1$, $C_2$, $C_3$, and $C_4$ are drawn so as to meet the above criteria. As can be seen circles $C_1$ and $C_2$ are limited in radius $r_1$, $r_2$ by angles $y_1$, $y_2$ which represent 120 degree angles of intersection between tangent lines $t_{1'}$, $t_{1''}$, and between $t_{2'}$, $t_{2''}$, respectively. $Av_1$, $Av_2$, $Av_3$, and $Av_4$ are the areas bounded by perimeters $P_1$, $P_2$, $P_3$, and $P_4$ and curves $cc_1$, $cc_2$, $cc_3$, and $cc_4$, respectively. Circles $C_3$ and $C_4$ represent the maximum size circle for capillary channel, wherein the angle of intersection of lines drawn tangent to the circle at points $m_{3'}$, $m_{3''}$ and at $m_{4''}$ and $m_4w$, respectively, would be less than 120 degrees. Thus, as represented in this exemplary figure, circles $C_3$ and $C_4$ would each have radius of 0.025 cm, after reduction for magnification effects. Perimeters are determined as the length of the solid boundary interior to the channels between the points of intersection between the circle and the solid for each channel. $C_5$, $C_6$, and $C_7$ represent circles of maximum radius applied to portions of the structure which do not qualify as capillary channels according to the criteria of this procedure. Hence, P and Av for these circles would be zero. As perimeters $P_1$, $P_2$, $P_3$, and $P_4$, and curves $cc_1$, $cc_2$, $cc_3$, and $cc_4$, can be seen, the area of the solid between $m_{4'}$ and $m_{4''}$ would be included within $A_s$ since such solid corresponds to capillary channel walls bounding channels within the criteria for Av in the calculation of SCV and SCSA. Areas $A_{x3'}$ and $A_{x3''}$, which are bounded by linear extensions of the radii $r_{3'}$, $r_{3''}$, (said radii being perpendicular to the line of tangency between the circle $C_3$ and the walls of the channel), are not included in $A_s$. Likewise, radius $r_{4'}$ truncates area $A_{x4}$ from the calculation $A_s$ based upon extension of $r_{4'}$ of circle $C_4$.

Figure 35:
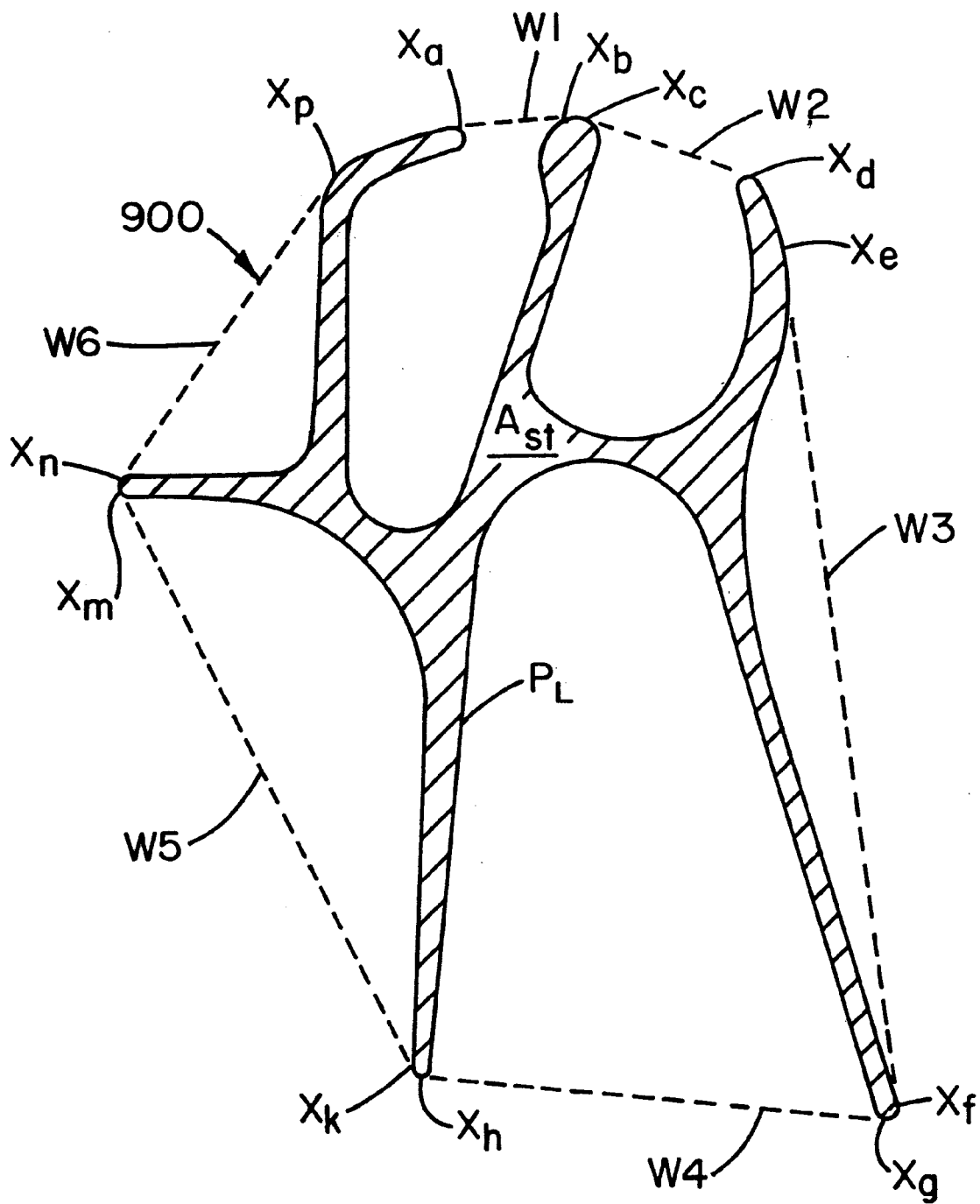
FIG. 35 is a schematic cross-section of a fiber used in defining S and CCW.

Slenderness Ratio (S), Capillary Channel Width (CCW), and Average Structure Thickness ($t_{ave}$) are determined according to the procedures as follow. The procedures are implemented based upon a photomicrograph of a representative microtomed cross-section of the capillary channel structure, as previously described. For capillary channel structures having variation in Slenderness Ratio, Capillary Channel Width, and Average Structure Thickness in the axial direction of the capillary channels, sufficient cross-sections should be evaluated to provide a representative weighted average Slenderness Ratio, Capillary Channel Width, and/or average structure thickness value. If, however, any portion of this structure of linear length in the axial direction of the capillary channels of at least about 0.2 cm, preferably at least about 1.0 cm, has a Slenderness Ratio, capillary channel width, and/or average structure thickness value within the ranges hereof, then such structure may comprise a capillary channel structure of the present invention. Reference is made to FIG. 35 for exemplary purposes of the procedures.

The following equations are used:

$$S = L^2/4A_{st}$$

$$t_{ave} = 2A_{st}/L$$

wherein:

L=total solid perimeter of the cross-section of the structure; and $A_{st}$=total area of the cross-section of the solid forming the structure perpendicular to the capillary channel axis.

The foregoing equation for Slenderness Ratio treats the fiber under consideration as if it has one channel-forming wall therein. For channeled fibers having a functional portion wherein one or more channels are present, the formula for Slenderness Ratio (S) can be given as:

$$S = L^2/4A_{st}N$$

wherein:

L and $A_{st}$ are as hereinbefore defined; and

N=number of channel walls in the structure, said walls being those that have, on one or both sides, channels that are closable by straight closure chords.

CCW is the length of the straight closure chord of a capillary channel wherein said chord closes said intra-structure capillary channel and which tangentially contacts the points of intersection with the capillary channel walls of said channel in such a way to maximize the volume of the channel. (Portions of the structure which do not contribute open channels closable by straight closure chords should be disregarded prior to the above calculations.)

FIG. 35 shows, for exemplary purposes, a cross-section of a capillary channel structure 900 having chords W1, W2, W3, W4, W5, and W6 for capillary channels C1, C2, C3, C4, C5, and C6, respectively, thus N=6. FIG. 35 also indicates the region corresponding to total cross-sectional area $A_{st}$ and indicates continuous line $P_L$, the length of which is the total perimeter L. $X_a$–$X_p$ indicate points of tangency of the chords and the cross-section.

We claim:

1. A distorted, bulky synthetic polymeric fiber comprising:
   (a) a length of said fiber between 2 and about 37 millimeters,
   (b) a cross-section having a plurality of shapes varying along the length of said fiber,
   (c) a single fiber bulk factor between 0.5 and 10.0,
   (d) a short range distortion factor greater than 5, and
   (e) a long range distortion factor between 0.05 and 0.9.

2. The fiber of claim 1 wherein said length is between 2 and 19 millimeters.

3. The fiber of claim 1 wherein said single fiber bulk factor is between 0.5 and 4.0.

4. The fiber of claim 1 wherein said single fiber bulk factor is between 1.5 and 7.5.

5. The fiber of claim 1 wherein said short range distortion factor is between 5 and 70.

6. The fiber of claim 1 wherein said short range distortion factor is between about 18 and about 36.

7. The fiber of claim 1 wherein said long range distortion factor is between about 0.10 and about 0.60.

8. The fiber of claim 1 wherein said long range distortion factor is between about 0.10 and about 0.49.

9. The fiber of claim 1 wherein said fiber has a denier between 3 and 100.

10. The fiber of claim 1 wherein said fiber has a denier between 3 and 30.

11. The fiber of claim 1 wherein prior to being distorted said fiber has a "H" shape cross-section along the length of said fiber.

12. The fiber of claim 1 wherein prior to being distorted said fiber has a "Y" shape cross-section along the length of said fiber.

13. The fiber of claim 1 wherein prior to being distorted said fiber has a "+" shape cross-section along the length of said fiber.

14. The fiber of claim 1 wherein prior to being distorted said fiber has a "U" shape cross-section along the length of said fiber.

15. The fiber of claim I further comprising a coating of a superabsorbent polymer.

16. The fiber of claim 1 further comprising a coating of a blend of superabsorbent polymer and surfactant.

17. The fiber of claim 1 formed from a heat shrinkable polymer.

18. The fiber of claim 17 wherein said polymer comprises poly(ethylene terephthalate).

19. The fiber of claim 1 wherein said polymer comprises polystyrene or foamed polystyrene.

20. The fiber of claim 1 wherein said cross-section and a surface composition of said fiber satisfy the inequality:

$$(Py\cos(\theta a))/d > 0.03 \text{ dynes/den};$$

wherein P is the perimeter of the cross-section of said fiber in centimeters, y is the surface tension of a liquid in dynes per centimeter, θa is an advancing contact angle of the liquid measured on a flat surface made from the same material as said fiber and having the same surface treatment and d is a denier of said fiber in grams of fiber per 9000 meters of fiber.

21. The fiber of claim 1 further having an adhesion tension on a surface of said fiber of greater than 25 dynes/cm with distilled water measured on a flat surface made from the same material as said fiber.

22. An absorbent structure for temporarily acquiring and distributing a fluid comprising a plurality of the fibers of claim 1 in proximity to each other.

23. The absorbent structure of claim 22 having a wet collapse of less than 12 percent at a bulk density of 0.0393 g/cc.

24. The absorbent structure of claim 23 wherein the wet collapse is less than 5 percent.

25. The absorbent structure of claim 24 wherein the wet collapse is essentially zero.

26. The absorbent structure of claim 22 wherein said structure has a bulk density of less than 0.15 grams per cubic centimeter.

27. The absorbent structure of claim 22 having An absorbency in grams of water absorbed per gram of total material in the absorbent structure greater than about 6 and water release at 1 psi of less than about 50 percent.

28. The absorbent structure of claim 27 wherein the water released at one pound per square inch of pressure is less than about 30 percent.

29. An absorbent structure for permanently storing a fluid comprising a plurality of the fibers of claim 1 mixed with fluff pulp, chemically modified fluff pulp, superabsorbent polymer, or combinations thereof.

30. The absorbent structure of claim 29 having a bulk density of greater than 0.10 g/cc.

31. The absorbent structure of claim 30 wherein superabsorbent polymer is mixed with a plurality of the fibers of claim 1 and is present in an amount of greater than 35 weight percent.

32. An absorbent structure for permanently storing a fluid comprising a plurality of the fibers of claim 1 mixed with fluff pulp having a wet collapse of less than 5 percent at a density of 0.0393 g/cc.

33. An absorbent structure for permanently storing comprising a plurality of the fibers of claim 16 in proximity to each other.

34. The absorbent structure of claim 33 having an absorbency in grams of water absorbed per gram of total material in the absorbent structure of greater than about 20, water release at 1 psi of less than 30 percent, and a $R_{avg}$ of greater than 2.5 g/sec.

35. The absorbent structure of claim 33 further comprising fluff pulp, chemically modified fluff pulp, superabsorbent polymer, or combinations thereof.

36. An absorbent product selected from the group consisting of a diaper, a catamenial, and an incontinent device comprising a plurality of the fibers of claim 1.

37. An absorbent product selected from the group consisting of a diaper, a catamenial, and an incontinent device comprising the absorbent structure of claim 22.

38. An absorbent product selected from the group consisting of a diaper, a catamenial, and an incontinent device comprising the fibers of claim 16.

39. An absorbent product selected from the group consisting of a diaper, a catamenial, and an incontinent device comprising the absorbent structure of claim 33.

40. The fiber of claim 1 coated with a mixture comprising a copolymer of maleic anhydride and isobutylene and an additive comprising a nonionic ethoxylated fatty acid ester.

* * * * *